US009567363B2

(12) United States Patent
Hamilton et al.

(10) Patent No.: US 9,567,363 B2
(45) **Date of Patent: *Feb. 14, 2017**

(54) CERTAIN COMPOUNDS, COMPOSITIONS AND METHODS

(71) Applicant: Otsuka Pharmaceutical Co., Ltd., Tokyo (JP)

(72) Inventors: Gregory S. Hamilton, Catonsville, MD (US); Takashi Tsukamoto, Ellicott City, MD (US); Dana V. Ferraris, Eldersberg, MD (US); Bridget Duvall, Nottingham, MD (US); Rena Lapidus, Baltimore, MD (US)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 107 days.

This patent is subject to a terminal disclaimer.

(21) Appl. No.: 14/584,437

(22) Filed: Dec. 29, 2014

(65) Prior Publication Data

US 2015/0210730 A1 Jul. 30, 2015

Related U.S. Application Data

(63) Continuation of application No. 14/088,465, filed on Nov. 25, 2013, now Pat. No. 8,951,987, which is a continuation of application No. 13/556,404, filed on Jul. 24, 2012, now Pat. No. 8,618,075, which is a continuation of application No. 12/252,961, filed on Oct. 16, 2008, now Pat. No. 8,268,800.

(60) Provisional application No. 60/980,397, filed on Oct. 16, 2007.

(51) Int. Cl.

| | |
|---|---|
| ***C07H 19/073*** | (2006.01) |
| ***C07H 19/06*** | (2006.01) |
| ***C07H 19/04*** | (2006.01) |
| ***A61K 31/7068*** | (2006.01) |
| ***A61K 45/06*** | (2006.01) |
| ***C07H 1/00*** | (2006.01) |

(52) U.S. Cl.

CPC ........... *C07H 19/06* (2013.01); *A61K 31/7068* (2013.01); *A61K 45/06* (2013.01); *C07H 1/00* (2013.01); *C07H 19/04* (2013.01); *C07H 19/073* (2013.01); *C07B 2200/13* (2013.01)

(58) Field of Classification Search

None

See application file for complete search history.

(56) References Cited

U.S. PATENT DOCUMENTS

| | | | | |
|---|---|---|---|---|
| 4,017,606 | A | 4/1977 | Hanze et al. | |
| 4,210,638 | A | 7/1980 | Greer | |
| 4,275,057 | A | 6/1981 | Marquez et al. | |
| 4,526,988 | A | 7/1985 | Hertel | |
| 4,808,614 | A | 2/1989 | Hertel | |
| 4,965,374 | A | 10/1990 | Chou et al. | |
| 5,223,608 | A | 6/1993 | Chou et al. | |
| 5,371,210 | A | 12/1994 | Chou | |
| 5,426,183 | A | 6/1995 | Kjell | |
| 5,464,826 | A | 11/1995 | Grindey et al. | |
| 5,521,294 | A | 5/1996 | Wildfeuer | |
| 5,530,110 | A | 6/1996 | Sowers | |
| 5,552,539 | A | 9/1996 | Duplaa et al. | |
| 5,594,124 | A | 1/1997 | Chou | |
| 5,606,048 | A | 2/1997 | Chou et al. | |
| 5,637,688 | A | 6/1997 | Berglund | |
| 5,821,357 | A | 10/1998 | Chou et al. | |
| 5,932,719 | A | 8/1999 | Abushanab et al. | |
| 5,945,547 | A | 8/1999 | Chou et al. | |
| 5,968,914 | A | 10/1999 | Von Borstel et al. | |
| 6,001,994 | A | 12/1999 | Weigel | |
| 6,326,491 | B1 | 12/2001 | Abushanab et al. | |
| 6,344,447 | B2 | 2/2002 | Von Borstel et al. | |
| 6,462,191 | B1 | 10/2002 | Lal | |
| 6,933,287 | B1 | 8/2005 | Greer | |
| 7,125,983 | B2 | 10/2006 | Iizuka et al. | |
| 7,135,464 | B2 | 11/2006 | Joshi-Hangal et al. | |
| 7,141,576 | B2 | 11/2006 | Lackey et al. | |
| 8,268,800 | B2 * | 9/2012 | Hamilton | C07H 19/04 514/49 |
| 8,324,180 | B2 | 12/2012 | Belyakov et al. | |
| 8,329,665 | B2 | 12/2012 | Belyakov et al. | |
| 8,329,666 | B2 | 12/2012 | Belyakov et al. | |
| 8,609,631 | B2 | 12/2013 | Belyakov et al. | |
| 8,618,075 | B2 * | 12/2013 | Hamilton | C07H 19/04 514/49 |
| 8,951,987 | B2 * | 2/2015 | Hamilton | C07H 19/04 514/49 |
| 9,040,501 | B2 | 5/2015 | Belyakov et al. | |

(Continued)

FOREIGN PATENT DOCUMENTS

| | | |
|---|---|---|
| EG | 1999020104 | 11/2010 |
| EP | 1 172 369 A1 | 1/2002 |

(Continued)

OTHER PUBLICATIONS

U.S. Appl. No. 14/088,465, filed Nov. 25, 2013; Office Action mailed Jun. 18, 2014.

U.S. Appl. No. 14/079,944, filed Nov. 14, 2013; Office Action mailed Oct. 8, 2014.

Aduma et al., "Anti-herpes virus activity of 5-methoxymethyl-2'-deoxycytidine in combination with deaminase inhibitors," Antiviral Chem. Chemother. 1(4):255-262 (1990).

Atallah et al., "Use of hypomethylating agents in myelodysplastic syndromes," Clin. Adv. Hematol. Oncol. 5(7):544-52 (2007).

(Continued)

*Primary Examiner* — Traviss C McIntosh, III

(74) *Attorney, Agent, or Firm* — Myers Bigel, P.A.

(57) ABSTRACT

The present invention provides certain tetrahydrouridine derivative compounds, pharmaceutical compositions and kits comprising such compounds, and methods of making and using such compounds.

9 Claims, 17 Drawing Sheets

(56) References Cited

U.S. PATENT DOCUMENTS

| | | | |
|---|---|---|---|
| 2003/0225029 | A1 | 12/2003 | Stuyver |
| 2004/0063926 | A1 | 4/2004 | Iizuka et al. |
| 2009/0099105 | A1 | 4/2009 | Wedekind et al. |
| 2009/0137521 | A1 | 5/2009 | Hamilton et al. |
| 2009/0325897 | A1 | 12/2009 | Greer |
| 2010/0279966 | A1 | 11/2010 | Belyakov et al. |
| 2010/0279967 | A1 | 11/2010 | Belyakov et al. |
| 2010/0279977 | A1 | 11/2010 | Belyakov et al. |
| 2012/0289475 | A1 | 11/2012 | Hamilton et al. |
| 2013/0116207 | A1 | 5/2013 | Belyakov et al. |
| 2014/0186335 | A1 | 7/2014 | Hamilton et al. |
| 2014/0221305 | A1 | 8/2014 | Belyakov et al. |

FOREIGN PATENT DOCUMENTS

| | | | |
|---|---|---|---|
| EP | 1 348 712 | A1 | 10/2003 |
| GB | 2136425 | A | 9/1984 |
| WO | WO 81/02164 | A1 | 8/1981 |
| WO | WO 85/01871 | A1 | 5/1985 |
| WO | WO 92/18517 | A1 | 10/1992 |
| WO | WO 94/26761 | A1 | 11/1994 |
| WO | WO 94/27632 | A1 | 12/1994 |
| WO | WO 96/26743 | A1 | 9/1996 |
| WO | WO 96/40165 | A1 | 12/1996 |
| WO | WO 00/51639 | A2 | 9/2000 |
| WO | WO 02/094844 | A2 | 11/2002 |
| WO | WO 03/012051 | A2 | 2/2003 |
| WO | WO 2004/028454 | A2 | 4/2004 |
| WO | WO 2004/041203 | A2 | 5/2004 |
| WO | WO 2005/115410 | A2 | 12/2005 |
| WO | WO 2006/015346 | A1 | 2/2006 |
| WO | WO 2006/063105 | A1 | 6/2006 |
| WO | WO 2008/085611 | A2 | 7/2008 |
| WO | WO 2009/021551 | A1 | 2/2009 |
| WO | WO 2009/052287 | A1 | 4/2009 |
| WO | WO 2010/047698 | A1 | 4/2010 |

OTHER PUBLICATIONS

Avramis et al., "Pharmacology of combination chemotherapy of cytosine arabinoside (Ara-C) and uracil arabinoside (Ara-U) or tetrahydrouridine (THU) against murine leukemia L1210/0 in tumor-bearing mice," Cancer Invest. 5:293-99 (1987).

Bellmunt et al., "Phase I-II study of paclitaxel, cisplatin, and gemcitabine in advanced transitional-cell carcinoma of the urothelium," J. Clin. Oncol. 18(18):3247-55 (2000).

Bendell et al., "Phase I dose-escalation study of tezacitabine in combination with 5-fluorouracil in patients with advanced solid tumors," Cancer 103(9):1925-31 (2005).

Beumer et al., "Concentrations of the DNA methyltransferase inhibitor 5-fluoro-2'-deoxycytidine (FdCyd) and its cytotoxic metabolites in plasma of patients treated with FdCyd and tetrahydrouridine (THU)," Cancer Chemother. Pharmacol. 62:363-68 (2008).

Beumer et al., "Modulation by tetrahydrouridine (THU) of gemcitabine (2',2'-difluoro-2'-deoxycycytidine, dFdC) pharmacokinetics, metabolism and bioavailability in mice," Abstract No. 1556, 2007 Amer. Assoc. Cancer Res. Annual Meeting, Los Angeles, CA (Apr. 14-18, 2007).

Beumer et al., "Modulation of gemcitabine (2',2'-difluoro-2'-deoxcycytidine) pharmacokinetics, metabolism, and bioavailability in mice by 3,4,5,6-tetrahydrouridine," Clin. Cancer Res. 14:3529-35 (2008).

Beumer et al., Pharmacokinetics, metabolism, and oral bioavailability of the DNA methyltransferase inhibitor 5-fluoro-2'-deoxycytidine in mice, Clin. Cancer Res. 12:7483-91 (2006).

Blum et al., "Phase I study of decitabine alone or in combination with valproic acid in acute myeloid leukemia," J. Clin. Oncol. 25(25):3884-91 (2007).

Bouffard et al., "Kinetic studies on 2',2'-difluorodeoxycytidine (gemcitabine) with purified human deoxycytidine kinase and cytidine deaminase," Biochem. Pharmacol. 45:1857-61 (1993).

Cacciamani et al., "Purification of Human Cytidine Deaminase: Molecular and Enzymatic Characterization and Inhibition by Synthetic Pyrimidine Analogs," Arch. Biochem. Biophys. 290(2):285-92 (1991).

Cantor et al., "Epigenetic modulation of endogenous tumor suppressor expression in lung cancer xenografts suppresses tumorigenicity," Int. J. Cancer 120:24-31 (2006).

Chabot et al., "Kinetics of deamination of 5-aza-2'-deoxycytidine and cytosine arabinoside by human liver cytidine deaminase and its inhibition by 3-deazauridine, thymidine or uracil arabinoside," Biochem. Pharmacol. 32(7):1327-28 (1983).

Chou et al., "Stereospecific Synthesis of 2-Deoxy-2,2-difluororibonolactone and Its Use in the Preparation of 2'-deoxy-2',2'-difluoro-β-D-ribofuranosyl Pyrimidine Nucleosides: The Key Role of selective Crystallization," Synthesis pp. 565-570 (Jun. 1992).

Choy, "Combination chemoradiotherapy with gemcitabine: Potential applications," Oncology, 14(74) (Suppl 4):20-25 (2000).

Cohen et al., "The Equilibrium of Hydrolytic Deamination of Cytidine and N-Methylcytidine," J. Biol. Chem 246(24):7566-68 (1971).

Cristalli et al., Diazepinone nucleosides as inhibitors of cytidine deaminase, Nucleosides Nucleotides 15:1567-80 (1996).

Desimone et al., "Tetrahydrouridine, cytidine analogs, and hemoglobin F," Am. J. Hematol. 18:283-88 (1985).

Dover et al., "5-Azacytidine increases HbF production and reduces anemia in sickle cell disease: dose-response analysis of subcutaneous and oral dosage regimens," Blood 66:527-32 (1985).

Dueñas-Gonzalez et al., "A phase II study of gemcitabine and cisplatin combination as induction chemotherapy for untreated locally advanced cervical carcinoma," Ann. Oncol. 12:541-47 (2001).

Eliopoulos et al., "Drug resistance to 5-aza-2'-deoxycytidine, 2',2'-difluorodeoxycytidine, and cytosine arabinoside conferred by retroviral-mediated transfer of human cytidine deaminase cDNA into murine cells." Cancer Chemother. Pharmacol. 42:373-78 (1998).

Fang et al., "A phase I and pharmacodynamic study of decitabine in combination with carboplatin in patients with recurrent, platinum-resistant, epithelial ovarian cancer," Cancer 116:4043-53 (2010).

Fenaux, "Inhibitors of DNA methylation: beyond myelodysplastic syndromes," Nature Clin. Pract. Oncol. 2:S36-S44 (2005).

Flaherty et al., "Dose escalation study of tezacitabine in combination with cisplatin in patients with advanced cancer," Cancer 97(8):1985-90 (2003).

Foss, "Nucleoside analogs and antimetabolite therapies for myelodysplastic syndrome," Best Pract. Res. Clin. Haematol. 17(4):573-84 (2004).

Gallardo et al., "A phase II study of gemcitabine in gallbladder carcinoma," Ann. Oncol. 12:1403-06 (2001).

Goodman and Gilman's "The Pharmacological Basis of Therapeutics," $10^{th}$ Ed., (Hardman, Limbird, eds.), McGraw-Hill, 1996, p. 54.

Gore, "Intravenous azacitidine for MDS," Clin. Adv. Hematol. Oncol. 5(3):234 (2007).

Gura, "Cancer models: Systems for identifying new drugs are often faulty," Science 278:1041-42 (1997).

Ho et al., "Clinical pharmacology of tetrahydrouridine," J. Clin. Pharmacol. 18:259-65 (1978).

Iliopoulos et al., "Inhibition of breast cancer cell growth in vitro and in vivo: Effect of restoration of wwox expression," Clin. Cancer Res. 13(1):268-74 (2007).

Isanbor et al., "Fluorine in medicinal chemistry: A review of anti-cancer agents," J. Fluorine Chem. 127:303-19 (2006).

Jansen et al., "The degradation of the antitumor agent gemcitabine hydrochloride in an acidic aqueous solution at pH 3.2 and identification of degradation products," J. Pharm. Sci. 89:885-891 (2000).

Kantarjian et al., "Decitabine improves patient outcomes in myelodysplastic syndromes," Cancer 106:1794-1803 (2006).

(56) References Cited

OTHER PUBLICATIONS

Kantarjian et al., "Results of decitabine (5-aza-2'deoxycytidine) therapy in 130 patients with chronic myelogenous leukemia," Cancer 98:522-28 (2003).
Kararli, "Comparison of the Gastrointestinal Anatomy, Physiology, and Biochemistry of Humans and Commonly Used Laboratory Animals," Biopharm. Drug Disposition 16:351-80 (1995).
Kees et al., "Development of resistance to 1-β-D-Arabinofuranosylcytosine after High-Dose Treatment in Childhood Lymphoblastic Leukemia: Analysis of resistance Mechanism in Established Cell Lines," Cancer Res. 49:3015-19 (1989).
Kelley et al., "Furanose-pyranose isomerization of reduced pyrimidine and cyclic urea ribosides," J. Med. Chem. 29:2351-58 (1986).
Kim et al., "Synthesis of Pyrimidin-2-one Nucleosides as Acid-Stable inhibitors of Cytidine Deaminase." J. Med. Chem. 29:1374-80 (1986).
Kondo et al., "Characteristics of the Gastric pH Profiles of Unfed and Fed Cynomolgus Monkeys as Pharmaceutical Product Development Subjects," Biopharm. Drug Disposition. 24:45-51 (2003).
Kreis et al., "Combinations of Tetrahydrouridine and Cytosine Arabinoside in Mouse Tumors," Cancer Treat. Rep. 61:1355-64 (1977).
Kreis et al., "Effect of tetrahydrouridine on the clinical pharmacology of 1-β-D-arabinofuranosylcytosine when both drugs are coinfused over three hours," Cancer Res. 48:1337-42 (1988).
Kreis et al., "Tetrahydrouridine: physiologic disposition and effect upon deamination of cytosine arabinoside in man," Cancer Treatment Rep. 61:1347-53 (1977).
Kreis et al., Therapy of refractory/relapsed acute leukemia with cytosine arabinoside plus tetrahydrouridine (an inhibitor of cytidine deaminase)—a pilot study, Leukemia 5:991-98 (1991).
Laliberte et al., "Potent inhibitors for the deamination of cytosine arabinoside and 5-aza-2'-deoxycytidine by human cytidine deaminase", *Cancer Chemotherapy and Pharmacology*, vol. 30, 1992, pp. 7-11.
Lange et al., "Distinctive demography, biology, and outcome of acute myeloid leukemia and myelodysplastic syndrome in children With Down Syndrome: Children's cancer group studies 2861 and 2891," Blood 91:608-15 (1998).
Lemaire et al., "Enhancement of antineoplastic action of 5-aza-2'-deoxycytidine by zebularine on L1210 leukemia," Anticancer Drugs 16:301-08 (2005).
Lemaire et al., "Inhibition of cytidine deaminase by zebularine enhances the antineoplastic action of 5-aza-2'-deoxycytidine", *Cancer Chemotherapy Pharmacology*, vol. 63, No. 3, (2009), pp. 411-416; Published online, Apr. 9, 2008.
Liu P.S. et al., "Cyclic Urea Nucleosides. Cytidine Deaminase Activity as a Function of Aglycon Ring Size", *Journal of Medicinal Chemistry*, vol. 24, No. 6, 1981, pp. 662-666.
Lübbert et al., "Efficacy of a 3-day, low-dose treatment with 5-azacytidine followed by donor lymphocyte infusions in older patients with acute myeloid leukemia or chronic myelomonocytic leukemia relapsed after allografting," Bone Marrow Transpl. 45:627-32 (2010).
Ludek Olaf R. et al., "Synthesis of conformationally locked carbocyclic 1,3-diazepinone nucleosides as inhibitors of cytidine deaminase", *Nucleic Acids Symposium Series*, No. 52, 2008, pp. 659-660.
Makhija et al., "Results from a phase II randomized, placebo-controlled, double-blind trial suggest improved PFS with the addition of pertuzumab to gemcitabine in patients with platinum-resistant ovarian, fallopian tube, or primary peritoneal cancer," J. Clin. Oncol. 25(18S):275 s Abstract 5507 (2007).
Marquez et al., "1,3-Diazepinones. 1. Synthesis of 5-Hydroxyperhydro-1,3-diazepin-2-one." J. Organic Chem. 45:485-89 (1980).
Marquez V. E. et al., "Synthesis of 1,3-Diazepin-2-one Nucleosides as Transition-State Inhibitors of Cytidine Deaminase", *Journal of Medicinal Chemistry*, vol. 23, No. 7, Jul. 1980, pp. 713-715.
Marsh et al., Therapy of refractory/relapsed acute myeloid leukemia and blast crisis of chronic myeloid leukemia with the combination of cytosine arabinoside, tetrahydrouridine, and carboplatin, Cancer Chemther. Pharmacol. 31:481-84 (1993).
Missiaglia et al., "Growth delay of human pancreatic cancer cells by methylase inhibitor 5-aza-2'-deoxycytidine treatment is associated with activation of the interferon signalling pathway," Oncogene 24:199-211 (2005).
Miwa et al., "High susceptibility of human cancer xenografts with higher levels of cytidine deaminase to a 2'-deoxycytidine antimetabolite, 2'-deoxy-2'-methylidenecytidine," Clin. Cancer Res. 4:493-497 (1998).
Momparler et al., "Epigenetic therapy of cancer with 5-aza-2'-deoxycytidine (decitabine)," Semin. Oncol. 32:443-51 (2005).
Momparler et al., "Induction of cytidine deaminase in HL-60 myeloid leukemic cells by 5-aza-2'-deoxycytidine," Leukemia Res. 14:751-54 (1990).
Neil et al., Enhancement by tetrahydrouridine (NSC-112907) of the oral activity of 5-azacytidine (NSC-102816) in L1210 leukemic mice, Cancer Chemother. Rep. Part 1 59:459-65 (1975).
Neil et al., "Enhancement by tetrahydrouridine of 1-β-D-arabinofuranosylcytosine (cytarabine) oral activity in L1210 leukemic mice," Cancer Res. 30:2166-72 (1970).
Norton et al., "Synthesis of Deoxytetrahydrouridine," J. Organic Chem. 74:2221-23 (2009).
Penz et al., "Phase II trial of two-weekly gemcitabine in patients with advanced biliary tract cancer," Ann. Oncol. 12:183-86 (2001).
Rizzieri et al., "Phase I evaluation of prolonged-infusion gemcitabine with mitoxantrone for relapsed or refractory acute leukemia," J. Clin. Oncol. 20(3):674-79 (2002).
Rodriguez et al., "Phase I clinical trials of tezacitabine [(E)-2'-deoxy-2'-(fluoromethylene)cytidine] in patients with refractory solid tumors", Clin. Cancer Res. 8:2828-34 (2002).
Scaife et al., (2008) *Antimetabolites in Cancer Therapy*, In *Anticancer Therapeutics*, John Wiley & Sons, Ltd., pp. 91-110.
Shao et al., "Ribonucleotide reductase inhibitors and future drug design," Curr. Cancer Drug Targets 6:409-31 (2006).
Soriano et al., "Safety and clinical activity of the combination of 5-azacytidine, valproic acid, and all-*trans* retinoic acid in acute myeloid leukemia and myelodysplastic syndrome," Blood 110:2302-08 (2007).
Szafraniec et al., "New nucleoside analogs in the treatment of hematological disorders," Acta Poloniae Pharmaceutica—Drug Res. 61(3):223-32 (2004).
Thaler et al., "Comparative analysis of two consecutive phase II studies with IFN-α and IFN-α + ara-C in untreated chronic-phase CML patients," Bone Marrow Transpl. 17(Suppl 3):S25-S28 (1996).
Tsavaris et al., "Weekly gemcitabine for the treatment of biliary tract and gallbladder cancer," Invest. New Drugs 22:193-98 (2004).
Van Cutsem et al., "Phase III trial of gemcitabine plus tipifarnib compared with gemcitabine plus placebo in advanced pancreatic cancer," J. Clin. Oncol. 22(8):1430-38 (2004).
Vincenzetti et al., "Recombinant Human Cytidine Deaminase: Expression, Purification, and Characterization," Protein Expression Purification 8:247-53 (1996).
Watanabe et al., Nucleosides. 110. Synthesis and antiherpes virus activity of some 2'-fluoro-2'-deoxyarabinofuranosylpyrimidine nucleosides, J. Med. Chem. 22:21-24 (1979).
Wentworth et al., "Cytidine deaminases (from *Escherichia coli* and human liver)," Meth. Enzymol. 51:401-7 (1978).
Wisdom et al., "Cytidine Aminohydrolase from Sheep Liver," Proc. Biochem. Soc., 471st Meeting , CIBA Laboratories, Ltd., Horsham, May 20, 1967, 7P.
Wong et al., "Phase I evaluation of tetrahythouridine combined with cytosine arabinoside," Cancer Treatment Rep. 63:1245-49 (1979).
Yang et al., "Phase II study of gemcitabine in patients with advanced hepatocellular carcinoma", Cancer 89(4):750-56 (2000).
U.S. Appl. No. 12/252,961, filed Oct. 16, 2008; Office Action mailed Jun. 8, 2011.
U.S. Appl. No. 13/556,404, filed Jul. 24, 2012; Office Action mailed Nov. 7, 2012.

(56) References Cited

OTHER PUBLICATIONS

U.S. Appl. No. 13/556,404, filed Jul. 24, 2012; Office Action mailed May 22, 2013.
U.S. Appl. No. 12/755,106, filed Apr. 6, 2010; Office Action mailed Sep. 29, 2011.
U.S. Appl. No. 12/755,106, filed Apr. 6, 2010; Office Action mailed Mar. 28, 2012.
U.S. Appl. No. 12/755,116, filed Apr. 6, 2010; Office Action mailed Oct. 5, 2011.
U.S. Appl. No. 12/755,116, filed Apr. 6, 2010; Office Action mailed Mar. 28, 2012.
U.S. Appl. No. 12/755,122, filed Apr. 6, 2010; Office Action mailed Oct. 18, 2011.
U.S. Appl. No. 12/755,122, filed Apr. 6, 2010; Office Action mailed Mar. 30, 2012.
U.S. Appl. No. 13/665,184, filed Oct. 31, 2012; Office Action mailed Apr. 9, 2013.
U.S. Appl. No. 14/079,944, filed Nov. 14, 2013; Office Action mailed Jun. 16, 2014.
International Search Report Corresponding to International Application No. PCT/US2008/080163; Date of Mailing: Feb. 11, 2009; 6 pages.
Chile Application No. 378-10, filed Apr. 16, 2010, Office Action mailed May 8, 2013.
Chinese Application No. 200880111719.5, filed Oct. 16, 2008; Office Action mailed Jan. 31, 2012.
Colombian Application No. 10057462, filed Oct. 16, 2008, Opposition filed Aug. 5, 2011.
Eurasian Application No. 201000642, filed Oct. 16, 2008, Office Action mailed Oct. 3, 2011.
Eurasian Application No. 201000642, filed Oct. 16, 2008, Office Action mailed Mar. 23, 2012.
Eurasian Application No. 201000642, filed Oct. 16, 2008, Office Action mailed Oct. 16, 2012.
European Application No. 12151552.2, filed Jan. 18, 2012, extended European search report mailed Mar. 30, 2012.
Pakistan Application No. 1206/2008, filed Oct. 16, 2008, Office Action mailed Jun. 16, 2009.
International Search Report Corresponding to International Application No. PCT/US2010/030073; Date of Mailing: May 20, 2010; 5 pages.
International Search Report Corresponding to International Application No. PCT/US2010/030081; Date of Mailing: Sep. 7, 2010; 5 pages.
International Search Report Corresponding to International Application No. PCT/US2010/030078; Date of Mailing: Sep. 7, 2010; 5 pages.
Chung et al. "Structure of Human Cytidine Deaminase Bound to a Potent Inhibitor", *J. Med. Chem.* 48:658-660 (2005).
Henze "Nucleic Acids.IV. The Catalytic Reduction of Pyrimidine Nucleosides (Human Liver Deaminase Inhibitors)", *J. Am. Chem. Soc.* 89(25):6720-6725 (1967).

* cited by examiner

CERTAIN COMPOUNDS, COMPOSITIONS AND METHODS

This application is a continuation of U.S. application Ser. No. 14/088,465, filed Nov. 25, 2013, which is a continuation of U.S. application Ser. No. 13/556,404, filed Jul. 24, 2012, now U.S. Pat. No. 8,618,075, which is a continuation of U.S. application Ser. No. 12/252,961, filed Oct. 16, 2008, now U.S. Pat. No. 8,268,800, which claims the benefit of U.S. Provisional Application No. 60/980,397, filed Oct. 16, 2007, the entire contents of each of which is hereby incorporated by reference.

FIELD OF THE INVENTION

The present invention provides certain tetrahydrouridine derivative compounds which are inhibitors of the enzyme cytidine deaminase, pharmaceutical compositions and kits comprising such compounds, and methods of making and using such compounds.

BACKGROUND

The enzymes adenosine deaminase (ADA, EC 3.5.4.4) and cytidine deaminase (CDA, EC 3.5.4.5) function to deaminate natural aminopurine and aminopyrimidine nucleosides, respectively, in human and other organisms. They may also convert active nucleoside-based drugs into inactive metabolites. For example, the purine nucleoside drug arabinosyladenine (fludarabine, ara-A) is deaminated by ADA; the resulting compound, with the parent amino group replaced with hydroxyl, is inactive as an antitumor agent compared to the parent compound. Similarly, the antileukemia drug arabinosylcytosine (cytarabine, ara-C) is metabolically degraded by CDA into inactive arabinosyluracil.

CDA is a component of the pyrimidine salvage pathway. It converts cytidine and deoxycytidine to uridine and deoxyuridine, respectively, by hydrolytic deamination (*Arch. Biochem. Biophys.* 1991, 290, 285-292; *Methods Enzymol.* 1978, 51, 401-407; *Biochem. J.* 1967, 104, 7P). It also deaminates a number of synthetic cytosine analogs which are clinically useful drugs, such as ara-C mentioned above (*Cancer Chemother. Pharmacol.* 1998, 42, 373-378; *Cancer Res.* 1989, 49, 3015-3019; *Antiviral Chem. Chemother.* 1990, 1, 255-262). Conversion of the cytosine compounds to the uridine derivatives usually confers loss of therapeutic activity or addition of side-effects. It has also been shown that cancers that acquire resistance to cytosine analog drugs often overexpress CDA (*Leuk. Res.* 1990, 14, 751-754). Leukemic cells expressing a high level of CDA can manifest resistance to cytosine antimetabolites and thereby limit the antineoplastic activity of such therapeutics (*Biochem. Pharmacol.* 1993, 45, 1857-1861). Inhibitors of CDA could therefore be useful adjuvants in combination chemotherapy.

Tetrahydrouridine (THU) has been known as an inhibitor of cytidine deaminase for a number of years.

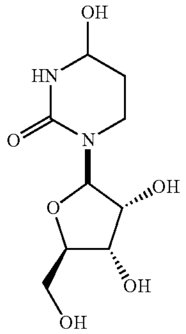

Tetrahydrouridine
(THU)

Various reports have suggested that co-administration with THU increases the efficacy and oral activity of cytidine-based drugs. For example, THU has been shown to enhance the oral activity of anti-leukemic agent 5-azacytidine in L1210 leukemic mice (*Cancer Chemotherapy Reports* 1975, 59, 459-465). The combination of THU plus 5-azacytidine has also been studied in a baboon sickle cell anemia model (*Am. J. Hematol.* 1985, 18, 283-288), and in human patients with sickle cell anemia in combination with orally administered 5-azacytidine (*Blood* 1985, 66, 527-532).

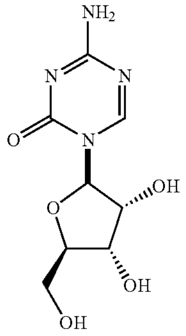

5-azacytidine

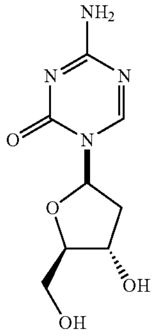

5-aza-2′-deoxycytidine
(decitabine)

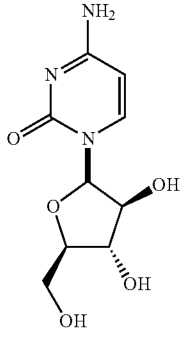

ara-C

THU has also been shown to enhance the oral efficacy of ara-C in L1210 leukemic mice (*Cancer Research* 1970, 30, 2166; *Cancer Invest* 1987, 5, (4), 293-9), and in tumor-bearing mice (*Cancer Treat. Rep.* 1977, 61, 1355-1364). The combination of intravenously-administered ara-C with intravenously-administered THU has been investigated in several clinical studies in humans (*Cancer Treat. Rep.* 1977, 61, 1347-1353; *Cancer Treat. Rep.* 1979, 63, 1245-1249; *Cancer Res.* 1988, 48, 1337-1342). In particular, combination studies in patients with acute myeloid leukemia (AML) and chronic myeloid leukemia (CML) have been performed (*Leukemia* 1991, 5, 991-998; *Cancer Chemother. Pharmacol.* 1993, 31, 481-484).

5-Aza-2'-deoxycytidine (decitabine) is an antineoplastic agent for the treatment of myelodysplastic syndrome (MDS), with potential utility for the treatment of AML and CML as well. Like the other cytidine-based drugs, its oral bioavailability and efficacy are limited by deactivation by CDA. THU has been shown to improve the potency of decitabine in a sickle cell disease model in baboons (*Am. J. Hematol.* 1985, 18, 283-288). In addition, another known CDA inhibitor, zebularine, has been shown to enhance the efficacy of decitabine in mice with L1210 leukemia (*Anticancer Drugs* 2005, 16, 301-308).

Gemcitabine, another cytidine-based antineoplastic drug, has also been studied in conjunction with CDA inhibitors (*Biochem. Pharmacol.* 1993, 45, 1857-1861). Co-administration with THU has been shown to alter the pharmacokinetics and bioavailability of gemcitabine in mice (Abstr. 1556, 2007 AACR Annual Meeting, Apr. 14-18, 2007, Los Angeles, Calif.; *Clin. Cancer Res.* 2008, 14, 3529-3535).

5-Fluoro-2'-deoxycytidine (fluorocytidine, FdCyd) is another cytidine-based anticancer drug which is an inhibitor of DNA methyltransferase. The modulation of its metabolism and pharmacokinetics by THU in mice has been studied (*Clin Cancer Res.,* 2006, 12, 7483-7491; *Cancer Chemother. Pharm.* 2008, 62, 363-368).

The results of the aforementioned studies suggest that there is therapeutic utility in the administration of CDA inhibitors together with cytidine-based drugs such as ara-C, decitabine, 5-azacytidine and others. However, early CDA inhibitors such as THU suffer from drawbacks that include acid instability (*J. Med. Chem.* 1986, 29, 2351) and poor bioavailability (*J. Clin. Pharmacol.* 1978, 18, 259).

There is therefore an ongoing need for new, potent and therapeutically useful inhibitors of CDA.

BRIEF SUMMARY OF THE INVENTION

The present invention provides certain tetrahydrouridine derivative compounds, pharmaceutical compositions and kits comprising such compounds, and methods of making and using such compounds. The compounds, compositions, kits and methods of the invention may provide certain benefits. For example, the compounds and compositions of the invention may inhibit CDA enzyme activity and/or enhance the half-life, bioavailability and/or efficacy of drugs that are substrates for CDA. Additionally, the compounds, compositions, kits and methods of the invention may exhibit improved aqueous solubility, chemical stability, drug absorption levels, toxicity levels, shelf-life, reproducibility in manufacturing and formulation, and therapeutic efficacy.

In one embodiment, the invention provides a compound of Formula I:

I

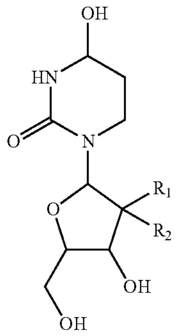

or a pharmaceutically acceptable salt of the compound, wherein:

$R_1$ and $R_2$ are independently selected from the group consisting of hydrogen, halo, cyano, nitro, sulfhydryl, hydroxyl, formyl, carboxyl, COO($C_1$ to $C_6$ straight or branched chain alkyl), COO($C_1$ to $C_6$ straight or branched chain alkenyl), COO($C_1$ to $C_6$ straight or branched chain alkynyl), CO($C_1$ to $C_6$ straight or branched chain alkyl), CO($C_1$ to $C_6$ straight or branched chain alkenyl), CO($C_1$ to $C_6$ straight or branched chain alkynyl), $C_1$ to $C_6$ straight or branched chain alkyl, $C_1$ to $C_6$ straight or branched chain alkenyl, $C_1$ to $C_6$ straight or branched chain alkynyl, $C_1$ to $C_6$ straight or branched chain alkoxy, and $C_1$ to $C_6$ straight or branched chain alkenoxy; wherein each occurrence of $C_1$ to $C_6$ straight or branched chain alkyl, $C_1$ to $C_6$ straight or branched chain alkenyl, $C_1$ to $C_6$ straight or branched chain alkynyl, $C_1$ to $C_6$ straight or branched chain alkoxy, or $C_1$ to $C_6$ straight or branched chain alkenoxy may be independently unsubstituted or substituted with one to four substituents independently selected from the group consisting of halo, hydroxyl, cyano, nitro, formyl, carboxyl, and sulfhydryl;

and provided that when one of $R_1$ and $R_2$ is —H, then the other is not —H, —OH or —$CH_2OH$.

In some embodiments, $R_1$ and $R_2$ are independently selected from the group consisting of hydrogen, halo, hydroxyl, cyano, nitro, sulfhydryl, $C_1$ to $C_6$ straight or branched chain alkyl, $C_1$ to $C_6$ straight or branched chain alkenyl, $C_1$ to $C_6$ straight or branched chain alkynyl, $C_1$ to $C_6$ straight or branched chain alkoxy, and $C_1$ to $C_6$ straight or branched chain alkenoxy; wherein each occurrence of $C_1$ to $C_6$ straight or branched chain alkyl, $C_1$ to $C_6$ straight or branched chain alkenyl, $C_1$ to $C_6$ straight or branched chain alkynyl, $C_1$ to $C_6$ straight or branched chain alkoxy, or $C_1$ to $C_6$ straight or branched chain alkenoxy may be independently unsubstituted or substituted with one ore more halos;

and provided that when one of $R_1$ and $R_2$ is —H, then the other is not —H, or —OH.

In some embodiments, $R_1$ and $R_2$ are independently selected from the group consisting of hydrogen, halo, $C_1$ to $C_6$ alkyl, $C_1$ to $C_6$ alkenyl, $C_1$ to $C_6$ alkoxy, and $C_1$ to $C_6$ alkenoxy; wherein each occurrence of $C_1$ to $C_6$ straight or branched chain alkyl, $C_1$ to $C_6$ straight or branched chain alkenyl, $C_1$ to $C_6$ straight or branched chain alkoxy and $C_1$ to $C_6$ straight or branched chain alkenoxy may be independently unsubstituted or substituted with one to three halos;

and provided that when one of $R_1$ and $R_2$ is —H, then the other is not —H, or —OH.

In some embodiments, the compound of Formula is:

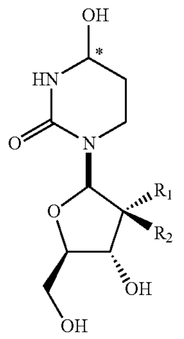

wherein the carbon marked by an asterisk may have an (R) or an (S) configuration. In some embodiments, a disclosed pharmaceutical composition or method of use may comprise a compound with an (R) configuration an (S) configuration, or a mixture of (R) and (S) configurations. In some embodiments, $R_1$ and $R_2$ are independently selected from fluoro and hydrogen, with the proviso that $R_1$ and $R_2$ may not both be hydrogen.

In further embodiments, the compound of Formula I has the stereochemistry of either Ia or Ib:

Ia

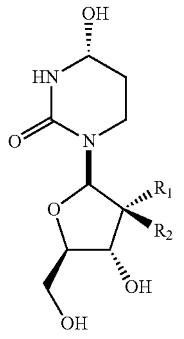

Ib

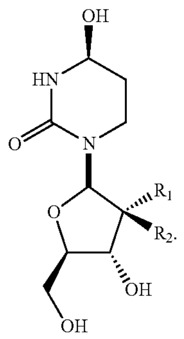

In some embodiments, $R_1$ and $R_2$ are independently selected from fluoro and hydrogen, with the proviso that $R_1$ and $R_2$ may not both be hydrogen.

In further embodiments, the compound of Formula I is selected from the group consisting of Compounds 1 to 23 and pharmaceutically acceptable salts thereof:

Compound 1

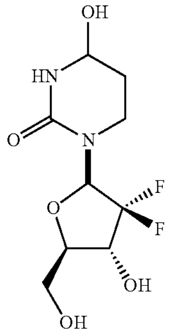

Compound 2

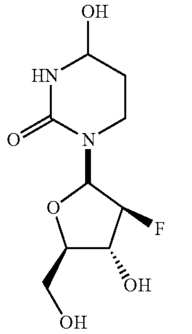

Compound 3

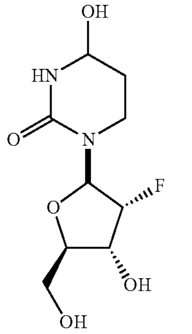

Compound 4

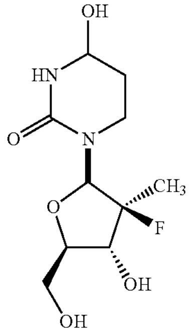

Compound 5

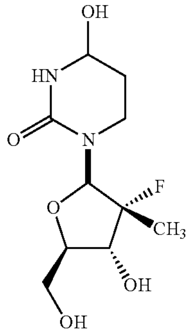

-continued
Compound 6
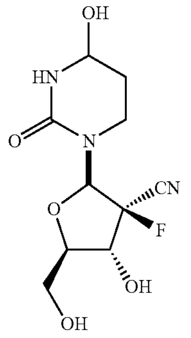
Compound 7
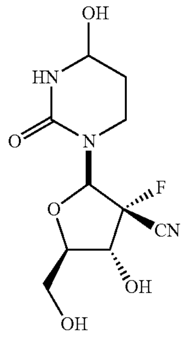
Compound 8
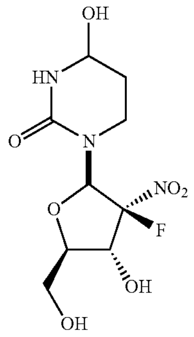
Compound 9
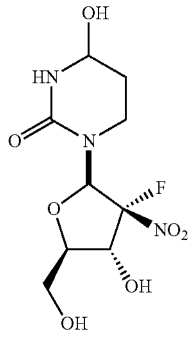
-continued
Compound 10
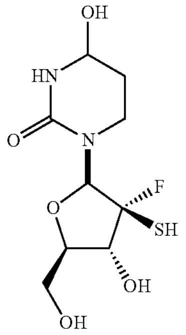
Compound 11
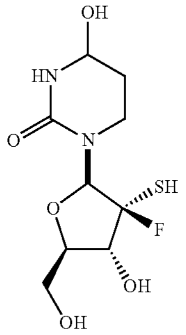
Compound 12
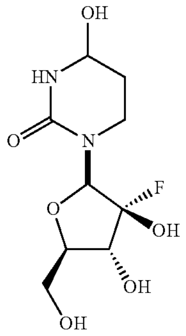
Compound 13
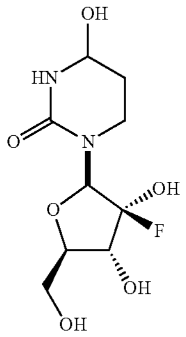

-continued
Compound 14
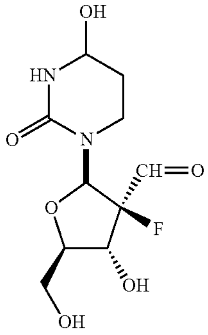
Compound 15
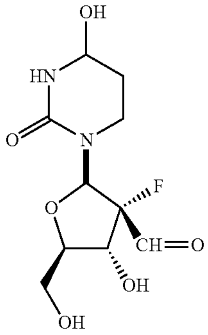
Compound 16
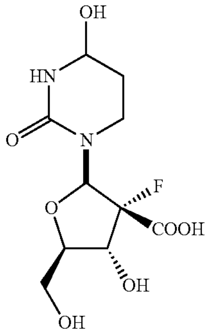
Compound 17
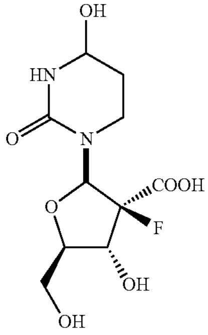
-continued
Compound 18
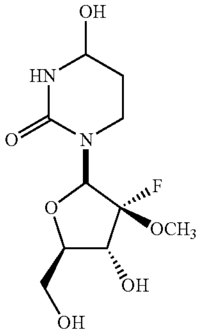
Compound 19
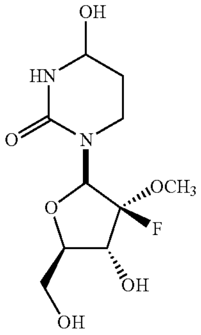
Compound 20
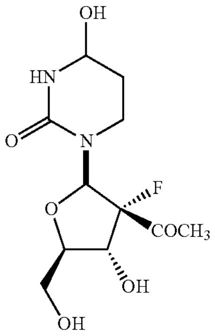
Compound 21
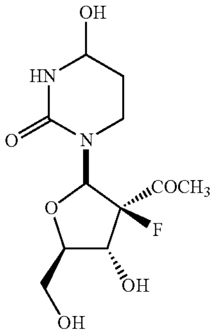

-continued

Compound 22

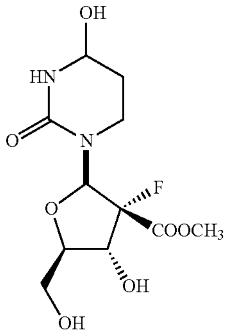

Compound 23

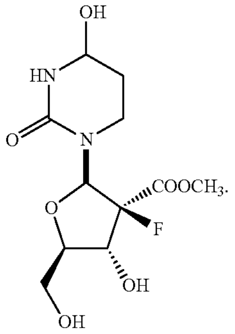

In further embodiments, the compound of Formula I is selected from the group consisting of Compounds 1a, 1b, 2a, 2b, 3a, and 3b, and pharmaceutically acceptable salts thereof.

Compound 1a

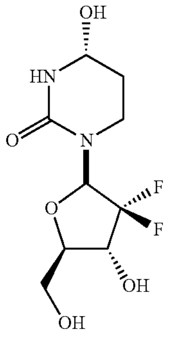

Compound 1b

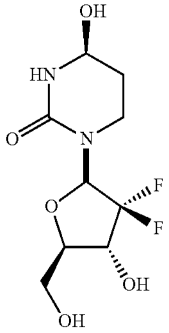

-continued

Compound 2a

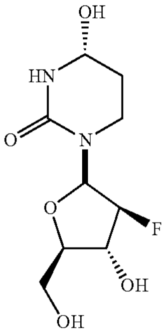

Compound 2b

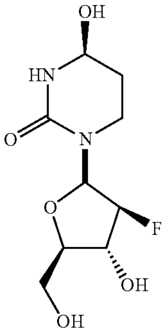

Compound 3a

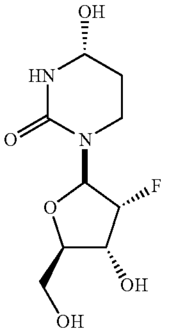

Compound 3b

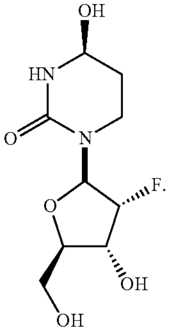

Since the compounds of the invention may possess at least one chiral center, they may exist in the form of enantiomers, diastereomers, racemic mixtures, non-racemic mixtures or other stereoisomers. The present invention encompasses all such possible isomers, as well as geometric isomers and tautomers.

Another aspect of the present invention relates to a pharmaceutical composition comprising:

(i) an effective amount of a compound of the invention as described herein, including but not limited to each express embodiment; and (ii) a pharmaceutically acceptable excipient.

In further embodiments, the pharmaceutical composition further comprises an effective amount of at least one additional therapeutic agent, such as a CDA substrate drug or chemotherapeutic agent.

The "effective amount" of the compound of the invention may vary from 0.1 wt. % to about 100 wt. %. In some embodiments, the effective amount of the compound is 0.1 to 20% w/w. In other embodiments, the effective amount is 1-10% w/w. In yet other embodiments, the effective amount is 2-5% w/w.

The pharmaceutical compositions of the invention may be formulated for administration in solid or liquid form, including those adapted for the following: (1) oral administration, for example, drenches (for example, aqueous or non-aqueous solutions or suspensions), tablets (for example, those targeted for buccal, sublingual and systemic absorption), caplets, boluses, powders, granules, pastes for application to the tongue, hard gelatin capsules, soft gelatin capsules, mouth sprays, troches, lozenges, pellets, syrups, suspensions, elixirs, liquids, emulsions and microemulsions; (2) parenteral administration, for example, by subcutaneous, intramuscular, intravenous or epidural injection as, for example, a sterile solution or suspension; (3) topical application, for example, as a cream, ointment, patch, pad or spray applied to the skin; (4) intravaginally or intrarectally, for example, as a pessary, cream or foam; (5) sublingually; (6) ocularly; (7) transdermally; or (8) nasally. The pharmaceutical compositions may be formulated for immediate, sustained or controlled release.

In some embodiments, the pharmaceutical compositions are formulated for oral administration. In further embodiments, the pharmaceutical compositions are formulated for oral administration in solid form.

Another embodiment of the present invention relates to a method for inhibiting cytidine deaminase, comprising administering to a subject in need thereof an effective amount of a compound or pharmaceutical composition of the invention as described herein, including but not limited to each express embodiment.

In some embodiments, the subject is a mammal. In further embodiments, the subject is a human.

Another embodiment of the present invention relates to a method for treating cancer, comprising administering to a subject in need thereof:

(i) an effective amount of a compound or pharmaceutical composition of the invention as described herein, including but not limited to each express embodiment; and (ii) a CDA substrate drug, including but not limited to each express embodiment described herein.

In some embodiments, the subject is a mammal. In further embodiments, the subject is a human.

In some embodiments, the cancer is selected from hematological cancers and solid cancers. In further embodiments, the hematological cancer selected from MDS and leukemia. In further embodiments, the solid cancer is selected from pancreatic cancer, ovarian cancer, peritoneal cancer, non small cell lung cancer, and breast cancer. In yet further embodiments, the leukemia is acute myeloid leukemia (AML) or chronic myeloid leukemia (CML).

Another embodiment of the present invention relates to a method for inhibiting degradation of a CDA substrate drug by cytidine deaminase, comprising administering an effective amount of a compound or pharmaceutical composition of the invention as described herein, including but not limited to each express embodiment, to a subject that is undergoing treatment with the CDA substrate drug. The CDA substrate drug, including but not limited to each express embodiment described herein.

In some embodiments, the subject is a mammal. In further embodiments, the subject is a human.

Another embodiment of the present invention relates to a kit comprising at least one unit dosage form, which unit dosage form comprises a compound or pharmaceutical composition of the invention.

The kit may further comprise a container and/or a package suitable for commercial sale. The container can be in any conventional shape or form as known in the art which is made of a pharmaceutically acceptable material, such as a paper or cardboard box, a glass or plastic bottle or jar, a re-sealable bag, or a blister pack with individual dosages for pressing out of the pack according to a therapeutic schedule. More than one container can be used together in a single package. For example, tablets may be contained in a blister pack which is in turn contained within a box.

BRIEF DESCRIPTION OF THE DRAWINGS

FIG. 9 is an ORTEP plot of the crystal structure of Compound 1a.

RETAILED DESCRIPTION OF THE INVENTION

Figure 1:
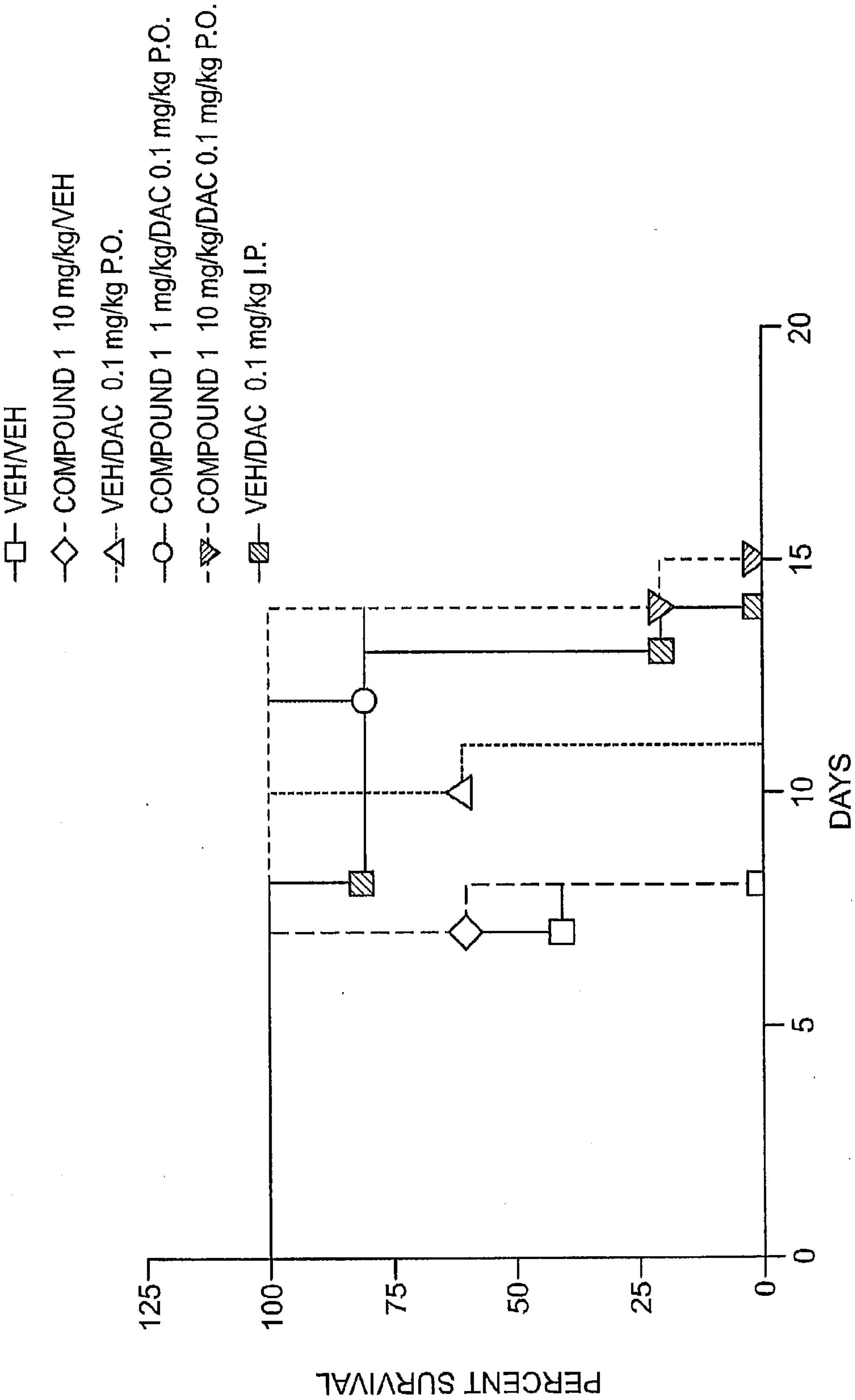
FIG. 1 is a graph that shows the effect of Compound 1 on decitabine induced survival in the L1210 mouse lymphoma model.

The present invention provides certain tetrahydrouridine derivative compounds, pharmaceutical compositions and kits comprising such compounds, and methods of making and using such compounds. The compounds, compositions, kits and methods of the invention may provide certain benefits. For example, the compounds and compositions of the invention may inhibit CDA enzyme activity and/or enhance the half-life, bioavailability and/or efficacy of drugs that are substrates for CDA. Additionally, the compounds, compositions, kits and methods of the invention may exhibit improved aqueous solubility, chemical stability, drug absorption levels, toxicity levels, shelf-life, reproducibility in manufacturing and formulation, and therapeutic efficacy.

DEFINITIONS

Throughout the specification and claims, the following definitions apply.

As used in the specification and claims, the singular forms “a,” “an,” and “the” include plural referents unless the content clearly dictates otherwise. Thus, for example, reference to a pharmaceutical composition comprising “a compound” may encompass two or more compounds.

“Alkyl” refers to a saturated straight or branched chain hydrocarbon radical. Examples include without limitation methyl, ethyl, propyl, iso-propyl, butyl, iso-butyl, tert-butyl, n-pentyl and n-hexyl. In some embodiments, the alkyl chain is a $C_1$ to $C_6$ branched or unbranched carbon chain. In some embodiments, the alkyl chain is a $C_2$ to $C_5$ branched or unbranched carbon chain. In some embodiments, the alkyl chain is a $C_1$ to $C_4$ branched or unbranched carbon chain. In some embodiments, the alkyl chain is a $C_2$ to $C_4$ branched or unbranched carbon chain. In some embodiments, the alkyl chain is a $C_3$ to $C_5$ branched or unbranched carbon chain. In some embodiments, the alkyl chain is a $C_1$ to $C_2$ branched or unbranched carbon chain. In some embodiments, the alkyl chain is a $C_2$ to $C_3$ branched or unbranched carbon chain.

“Alkenyl” refers to an unsaturated straight or branched chain hydrocarbon radical comprising at least one carbon to carbon double bond. Examples include without limitation ethenyl, propenyl, iso-propenyl, butenyl, iso-butenyl, tert-butenyl, n-pentenyl and n-hexenyl. In some embodiments, the alkenyl chain is a $C_2$ to $C_6$ branched or unbranched carbon chain. In some embodiments, the alkenyl chain is a $C_2$ to $C_5$ branched or unbranched carbon chain. In some embodiments, the alkenyl chain is a $C_2$ to $C_4$ branched or unbranched carbon chain. In some embodiments, the alkenyl chain is a $C_3$ to $C_5$ branched or unbranched carbon chain.

“Alkoxy” refers to an alkyl group bonded through an oxygen linkage.

“Alkenoxy” refers to an alkenyl group bonded through an oxygen linkage.

“Cycloalkyl” refers to a non-aromatic cyclic alkyl radical.

“Cycloalkenyl” refers to a non-aromatic cyclic alkenyl radical.

“Halo” refers to a fluoro, chloro, bromo or iodo radical.

“Substituted” means that at least one hydrogen on a designated group is replaced with another radical, provided that the designated group’s normal valence is not exceeded. With respect to any group containing one or more substituents, such groups are not intended to introduce any substitution that is sterically impractical, synthetically non-feasible and/or inherently unstable.

“CDA substrate drug” refers to a drug that can be deaminated by CDA. Nonlimiting examples of a CDA substrate include cytidine analogs, such as decitabine, 5-azacytidine, gemcitabine, ara-C, troxacitabine, tezacitabine, 5'-fluoro-2'-deoxycytidine, and cytochlor.

“Effective amount” refers to the amount required to produce a desired effect (e.g., enhancing the half-life, bioavailability or efficacy of a CDA substrate drug, treating cancer in a subject, inhibiting cytidine deaminase in a subject, or inhibiting degradation of a CDA substrate drug by cytidine deaminase).

“Half-life” refers to the period of time required for the concentration or amount of a compound in a subject to be reduced to exactly one-half of a given concentration or amount.

“Pharmaceutically acceptable” refers to those properties and/or substances that are acceptable to the patient from a pharmacological and/or toxicological point of view, and/or to the manufacturing pharmaceutical chemist from a physical and/or chemical point of view regarding composition, formulation, stability, patient acceptance, bioavailability and compatibility with other ingredients.

“Pharmaceutically acceptable excipient” can mean any substance, not itself a therapeutic agent, used as a carrier, diluent, adjuvant, binder, and/or vehicle for delivery of a therapeutic agent to a subject, or added to a pharmaceutical composition to improve its handling or storage properties or to permit or facilitate formation of a compound or composition into a unit dosage form for administration. Pharmaceutically acceptable excipients are well known in the pharmaceutical arts and are described, for example, in Remington’s Pharmaceutical Sciences, Mack Publishing Co., Easton, Pa. (e.g., $20^{th}$ Ed., 2000), and Handbook of Pharmaceutical Excipients, American Pharmaceutical Association, Washington, D.C., (e.g., $1^{st}$, $2^{nd}$ and $3^{rd}$ Eds., 1986, 1994 and 2000, respectively). As will be known to those skilled in the art, excipients may provide a variety of functions and may be described as wetting agents, buffering agents, suspending agents, lubricating agents, emulsifiers, disintegrants, absorbents, preservatives, surfactants, colorants, flavorants, and sweeteners. Examples of pharmaceutically acceptable excipients include without limitation: (1) sugars, such as lactose, glucose and sucrose; (2) starches, such as corn starch and potato starch; (3) cellulose and its derivatives, such as sodium carboxymethyl cellulose, ethyl cellulose, cellulose acetate, hydroxypropylmethylcellulose, and hydroxypropylcellulose; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer’s solution; (19) ethyl alcohol; (20) pH buffered solutions; (21) polyesters, polycarbonates and/or polyanhydrides; and (22) other non-toxic compatible substances employed in pharmaceutical formulations.

“Pharmaceutically acceptable salt” refers to an acid or base salt of a compound of the invention, which salt possesses the desired pharmacological activity and is neither biologically nor otherwise undesirable. The salt can be formed with acids that include without limitation acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxyethane-sulfonate, lactate, maleate, methanesulfonate, 2-naphthalenesulfonate, nicotinate, oxalate, thiocyanate, tosylate and undecanoate. Examples of a base salt include without limitation ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. In some embodiments, the basic nitrogen-containing groups can be quarternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as phenethyl bromides.

"Unit dosage form" refers to a physically discrete unit suitable as a unitary dosage for human or other animal subjects. Each unit dosage form may contain a predetermined amount of an active substance (e.g., compound or composition of the invention, CDA substrate drug and/or other therapeutic agent) calculated to produce a desired effect.

"Isomers" refer to compounds having the same number and kind of atoms and hence the same molecular weight, but differing with respect to the arrangement or configuration of the atoms.

"Stereoisomers" refer to isomers that differ only in the arrangement of the atoms in space.

"Diastereoisomers" refer to stereoisomers that are not mirror images of each other.

"Enantiomers" refers to stereoisomers that are non-superimposable mirror images of one another. Enantiomers include "enantiomerically pure" isomers that comprise substantially a single enantiomer, for example, greater than or equal to 90%, 92%, 95%, 98%, or 99%, or equal to 100% of a single enantiomer.

"Epimers" refer to stereoisomers of a compound that have different configurations at only one of several stereogenic centers.

"Racemic" refers to a mixture containing equal parts of individual enantiomers.

"Non-racemic" refers to a mixture containing unequal parts of individual enantiomers. A non-racemic mixture may be enriched in the R- or S-configuration, including, without limitation, about 50/50, about 60/40, and about 70/30 R- to S-enantiomer, or S- to R-enantiomer, mixtures.

"Optional" or "optionally" means that the subsequently described event or circumstance may or may not occur, and that the description includes instances where the event or circumstance occurs and instances in which it does not. For example, an alkyl that is "optionally substituted" encompasses both an alkyl that is unsubstituted and an alkyl that is substituted.

"Subject" refers to a cell or tissue, in vitro or in vivo, an animal or a human. An animal or human subject may also be referred to as a "patient."

"Animal" refers to a living organism having sensation and the power of voluntary movement, and which requires for its existence oxygen and organic food.

"Mammal" refers to a warm-blooded vertebrate animal with hair or fur. Examples include without limitation members of the human, equine, porcine, bovine, murine, canine or feline species.

"Treating" in reference to a disease, disorder or condition refers to: (i) inhibiting a disease, disorder or condition, e.g., arresting its development; and/or (ii) relieving a disease, disorder or condition, e.g., causing regression of the clinical symptoms.

"Preventing" in reference to a disease, disorder or condition refers to preventing a disease, disorder or condition, e.g., causing the clinical symptoms of the disease, disorder or condition not to develop.

"Cancer" refers to an abnormal growth of cells which tend to proliferate in an uncontrolled way and, in some cases, to metastasize (spread). Specific cancers types include without limitation the cancers identified in Publication No. US 2006/0014949 and the following:

cardiac: sarcoma (e.g., such as angiosarcoma, fibrosarcoma, rhabdomyosarcoma, liposarcoma and the like), myxoma, rhabdomyoma, fibroma, lipoma and teratoma;

lung: bronchogenic carcinoma (e.g., such as squamous cell, undifferentiated small cell, undifferentiated large cell, adenocarcinoma and the like), alveolar (e.g., such as bronchiolar) carcinoma, bronchial adenoma, sarcoma, lymphoma, chondromatous hamartoma, mesothelioma;

gastrointestinal: esophagus (e.g., such as squamous cell carcinoma, adenocarcinoma, leiomyosarcoma, lymphoma and the like), stomach (e.g., such as carcinoma, lymphoma, leiomyosarcoma and the like), pancreas (e.g., such as ductal adenocarcinoma, insulinoma, glucagonoma, gastrinoma, carcinoid tumors, vipoma and the like), small bowel (e.g., such as adenocarcinoma, lymphoma, carcinoid tumors, Karposi's sarcoma, leiomyoma, hemangioma, lipoma, neurofibroma, fibroma, and the like), large bowel (e.g., such as adenocarcinoma, tubular adenoma, villous adenoma, hamartoma, leiomyoma and the like);

genitourinary tract: kidney (e.g., such as adenocarcinoma, Wilm's tumor nephroblastoma, lymphoma, leukemia, and the like), bladder and urethra (e.g., such as squamous cell carcinoma, transitional cell carcinoma, adenocarcinoma and the like), prostate (e.g., such as adenocarcinoma, sarcoma), testis (e.g., such as seminoma, teratoma, embryonal carcinoma, teratocarcinoma, choriocarcinoma, sarcoma, interstitial cell carcinoma, fibroma, fibroadenoma, adenomatoid tumors, lipoma and the like);

liver: hepatoma (e.g., hepatocellular carcinoma and the like), cholangiocarcinoma, hepatoblastoma, angiosarcoma, hepatocellular adenoma, hemangioma;

bone: osteogenic sarcoma (e.g., such as osteosarcoma and the like), fibrosarcoma, malignant fibrous histiocytoma, chondrosarcoma, Ewing's sarcoma, malignant lymphoma (e.g., such as reticulum cell sarcoma), multiple myeloma, malignant giant cell tumor chordoma, osteochronfroma (e.g., such as osteocartilaginous exostoses), benign chondroma, chondroblastoma, chondromyxofibroma, osteoid osteoma and giant cell tumors;

nervous system: skull (e.g., such as osteoma, hemangioma, granuloma, xanthoma, osteitis deformans and the like), meninges (e.g., such as meningioma, meningiosarcoma, gliomatosis and the like), brain (e.g., such as astrocytoma, medulloblastoma, glioma, ependymoma, germinoma [pinealoma], glioblastoma multiform, oligodendroglioma, schwannoma, retinoblastoma, congenital tumors and the like), spinal cord (e.g., such as neurofibroma, meningioma, glioma, sarcoma and the like);

gynecological: uterus (e.g., such as endometrial carcinoma and the like), cervix (e.g., such as cervical carcinoma, pre-tumor cervical dysplasia and the like), ovaries (e.g., such as ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma, and the like), vulva (e.g., such as squamous cell carcinoma, intraepithelial carcinoma, adenocarcinoma, fibrosarcoma, melanoma and the like), vagina (e.g., such as clear cell carcinoma, squamous cell carcinoma, botryoid sarcoma (embryonal rhabdomyosarcoma], fallopian tubes (carcinoma) and the like);

hematologic: blood (e.g., such as myeloid leukemia [acute and chronic], acute lymphoblastic leukemia, chronic lymphocytic leukemia, myeloproliferative diseases, multiple myeloma, myelodysplastic syndrome and the like), Hodgkin's disease, non-Hodgkin's lymphoma;

skin: malignant melanoma, basal cell carcinoma, squamous cell carcinoma, Karposi's sarcoma, moles dysplastic nevi, lipoma, angioma, dermatofibroma, keloids, psoriasis and the like; and adrenal glands: neuroblastoma.

Compounds

One aspect of the present invention relates to a compound of Formula I:

I

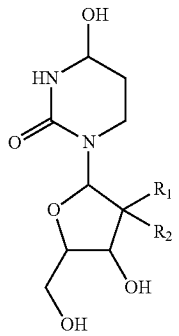

or a pharmaceutically acceptable salt of the compound, wherein:

$R_1$ and $R_2$ are independently selected from the group consisting of hydrogen, halo, cyano, nitro, sulfhydryl, hydroxyl, formyl, carboxyl, COO($C_1$ to $C_6$ straight or branched chain alkyl), COO($C_1$ to $C_6$ straight or branched chain alkenyl), COO($C_1$ to $C_6$ straight or branched chain alkynyl), CO($C_1$ to $C_6$ straight or branched chain alkyl), CO($C_1$ to $C_6$ straight or branched chain alkenyl), CO($C_1$ to $C_6$ straight or branched chain alkynyl), $C_1$ to $C_6$ straight or branched chain alkyl, $C_1$ to $C_6$ straight or branched chain alkenyl, $C_1$ to $C_6$ straight or branched chain alkynyl, $C_1$ to $C_6$ straight or branched chain alkoxy, and $C_1$ to $C_6$ straight or branched chain alkenoxy; wherein each occurrence of $C_1$ to $C_6$ straight or branched chain alkyl, $C_1$ to $C_6$ straight or branched chain alkenyl, $C_1$ to $C_6$ straight or branched chain alkynyl, $C_1$ to $C_6$ straight or branched chain alkoxy, or $C_1$ to $C_6$ straight or branched chain alkenoxy may be independently unsubstituted or substituted with one to four substituents independently selected from the group consisting of halo, hydroxyl, cyano, nitro, formyl, carboxyl, and sulfhydryl;

and provided that when one of $R_1$ and $R_2$ is —H, then the other is not —H, —OH or —$CH_2$OH.

In some embodiments, $R_1$ and $R_2$ are independently selected from the group consisting of hydrogen, halo, hydroxyl, cyano, nitro, sulfhydryl, $C_1$ to $C_6$ straight or branched chain alkyl, $C_1$ to $C_6$ straight or branched chain alkenyl, $C_1$ to $C_6$ straight or branched chain alkynyl, $C_1$ to $C_6$ straight or branched chain alkoxy, and $C_1$ to $C_6$ straight or branched chain alkenoxy; wherein each occurrence of $C_1$ to $C_6$ straight or branched chain alkyl, $C_1$ to $C_6$ straight or branched chain alkenyl, $C_1$ to $C_6$ straight or branched chain alkynyl, $C_1$ to $C_6$ straight or branched chain alkoxy, or $C_1$ to $C_6$ straight or branched chain alkenoxy may be independently unsubstituted or substituted with one ore more halos;

and provided that when one of $R_1$ and $R_2$ is —H, then the other is not —H, or —OH.

In some embodiments, $R_1$ and $R_2$ are independently selected from the group consisting of hydrogen, halo, $C_1$ to $C_6$ alkyl, $C_1$ to $C_6$ alkenyl, $C_1$ to $C_6$ alkoxy, and $C_1$ to $C_6$ alkenoxy; wherein each occurrence of $C_1$ to $C_6$ straight or branched chain alkyl, $C_1$ to $C_6$ straight or branched chain alkenyl, $C_1$ to $C_6$ straight or branched chain alkoxy and $C_1$ to $C_6$ straight or branched chain alkenoxy may be independently unsubstituted or substituted with one to three halos;

and provided that when one of $R_1$ and $R_2$ is —H, then the other is not —H, or —OH.

In further embodiments, at least one of $R_1$ and $R_2$ is halo.

In further embodiments, at least one of $R_1$ and $R_2$ is fluoro.

In further embodiments, one of $R_1$ and $R_2$ is halo, and the other is —H.

In further embodiments, one of $R_1$ and $R_2$ is fluoro, and the other is —H.

In further embodiments, $R_1$ and $R_2$ are each fluoro.

In further embodiments, one of $R_1$ and $R_2$ is halo, and the other is —CN.

In further embodiments, one of $R_1$ and $R_2$ is fluoro, and the other is —CN.

In further embodiments, one of $R_1$ and $R_2$ is halo, and the other is —$NO_2$.

In further embodiments, one of $R_1$ and $R_2$ is fluoro, and the other is —$NO_2$.

In further embodiments, one of $R_1$ and $R_2$ is halo, and the other is —SH.

In further embodiments, one of $R_1$ and $R_2$ is fluoro, and the other is —SH.

In further embodiments, one of $R_1$ and $R_2$ is halo, and the other is —OH.

In further embodiments, one of $R_1$ and $R_2$ is fluoro, and the other is —OH.

In further embodiments, one of $R_1$ and $R_2$ is halo, and the other is —CHO.

In further embodiments, one of $R_1$ and $R_2$ is fluoro, and the other is —CHO.

In further embodiments, one of $R_1$ and $R_2$ is halo, and the other is —COOH.

In further embodiments, one of $R_1$ and $R_2$ is fluoro, and the other is —COOH.

In further embodiments, one of $R_1$ and $R_2$ is halo, and the other is —$COOR_x$, wherein $R_x$ selected from the group consisting of $C_1$ to $C_6$ straight or branched chain alkyl, $C_1$ to $C_6$ straight or branched chain alkenyl, and $C_1$ to $C_6$ straight or branched chain alkynyl.

In further embodiments, one of $R_1$ and $R_2$ is fluoro, and the other is —$COOR_x$, wherein $R_x$ selected from the group consisting of $C_1$ to $C_6$ straight or branched chain alkyl, $C_1$ to $C_6$ straight or branched chain alkenyl, and $C_1$ to $C_6$ straight or branched chain alkynyl.

In further embodiments, one of $R_1$ and $R_2$ is halo, and the other is —$COR_x$, wherein $R_x$ selected from the group consisting of $C_1$ to $C_6$ straight or branched chain alkyl, $C_1$ to $C_6$ straight or branched chain alkenyl, and $C_1$ to $C_6$ straight or branched chain alkynyl.

In further embodiments, one of $R_1$ and $R_2$ is fluoro, and the other is —$COR_x$, wherein $R_x$ selected from the group consisting of $C_1$ to $C_6$ straight or branched chain alkyl, $C_1$ to $C_6$ straight or branched chain alkenyl, and $C_1$ to $C_6$ straight or branched chain alkynyl.

In further embodiments, one of $R_1$ and $R_2$ is halo, and the other is —$C_1$ to $C_6$ straight or branched chain alkyl.

In further embodiments, one of $R_1$ and $R_2$ is fluoro, and the other is —$C_1$ to $C_6$ straight or branched chain alkyl.

In further embodiments, one of $R_1$ and $R_2$ is halo, and the other is —$C_1$ to $C_6$ straight or branched chain alkenyl.

In further embodiments, one of $R_1$ and $R_2$ is fluoro, and the other is —$C_1$ to $C_6$ straight or branched chain alkenyl.

In further embodiments, one of $R_1$ and $R_2$ is halo, and the other is —$C_1$ to $C_6$ straight or branched chain alkoxy.

In further embodiments, one of $R_1$ and $R_2$ is fluoro, and the other is —$C_1$ to $C_6$ straight or branched chain alkoxy.

In further embodiments, one of $R_1$ and $R_2$ is halo, and the other is —$C_1$ to $C_6$ straight or branched chain alkenoxy.

In further embodiments, one of $R_1$ and $R_2$ is fluoro, and the other is —$C_1$ to $C_6$ straight or branched chain alkenoxy.

In further embodiments, at least one of $R_1$ and $R_2$ is —$C_1$ to $C_6$ straight or branched chain alkyl substituted with halo.

In further embodiments, one of $R_1$ and $R_2$ is —$C_1$ to $C_6$ straight or branched chain alkyl substituted with halo, and the other is —H.

In further embodiments, one of $R_1$ and $R_2$ is —$C_1$ to $C_6$ straight or branched chain alkyl substituted with fluoro, and the other is —H.

In further embodiments, at least one of $R_1$ and $R_2$ is —$C_1$ to $C_6$ straight or branched chain alkenyl substituted with halo.

In further embodiments, one of $R_1$ and $R_2$ is —$C_1$ to $C_6$ straight or branched chain alkenyl substituted with halo, and the other is —H.

In further embodiments, one of $R_1$ and $R_2$ is —$C_1$ to $C_6$ straight or branched chain alkenyl substituted with fluoro, and the other is —H.

In further embodiments, at least one of $R_1$ and $R_2$ is/are —$C_1$ to $C_6$ straight or branched chain alkoxy substituted with halo.

In further embodiments, one of $R_1$ and $R_2$ is —$C_1$ to $C_6$ alkoxy substituted with halo, and the other is —H.

In further embodiments, one of $R_1$ and $R_2$ is —$C_1$ to $C_6$ straight or branched chain alkoxy substituted with fluoro, and the other is —H.

In further embodiments, at least one of $R_1$ and $R_2$ is —$C_1$ to $C_6$ straight or branched chain alkenoxy substituted with halo.

In further embodiments, one of $R_1$ and $R_2$ is —$C_1$ to $C_6$ straight or branched chain alkenoxy substituted with halo, and the other is —H.

In further embodiments, one of $R_1$ and $R_2$ is —$C_1$ to $C_6$ straight or branched chain alkenoxy substituted with fluoro, and the other is —H.

In some embodiments, the compound of Formula is:

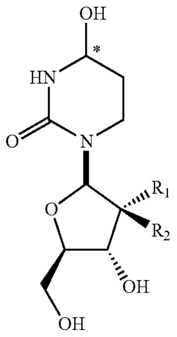

wherein the carbon marked by an asterisk may have an (R) or an (S) configuration. In some embodiments, a disclosed pharmaceutical composition or method of use may comprise a compound with an (R) configuration an (S) configuration, or a mixture of (R) and (S) configurations. In some embodiments, $R_1$ and $R_2$ are independently selected from fluoro and hydrogen, with the proviso that $R_1$ and $R_2$ may not both be hydrogen.

In further embodiments, the compound of Formula I has the stereochemistry of either Ia or Ib:

Ia

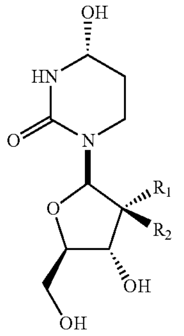

Ib

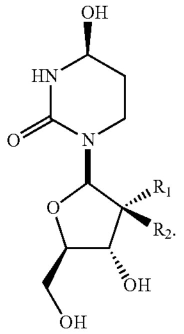

In further embodiments, the compound of Formula I is selected from the group consisting of Compounds 1 to 23 and pharmaceutically acceptable salts thereof:

Compound 1

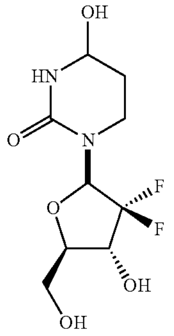

Compound 2

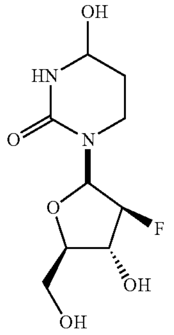

-continued
Compound 3
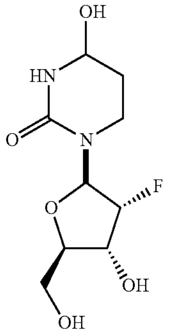
Compound 4
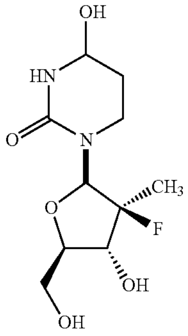
Compound 5
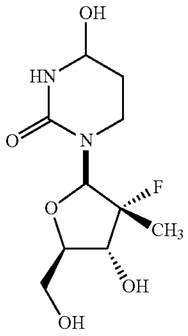
Compound 6
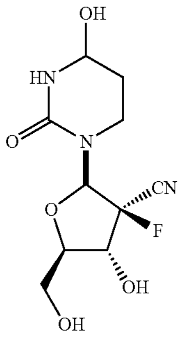
-continued
Compound 7
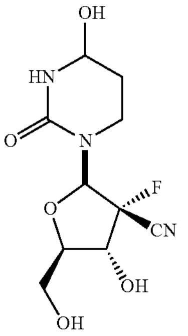
Compound 8
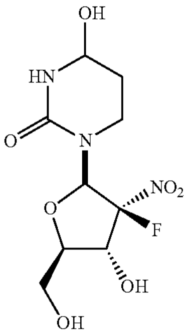
Compound 9
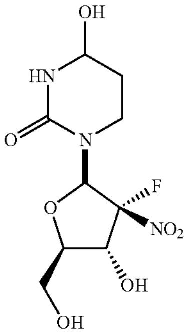
Compound 10
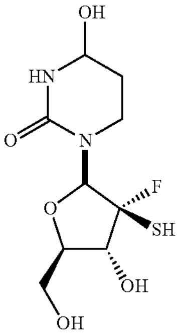

-continued
Compound 11
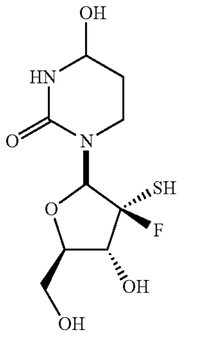
Compound 12
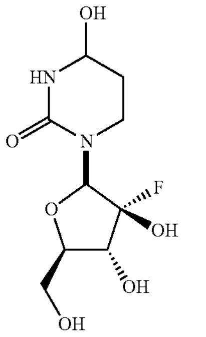
Compound 13
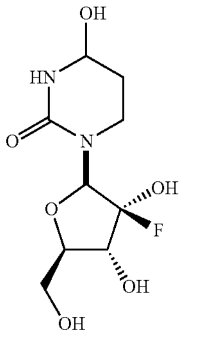
Compound 14
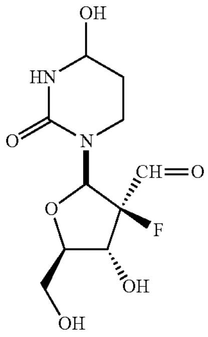
-continued
Compound 15
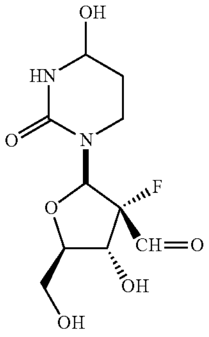
Compound 16
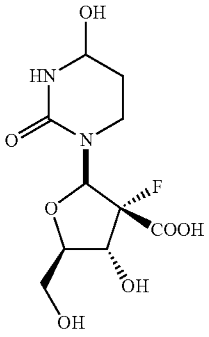
Compound 17
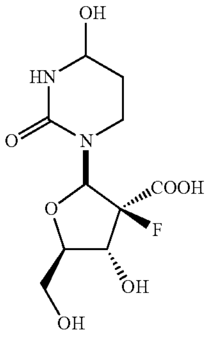
Compound 18
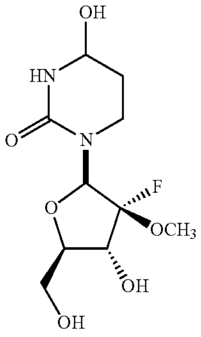

-continued
Compound 19
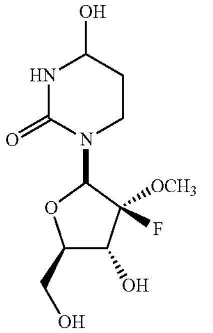
Compound 20
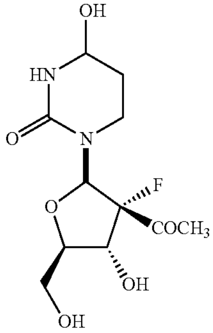
Compound 21
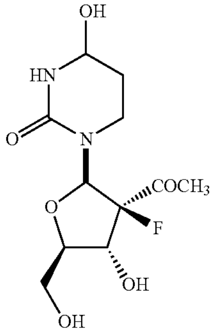
Compound 22
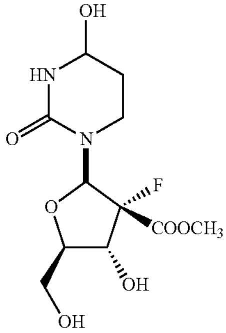
-continued
Compound 23
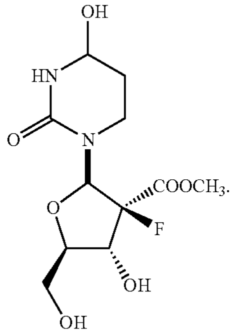
In further embodiments, the compound of Formula I is selected from the group consisting of Compounds 1a, 1b, 2a, 2b, 3a, 3b, and pharmaceutically acceptable salts thereof.
Compound 1a
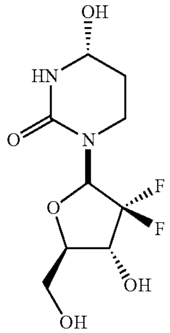
Compound 1b
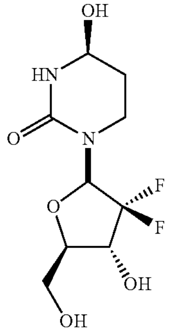
Compound 2a
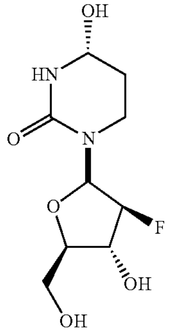

-continued

Compound 2b

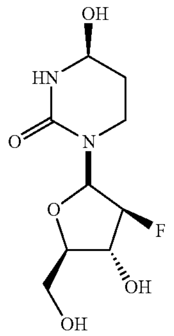

Compound 3a

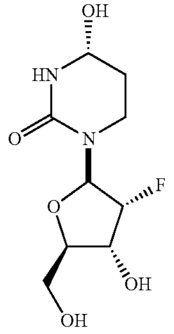

Compound 3b

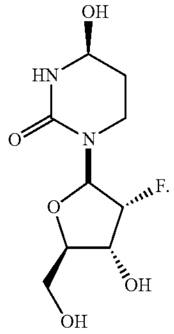

Since the compounds of the invention may possess at least one chiral center, they may exist in the form of enantiomers, diastereomers, racemic mixtures, non-racemic mixtures or other stereoisomers. The present invention encompasses all such possible isomers, as well as geometric isomers and tautomers.

Stereoisomers may be prepared or isolated by known methods. For example, diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereoselective reactions.

Pharmaceutical Compositions

Another aspect of the present invention relates to a pharmaceutical composition comprising:

(i) an effective amount of a compound of the invention as described herein, including but not limited to each express embodiment; and (ii) a pharmaceutically acceptable excipient.

In further embodiments, the pharmaceutical composition further comprises an effective amount of at least one additional therapeutic agent, such as a CDA substrate drug or chemotherapeutic agent.

The CDA substrate drug may be any drug that can be deaminated by CDA. Nonlimiting examples of a CDA substrate include cytosine and cytidine analogs, such as decitabine, 5-azacytidine, gemcitabine, ara-C, troxacitabine, tezacitabine, 5'-fluoro-2'-deoxycytidine, cytochlor, and the compounds disclosed in US Publication No. 2006/0014949. In some embodiments, the CDA substrate drug is decitabine. In other embodiments, the CDA substrate drug is 5-azacytidine. In yet other embodiments, the CDA substrate drug is gemcitabine. In yet other embodiments, the CDA substrate drug is ara-C.

Examples of a chemotherapeutic agent include without limitation:

alkylating agents (e.g., which may include doxorubicin, cyclophosphamide, estramustine, carmustine, mitomycin, bleomycin and the like);

antimetabolites (e.g., which may include 5-Fluoro-Uracil, capecitabine, gemcitabine, nelarabine, fludarabine, methotrexate and the like);

platinating agents (e.g., which may include cisplatin, oxaliplatin, carboplatin and the like);

topoisomerase inhibitors (e.g., which may include topotecan, irinotecan, etoposide and the like);

tubulin agents (e.g., which may include paclitaxel, docetaxel, vinorelbine, vinblastine, vincristine, other taxanes, epothilones, and the like);

signalling inhibitors (e.g., kinase inhibitors, antibodies, farnesyltransferase inhibitors, and the like); and other chemotherapeutic agents (e.g, tamoxifen, anti-mitotic agents such as polo-like kinase inhibitors or aurora kinase inhibitors, and the like).

The "effective amount" of the compound of the invention may vary from 0.1 wt. % to about 100 wt. %. In some embodiments, the effective amount of the compound is 0.1 to 20% w/w. In other embodiments, the effective amount is 1-10% w/w. In yet other embodiments, the effective amount is 2-5% w/w.

The pharmaceutical compositions of the invention may be formulated for administration in solid or liquid form, including those adapted for the following: (1) oral administration, for example, drenches (for example, aqueous or non-aqueous solutions or suspensions), tablets (for example, those targeted for buccal, sublingual and systemic absorption), caplets, boluses, powders, granules, pastes for application to the tongue, hard gelatin capsules, soft gelatin capsules, mouth sprays, troches, lozenges, pellets, syrups, suspensions, elixirs, liquids, emulsions and microemulsions; (2) parenteral administration, for example, by subcutaneous, intramuscular, intravenous or epidural injection as, for example, a sterile solution or suspension; (3) topical application, for example, as a cream, ointment, patch, pad or spray applied to the skin; (4) intravaginally or intrarectally, for example, as a pessary, cream or foam; (5) sublingually; (6) ocularly; (7) transdermally; or (8) nasally. The pharmaceutical compositions may be formulated for immediate, sustained or controlled release.

In some embodiments, the pharmaceutical compositions are formulated for oral administration. In further embodiments, the pharmaceutical compositions are formulated for oral administration in solid form.

Pharmaceutical compositions of the invention can be prepared using known materials and techniques, which may include but are not limited to mixing and/or blending the compound of the invention with the pharmaceutically acceptable excipient and optional therapeutic agent(s).

Methods

Another aspect of the present invention relates to a method for inhibiting cytidine deaminase, comprising administering to a subject in need thereof an effective amount of a compound or pharmaceutical composition of the invention as described herein, including but not limited to each express embodiment.

In some embodiments, the subject is a mammal. In further embodiments, the subject is a human.

Another aspect of the present invention relates to a method for treating cancer, comprising administering to a subject in need thereof:

(i) an effective amount of a compound or pharmaceutical composition of the invention as described herein, including but not limited to each express embodiment; and (ii) a CDA substrate drug, including but not limited to each express embodiment described herein.

In some embodiments, the subject is a mammal. In further embodiments, the subject is a human.

In some embodiments, the cancer is selected from hematological cancers and solid cancers. In further embodiments, the hematological cancer selected from MDS and leukemia. In further embodiments, the solid cancer is selected from pancreatic cancer, ovarian cancer, peritoneal cancer, non small cell lung cancer, and breast cancer. In yet further embodiments, the leukemia is acute myeloid leukemia (AML) or chronic myeloid leukemia (CML).

Another aspect of the present invention relates to a method for inhibiting degradation of a CDA substrate drug by cytidine deaminase, comprising administering an effective amount of a compound or pharmaceutical composition of the invention as described herein, including but not limited to each express embodiment, to a subject that is undergoing treatment with the CDA substrate drug. The CDA substrate drug, including but not limited to each express embodiment described herein.

In some embodiments, the subject is a mammal. In further embodiments, the subject is a human.

Administration of the compound or composition of the invention may be via any accepted mode known to one skilled in the art, for example, orally, parenterally, by inhalation spray, topically, rectally, nasally, buccally, vaginally, intraoccularly, intrapulmonarily, or via an implanted reservoir. The term "parenterally" includes without limitation subcutaneously, intravenously, intramuscularly, intraperitoneally, intrathecally, intraventricularly, intrasternally, intracranially, by intraosseous injection and by infusion techniques.

Any administration regimen well known to those skilled in the art for regulating the timing and sequence of drug delivery can be used and repeated as necessary to effect treatment in the methods of the invention. For example, the compound or composition of the invention may be administered 1, 2, 3 or 4 times daily, by a single dose, multiple discrete doses or continuous infusion.

The compound or composition of the invention may be administered prior to, at substantially the same time with; or after administration of the CDA substrate drug. The administration regimen may include pretreatment and/or co-administration with at least one additional therapeutic agent. In such case, the compound or composition of the invention, CDA substrate drug and at least one additional therapeutic agent may be administered simultaneously, separately, or sequentially.

Examples of administration regimens include without limitation:

administration of each compound, composition, CDA substrate drug, and/or therapeutic agent in a sequential manner; and co-administration of each compound, composition, CDA substrate drug, and/or therapeutic agent in a substantially simultaneous manner (e.g., as in a single unit dosage form) or in multiple, separate unit dosage forms for each compound, composition, CDA substrate drug, and/or therapeutic agent.

It will be appreciated by those skilled in the art that the "effective amount" or "dose level" will depend on various factors such as the particular administration mode, administration regimen, compound, and composition selected, and the particular disease and patient being treated. For example, the appropriate dose level may vary depending upon the activity, rate of excretion and possible toxicity of the specific compound or composition employed; the age, body weight, general health, gender and diet of the patient being treated; the frequency of administration; the other therapeutic agent(s) being co-administered; and the type and severity of the disease.

The present invention contemplates dose levels on the order of about 0.001 to about 10,000 mg/kg/d. In some embodiments, the dose level is about 0.1 to about 1,000 mg/kg/d. In other embodiments, the dose level is about 1 to about 100 mg/kg/d. In yet other embodiments, the dose level is about 1 to about 50 mg/kg/d. In yet other embodiments, the dose level is about 1 to about 25 mg/kg/d. Appropriate dose levels, mode of administration, and administration regimen may be ascertained by those skilled in the art using known techniques.

Kits

Another aspect of the present invention relates to a kit comprising at least one unit dosage form, which unit dosage form comprises a compound or pharmaceutical composition of the invention.

The kit may further comprise a container and/or a package suitable for commercial sale. The container can be in any conventional shape or form as known in the art which is made of a pharmaceutically acceptable material, such as a paper or cardboard box, a glass or plastic bottle or jar, a re-sealable bag, or a blister pack with individual dosages for pressing out of the pack according to a therapeutic schedule. More than one container can be used together in a single package. For example, tablets may be contained in a blister pack which is in turn contained within a box.

The kit may further comprise information. The information may be provided on a readable medium. The readable medium may comprise a label. The information may be directed towards a physician, pharmacist or patient. The information may indicate that the unit dosage form may cause one or more adverse effects. The information may comprise instructions for administering the unit dosage form, such as in a manner described herein. These instructions may be provided in a variety of ways. For example, the information may include a table including a variety of weights or weight ranges and appropriate dosages for each weight or weight range.

The information can be associated with the container, for example, by being: written on a label (e.g., the prescription label or a separate label) adhesively affixed to a container; included inside a container as a written package insert; applied directly to the container such as being printed on the wall of a box or blister pack; or attached as by being tied or taped, for example as an instructional card affixed to the neck of a bottle via a string, cord or other line, lanyard or tether type device.

It will be apparent to those skilled in the art that specific embodiments of the present invention may be directed to one, some or all of the above-indicated aspects as well as other aspects, and may encompass one, some or all of the above- and below-indicated embodiments, as well as other embodiments.

Other than in the working examples, or where otherwise indicated, all numbers expressing quantities of ingredients, reaction conditions, and so forth used in the specification and claims are to be understood as being modified by the term "about". Accordingly, unless indicated to the contrary, such numbers are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding techniques.

While the numerical ranges and parameters setting forth the broad scope of the invention are approximations, the numerical values set forth in the working examples are reported as precisely as possible. Any numerical value, however, inherently contains certain errors necessarily resulting from the standard deviation found in their respective testing measurements.

EXAMPLES

The following examples are illustrative of the present invention and are not intended to be limitations thereon.

Synthesis of Compounds

Compound of the invention can be prepared as described herein and/or by the application or adaptation of known methods. It will be appreciated by those skilled in the art that one or more of the reactants, steps and/or conditions described in the reaction schemes may require adjustment to accommodate other substituents at $R_1$ and $R_2$.

Example 1

Scheme 1. Synthesis of difluorotetrahydrouridine derivatives (Compounds 1a and 1b)

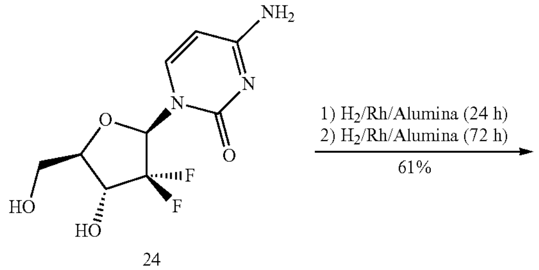

24

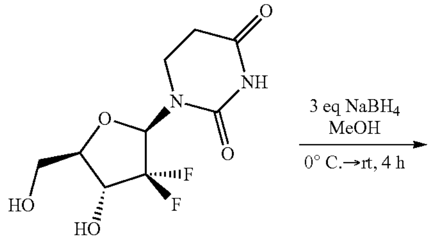

25

-continued

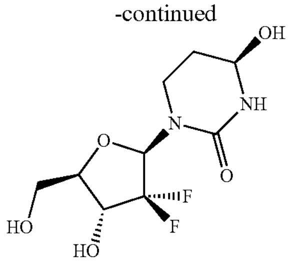

1a (29%)

+

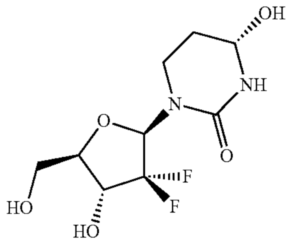

1b (31%)

+

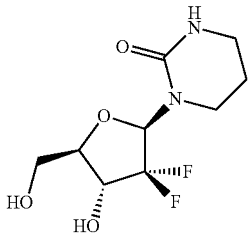

26 (17%)

2'2'-DiFluoro-DiHydro-Uridine (DFDHU, 25)

Gemcitabine 24 (3.0 g, 11.4 mmol) is dissolved in $H_2O$ (50 mL). Rhodium on alumina (900 mg) is added to the solution and the mixture is hydrogenated overnight at 40 psi. The next day, the mixture is filtered, the water is removed in vacuo and the resulting sticky solid is dissolved in $H_2O$ again. Rhodium on alumina is added to the solution (900 mg) and the material is hydrogenated overnight at 40 psi. The rhodium is filtered off and the resulting filtrate is concentrated to afford a crude mixture of difluorodihydrouridine (5, DFDHU) and ~10% of difluorotetrahydrouridine 1a and 1b (DFTHU). The crude mixture is purified on reverse phase HPLC (reverse phase $C_{18}$ @ 5% $CH_3CN/H_2O$) to afford 1.84 g (61%, 14.5 minutes) of DFDHU 25 and 175 mg (17%, 1a, 9.5 minutes and 1b, 13.9 minutes) of the epimers of DFTHU. The absolute configuration of C-4 for compound 1a is determined by single crystal X-ray diffraction, and is consistent with literature precedents on the crystal structure of cytidine deaminase in complex with a single epimer of tetrahydrouridine. $^1$HNMR of 5: 6.00 (dd, 1H), 4.20 (q, 1H), 3.92-3.72 (m, 3H), 3.64 (m, 1H), 3.43 (m, 1H), 2.68 (t, 2H).

2'2'-DiFluoro-TetraHydroUridine (DFTHU, 1a and 1b)

The DFDHU 25 (1.2 g, 4.9 mmol) is dissolved in 30 mL of MeOH and cooled to 0° C. Sodium borohydride (540 mg, 14.6 mmol) is added portion-wise to the solution and the reaction is slowly warmed to room temperature. After 4 hours of stirring at room temperature (r.t.), the MeOH is removed in vacuo and the residue is dissolved in 15 mL of $H_2O$. The solution is neutralized with 2.0 N HCl to pH 7. The solution is then purified via prep HPLC (reverse phase $C_{18}$ @ 5% $CH_3CN/H_2O$). The salts come out at 5.2 minutes. One peak is apparent at 7.5 minutes (12%). One epimer of the DFTHU 1a comes out at 9.5 minutes (350, 29%). The other epimer 1b comes out at 14.3 minutes (370 mg, 31%). The deoxygenated product 26 elutes at 17 minutes (200 mg, 17%).

1a $^1$HNMR ($D_2O$, 9.5 minutes): 6.03 (dd, 1H), 5.04 (bs, 1H), 4.20 (q, 1H), 3.90-3.71 (m, 3H), 3.53 (dt, 1H), 3.30 (dt, 1H), 1.92-1.75 (m, 2H). Anal. Calcd. for $C_9H_{14}N_2O_5F_2$ ($0.15H_2O$): C, 39.90; H, 5.32; N, 10.34. Found: C, 39.87; H, 5.41; N, 10.26.

1b $^1$HNMR ($D_2O$, 14.3 minutes): 5.97 (dd, 1H), 5.03 (bt, 1H), 4.16 (q, 1H), 3.91-3.68 (m, 3H), 3.41 (dt, 1H), 3.20 (dt, 1H), 1.95-1.80 (m, 2H). Anal Calcd. for $C_9H_{14}N_2O_5F_2$ ($0.60H_2O$): C, 38.74; H, 5.49; N, 10.04. Found: C, 38.55; H, 5.36; N, 9.87.

26 $^1$H NMR ($D_2O$) δ 5.99 (dd, J=15 Hz, 6 Hz, 1H), 4.17 (m, 1H), 3.89 (m, 1H), 3.75 (m, 2H), 3.42 (m, 1H), 3.21 (t, J=6 Hz, 2H), 3.18 (m, 1H), 1.86 (m, 2H).

Example 2

Scheme 2. Synthesis of 2′(R)-fluoro-2′deoxy-tetrahydrouridines (Compounds 2a and 2b)

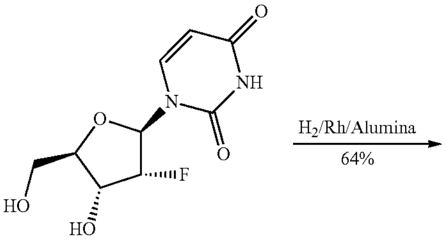

27

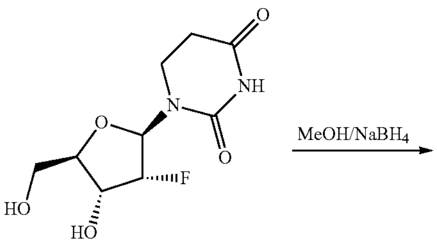

28

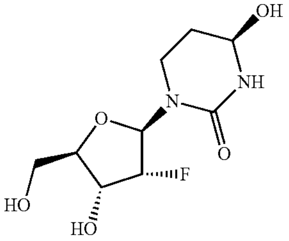

+

2a (46%)

-continued

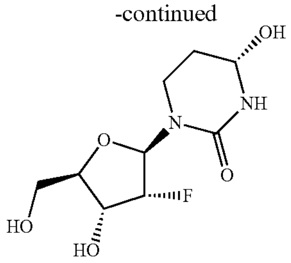

+

2b (21%)

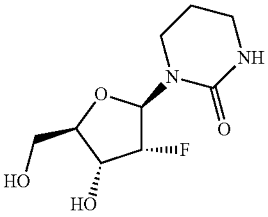

29 (9%)

2'(R)-Fluoro-2'deoxy-DiHydroUridine [(R)-FDHU, 28]

2'-Fluoro-2'-deoxyuridine 27 (1.2 g, 4.9 mmol) is dissolved in $H_2O$ (30 mL) with a few drops of concentrated ammonium hydroxide (5 drops). Rhodium on alumina (300 mg) is added to the solution and the mixture is hydrogenated overnight at 40 psi. The next day, the mixture is filtered and the filtrate is concentrated and purified via prep HPLC (reverse phase $C_{18}$ @ 5% $CH_3CN/H_2O$). The major product is 28, (R)-FDHU, which elutes at 9.2 minutes (780 mg, 64%). Some residual starting material 7a (5.5 minutes, 95 mg, 8%) and a minor amount of the FTHU 2a and 2b (7.2 minutes, 50 mg, 4% and 8.6 minutes, 45 mg, 4%) are isolated. $^1$HNMR 28 ($D_2O$): 5.83 (dd, 1H), 5.07 (dd, 1H), 4.18 (q, 1H), 3.90-3.78 (m, 2H), 3.65 (dt, 1H), 3.52-3.35 (m, 2H), 2.64 (t, 2H).

2'(R)-Fluoro-2'-deoxy-TetraHydroUridine ((R)-FTHU, 2a and 2b)

The (R)-FDHU (600 mg, 2.4 mmol) is dissolved in 20 mL of MeOH and cooled to 0° C. Sodium borohydride (355 mg, 9.6 mmol) is added portion-wise to the solution and the reaction is slowly warmed to room temperature overnight. The MeOH is removed in vacuo and the residue is dissolved in 10 mL of $H_2O$. The solution is neutralized with 2.0 N HCl to pH 7. The solution is then purified via prep HPLC (reverse phase $C_{18}$ @ 5% $CH_3CN/H_2O$). The desired product 2a elutes at 7.2 minutes (275 mg, 46%) followed by the other epimer 2b at 8.6 minutes (125 mg, 21%) and some residual starting material at 9.2 minutes and the fully reduced material 29 (50 mg, 9%) at 14.9 minutes. The stereochemistry at C-4 for 2a and 2b are assigned based on literature precedents on the crystal structure of cytidine deaminase in complex with a single epimer of tetrahydrouridine.

2a (7.2 minutes): $^1$HNMR (DMSO-$d_6$): 7.21 (d, 1H), 5.93 (dd, 1H), 5.59 (d, 1H), 5.39 (d, 1H), 4.99-4.75 (m, 3H), 3.95 (m, 1H), 3.62-3.21 (m, 5H), 1.69 (m, 2H); $^{13}$CNMR: 153.12, 91.2 (d), 85.93 (d), 81.36, 71.30, 68.3 (d), 60.43, 34.13, 28.66. Anal. Calcd, for $C_9H_{15}N_2O_5F$ ($0.5H_2O$): C, 41.70; H, 6.22; N, 10.81. Found: C, 41.67; H, 6.26; N, 10.76.

2b (8.6 minutes): $^1$HNMR (DMSO-$d_6$): 7.15 (d, 1H), 5.95 (dd, 1H), 5.58 (d, 1H), 5.40 (d, 1H), 5.00-4.75 (m, 3H), 3.92

(m, 2H), 3.61-3.29 (m, 5H), 2.98 (m, 1H), 1.80-1.65 (m, 2H); $^{13}$CNMR: 154.02, 92.24 (d), 86.62 (d), 81.63, 71.73, 68.86 (d), 60.89, 35.08, 29.00.

29 (14.9 minutes): $^1$HNMR ($D_2O$): 5.93 (dd, 1H), 5.07 (d, 1H), 4.61 (m, 1H), 4.24 (m, 1H), 3.96-3.65 (m, 3H), 3.35-3.14 (m, 3H), 2.12-1.79 (m, 2H).

Example 3

Scheme 3. Synthesis of 2′(S)-fluoro-2′deoxy-tetrahydrouridines (Compounds 3a and 3b)

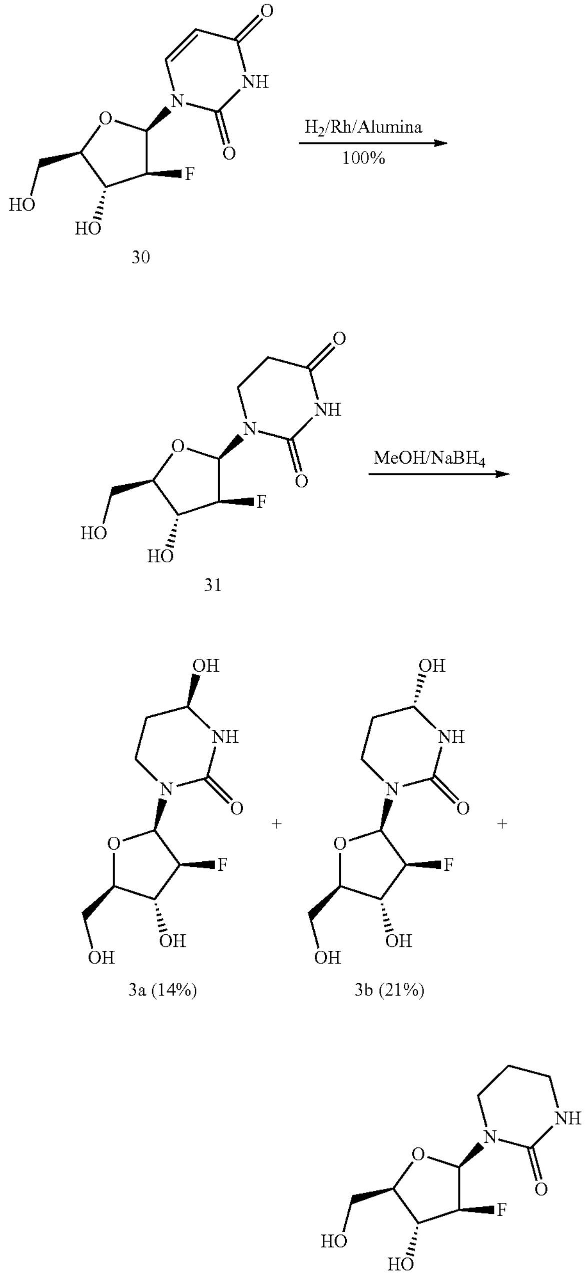

30

31

3a (14%)

3b (21%)

32 (trace)

2'(S)-fluoro-2'deoxy-dihydrouridine [(S)-FDHU, 31]

Compound 30 (1.2 g, 4.0 mmol) is dissolved in $H_2O$ (40 mL). Rhodium on alumina (200 mg) is added to the solution and the mixture is hydrogenated overnight at 50 psi. The next day, the mixture is filtered through a pad of celite and concentrated in vacuo. The desired product 31 is obtained in quantitative yield (>1.0 g). $^1$HNMR ($D_2O$): 6.08 (dd, 1H), 5.09 (dt, 1H), 4.28 (m, 1H), 3.85-3.80 (m, 2H), 3.72 (m, 2H), 3.51 (m, 1H), 2.65 (t, J=9 Hz, 2H).

2'(S)-fluoro-2'deoxy-tetrahydrouridine [(S)-FTHU, 3a and 3b]

Compound 31 (1.12 mg, 4.55 mmol) is dissolved in 28 mL of MeOH and cooled to 0° C. Sodium borohydride (475 mg, 12.55 mmol) is added portion-wise to the solution and the reaction is allowed to continue for 1 hour and 15 minutes. The MeOH is removed in vacuo and the residue is dissolved in 15 mL of 5% $CH_3CN/H_2O$. The solution is neutralized with 2.0 N HCl to pH 7 (~3 ml). The solution is then purified via prep HPLC (reverse phase $C_{18}$ Phenomenex Luna with a 5% $CH_3CN/H_2O$ (isocratic eluent and refractive index detector). The desired product 3a elutes at 9.3 minutes (163 mg, 14%) followed by the other epimer 3b at 13.4 minutes (236 mg, 21%), some residual starting material (not quantified), as well as the fully reduced product 32 (not quantified) are detected. Stereochemistry at C-4 for 3a and 3b are assigned based on literature precedents on the crystal structure of cytidine deaminase in complex with a single epimer of tetrahydrouridine.

3a (9.3 minutes): $^1$HNMR ($D_2O$) δ 6.12 (dd, 1H), 5.04 (dt, 1H), 5.03 (m, 1H), 4.27 (m, 1H), 3.83-3.59 (m, 4H), 3.34 (m, 1H), 1.86 (m, 2H). $^{13}$CNMR: 157.9, 98.6 (d), 83.9 (d), 82.5, 75.7 (d), 74.0, 62.6, 37.5, 30.0. Anal. Calcd, for $C_9H_{15}N_2O_5F$ ($0.25H_2O$): C, 42.44; H, 6.13; N, 11.00. Found: C, 42.49; H, 6.09; N, 10.82.

3b (13.4 minutes): $^1$HNMR ($D_2O$) δ 6.07 (dd, 1H), 5.02 (dt, 1H), 5.02 (t, 1H), 4.26 (dt, 1H), 3.84-3.66 (m, 4H), 3.35 (m, 1H), 1.86 (m, 2H); $^{13}$CNMR: 157.8, 98.2 (d), 84.4, 82.0, 75.7, 74.0, 62.4, 38.4, 29.3. Anal. Calcd. for $C_9H_{15}N_2O_5F$ ($0.4H_2O$): C, 41.96; H, 6.19; N, 10.87. Found: C, 41.99; H, 6.15; N, 10.91.

Example 4

CDA Enzymatic Activity

The ability of the compounds of the invention to inhibit the enzymatic activity of CDA may be demonstrated using the following assay method.

The procedure to determine CDA enzymatic activity is based on published methodologies (for example, Cacciamani, T. et al., *Arch. Biochem. Biophys.* 1991, 290, 285-92; Cohen R. et al., *J. Biol. Chem.*, 1971, 246, 7566-8; Vincenzetti S. et al., *Protein Expr. Purif.* 1996, 8, 247-53). The assay follows the change in absorbance at 286 nm of the CDA-catalyzed deamination of cytidine to form uridine. The reaction is carried out in potassium phosphate buffer (pH 7.4, 20 mM, containing 1 mM DTT) in a total volume of 200 μl in a 96-well plate format. The final reaction mixture contains cytidine (50 μM) and purified human recombinant CDA. Purified enzyme is diluted so as to produce an absorbance change of approximately 2 milli-absorbance units/minute. Base line measurements of absorbance change over time are made before CDA addition to insure no change of absorbance in the absence of CDA. After CDA addition, absorbance change is monitored for 20-30 minutes. When potential inhibitors are present, eight concentrations of each in the 0.1 nM-1 mM range are tested in order to obtain $IC_{50}$ values. The slope of the change of absorbance over time for samples containing both cytidine and CDA but no inhibitor (totals) is normalized to 100%. CDA enzymatic activity left in the presence of a compound expressed as percent of total activity is subtracted from 100% in order to obtain percent inhibition at varying compound concentrations.

Using the above described assay, the inhibitory potency of Compounds 1 and 2 are evaluated. The $IC_{50}$ values of the compounds are set forth in Table 1. “1a” and “1b” denote single stereoisomers; “1” denotes an epimeric mixture.

TABLE 1

Inhibitory Potency of Test Compounds

| Compound | $IC_{50}$ (nM) |
|---|---|
| 1a | 400 ± 60 |
| 1b | 5000 ± 1000 |
| 1 | 400 ± 60 |
| 2a | 200 ± 50 |
| 2b | 5000 ± 2000 |
| 2 | 2000 ± 3000 |
| 3a | 400 ± 80 |
| 3b | 4000 ± 700 |
| 3 | 2000 ± 1000 |

Enhancement of Efficacy of CDA Substrate Drugs

The ability of the compounds of the invention to enhance the efficacy of CDA substrate drugs may be demonstrated in the L1210 mouse lymphoma model.

Example 5

The Effect of CDA Inhibitor, Compound 1, on Decitabine (0.1 mg/Kg) Induced Survival in the L1210 Survival Model Methods CD2F1 6-7 weeks old female mice are randomly separated into 6 groups:

| Group # | |
|---|---|
| 1 | L1210 i.v and Vehicle + Vehicle p.o. × 2 for 4 days |
| 2 | L1210 i.v. and Vehicle + Compound 1 10 mg/kg p.o. × 2 for 4 days |
| 3 | L1210 i.v. and Vehicle + 0.1 mg/kg decitabine p.o. × 2 for 4 days |
| 4 | L1210 i.v. and Compound 1 1 mg/kg + 0.1 mg/kg decitabine p.o. × 2 for 4 days |
| 5 | L1210 i.v. and Compound 1 10 mg/kg + 0.1 mg/kg decitabine p.o. × 2 for 4 days |
| 6 | L1210 i.v. and Vehicle + 0.1 mg/kg decitabine i.p. × 2 for 4 days |

L1210 Intravenous (i.v.) Injection:

Prior to experiment, L1210 cells are passed at least 3 times in CD2F1 female mice. The mice are injected intraperitoneally (i.p.) with L1210 ascites one prior week to sacrifice using $CO_2$. Each mouse is placed on its back, its belly surface is cleaned with alcohol wipes and a small incision is made into its peritoneal cavity. 2 ml of ice cold 2.1% bovine serum albumin (BSA) in saline is injected into the cavity. Fluid is withdrawn from the cavity, transferred with an 18 G 3 cc syringe into a clean sterile tube, and kept on ice. The fluid is diluted 1:10 in 2.1% BSA in saline and one drop of zap-o-globin is added to 2 ml of diluted ascites. Diluted ascites (dilute 1:10 again) are counted on a hematocytomer and the number of cells/ml is calculated. A stock of ascites in BSA solution is diluted to $1\times10^4$ cells/0.1 ml. Mice are injected with 0.1 ml of cell solution with a 27 G needle.

Dose Solution Preparation:

When appropriate, mice are dosed with a vehicle or Compound 1 p.o 30 minutes prior to decitabine.

Compound 1 is prepared at 1 mg/ml in phosphate buffer saline (PBS) and then diluted to 0.1 mg/ml in PBS for the lower dose.

Decitabine is prepared at a 1 mg/ml stock in PBS and diluted appropriately to achieve a 0.01 and 0.02 mg/ml dosing solution.

Dosing Scheme:

Decitabine is prepared fresh twice a day. All dose solutions are stored on ice while dosing. Mice are dosed i.p. or orally (p.o.) twice a day (8 hours apart) for 4 consecutive days. Final dosing scheme and total decitabine and Compound 1 doses are outlined in Table 2.

TABLE 2

Dosing Scheme

| Group # | Drug | Decitabine Dose (route administered) | Cumulative Decitabine Dose | Compound 1 Dose | Cumulative Compound 1 Dose |
|---|---|---|---|---|---|
| 1 | Vehicle | Vehicle | 0 mg/kg | Vehicle | 0 mg/kg |
| 2 | Compound 1 | Vehicle | 0 mg/kg | 10 mg/kg | 80 mg/kg |
| 3 | Decitabine | 0.1 mg/kg p.o. | 0.8 mg/kg | Vehicle | 0 mg/kg |
| 4 | Decitabine/ Compound 1 | 0.1 mg/kg p.o. | 0.8 mg/kg | 1 mg/kg | 40 mg/kg |
| 5 | Decitabine/ Compound 1 | 0.1 mg/kg p.o. | 0.8 mg/kg | 10 mg/kg | 80 mg/kg |
| 6 | Decitabine | 0.1 mg/kg i.p | 0.8 mg/kg | Vehicle | 0 mg/kg |

Survival and Autopsy:

Mice are observed for survival and weighed daily (Monday to Friday) for the duration of the study (30 days). Dead mice are autopsied and observed for the presence of tumors in organs. Tumor deaths are determined by liver weights greater than 1.6 g and spleen weights greater than 150 mg as per Covey et al., *Eur. Cancer Oncol.* 1985.

Mice dosed with decitabine or decitabine plus Compound 1 live longer than mice dosed with vehicle control or Compound 1 alone (FIG. 1 and Table 3; $p<0.05$). A trend for a dose response is observed with Compound 1 in combination with decitabine.

Decitabine (0.1 mg/kg) p.o. is less effective than 0.1 mg/kg decitabine i.p., but not significantly different (Table 3; FIG. 1, $p=0.052$).

Co-administration of 10 mg/kg Compound 1 with 0.1 mg/kg decitabine p.o. significantly enhances survival compared to 0.1 mg/kg decitabine p.o. alone ($p=0.0031$) and 0.1 mg/kg decitabine i.p. ($p=0.016$; Table 3, FIG. 1). Co-administration of 1 mg/kg Compound 1 with 0.1 mg/kg decitabine p.o. significantly enhances survival compared to 0.1 mg/kg decitabine p.o. alone ($p=0.0031$), but not compared to 0.1 mg/kg decitabine i.p. ($p=0.13$; Table 3, FIG. 1).

Table 3 lists the mean survival of each treatment group and the percent ILS (increased life span) compared to the vehicle group. All treated groups live significantly longer than vehicle controls and CDA inhibitor alone groups ($p<0.05$).

Table 3 lists the weights of the livers and spleens of mice on autopsy. All mice except for the one 0.1 mg/kg decitabine i.p. mouse died a ‘tumor burden’ related death as indicated by the liver weights greater than 1 g and the spleen weights greater than 80 mg (Covey et al., supra). The weights of liver and spleen from 3 control mice are 0.97±0.08 g and 0.08±0.02 g. Gross observations are noted concerning the overall appearance of the peritoneal and thoracic cavities.

TABLE 3

Effect of Decitabine and Compound 1 on Survival and Liver and Spleen Weights in L1210 IV Survival Model

| Group # | L1210 cells | Mean Survival (days) ± SD | * % ILS (Increased Life Span) | Mean Liver wts. (g) ± SD | Mean Spleen wts. (g) ± SD |
|---|---|---|---|---|---|
| 1 | 1 x $10^4$ | 7.40 ± 0.55 | n/a | 1.81 ± 0.13 | 0.31 ± 0.05 |
| 2 | 1 x $10^4$ | 7.40 ± 0.55 | 0.00 | 1.99 ± 0.22 | 0.39 ± 0.07 |
| 3 | 1 x $10^4$ | 10.6 ± 0.56 | 43.24 | 2.05 ± 0.17 | 0.33 ± 0.06 |
| 4 | 1 x $10^4$ | 12.8 ± 0.45 | 72.97 | 2.03 ± 0.08 | 0.29 ± 0.03 |
| 5 | 1 x $10^4$ | 14.2 ± 0.45 | 91.89 | 2.02 ± 0.27 | 0.29 ± 0.07 |

$$* \% \text{ ILS} = \frac{\text{mean survival of experimental (days)} - \text{mean survival of control (days)} \times 100}{\text{mean survival of control (days)}}$$

FIG. 1 is a graph that shows the effect of Compound 1 on decitabine (DAC) induced survival in the L1210 mouse lymphoma model.

Example 6

Figure 2:
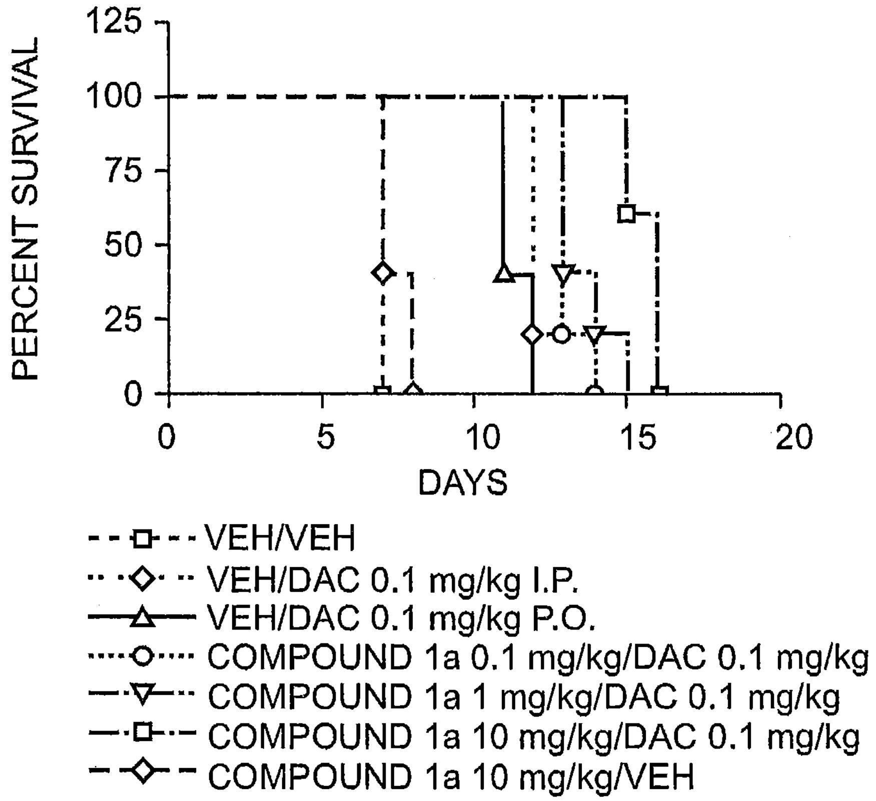
FIG. 2 is a graph that shows the effect of Compound 1a on decitabine induced survival in the L1210 mouse lymphoma model.

The Effect of CDA Inhibitor, Compound 1a, on Decitabine (0.1 mg/Kg) Induced Survival in the L1210 Survival Model Compound 1a is evaluated in the L1210 model following the protocol of Example 5. Mice dosed with decitabine (“DAC”), and DAC plus Compound 1a, live longer than those receiving vehicle control and CDA inhibitor alone (FIG. 2; $p<0.05$). In combination with DAC, 10 mg/kg Compound 1a is more effective at extending survival than the lower doses.

Example 7

Figure 3:
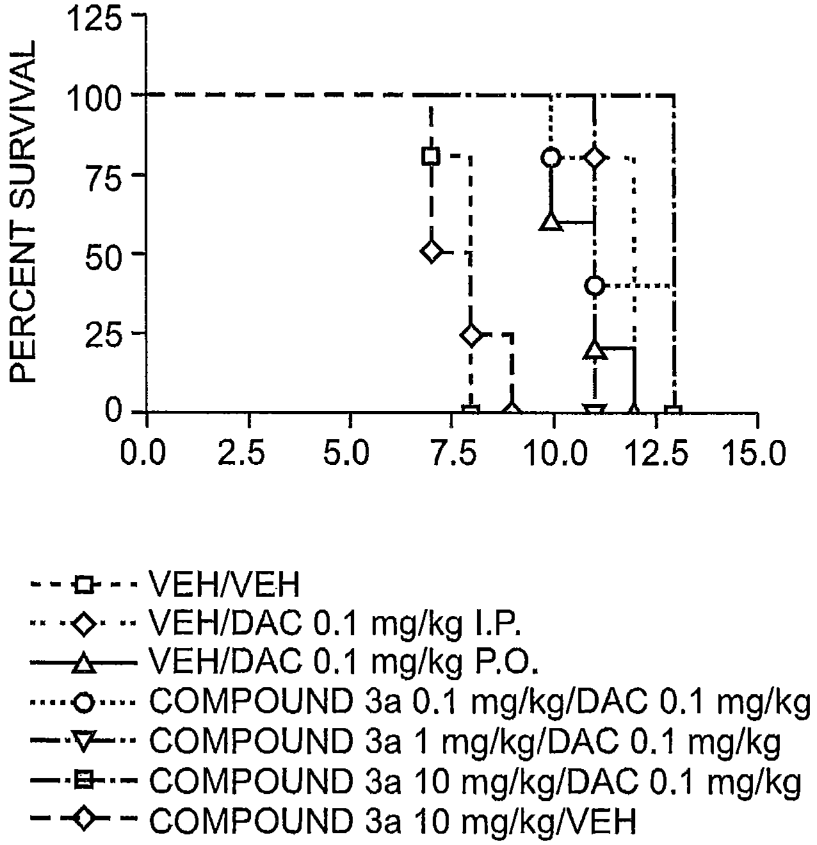
FIG. 3 is a graph that shows the effect of Compound 3a on decitabine induced survival in the L1210 mouse lymphoma model.

The Effect of CDA Inhibitor, Compound 3a, on Decitabine (0.1 mg/Kg) Induced Survival in the L1210 Survival Model Compound 3a is evaluated in the L1210 model following the protocol of Example 5. Mice dosed with decitabine (“DAC”), and DAC plus Compound 3a live longer than vehicle controls and CDA inhibitor alone (FIG. 3; $p<0.05$).

Example 8

The Effect of CDA Inhibitor, Compound 1 on Cytarabine (Ara-C) Induced Survival in the L1210 Survival Model 50 CD2F1 6-7 weeks old female mice are randomly separated into 10 groups. (N=5 mice/group):

| Group # | |
|---|---|
| 1 | L1210 i.v. and Veh + Veh (PBS) p.o. × 2 for 4 days |
| 2 | L1210 i.v. and Veh + Ara-C 200 mg/kg p.o. × 2 for 4 days |
| 3 | L1210 i.v. and Veh + Ara-C 100 mg/kg p.o. × 2 for 4 days |
| 4 | L1210 i.v. and Veh + Ara-C 50 mg/kg p.o. × 2 for 4 days |
| 5 | L1210 i.v. and Veh + Ara-C 25 mg/kg p.o × 2 for 4 days |
| 6 | L1210 i.v. and Compound 1 10 mg/kg + Ara-C 200 mg/kg × 2 for 4 days |
| 7 | L1210 i.v. and Compound 1 10 mg/kg + Ara-C 100 mg/kg × 2 for 4 days |
| 8 | L1210 i.v. and Compound 1 10 mg/kg + Ara-C 50 mg/kg × 2 for 4 days |
| 9 | L1210 i.v. and Compound 1 10 mg/kg + Ara-C 25 mg/kg × 2 for 4 days |
| 10 | L1210 i.v. and Compound 1 10 mg/kg + Veh p.o. × 2 for 4 days |

L1210 IV Injection:

CD2F1 female mice are injected i.p. with L1210 ascites one prior week to sacrifice ($CO_2$). L1210 cells are passed at least 3 times in vivo prior to experiment. The mouse is placed on its back, belly surface cleaned with alcohol wipes and a small incision made into peritoneal cavity. 2 ml of ice cold 2.1% BSA in saline is injected into cavity and then fluid withdrawn and transferred with an 18 G 3 cc syringe into a clean sterile tube and kept on ice. The fluid is diluted 1:10 in 2.1% BSA in saline and one drop of zap-o-globin is added to 2 ml of diluted ascites. Diluted ascites (dilute 1:10 again) are counted on a hematocytomer and the number of cells/ml is calculated. Stock of ascites in BSA solution is diluted to $1\times10^4$ cells/0.1 ml. Mice are injected with 0.1 ml of cell solution with 27 G needle. Total i.v. injections take about 50 minutes.

Dose Solution Preparation:

When appropriate mice are dosed with vehicle or Compound 1 p.o. 30 minutes prior to Ara-C. Compound 1 is prepared at 1 mg/ml in PBS and Ara-C is prepared at a 20 mg/ml stock in PBS and then diluted appropriately for lower doses.

Dosing Scheme:

Compound 1 is prepared at the beginning of the study and stored at 4° C. Ara-C is prepared fresh twice a day. All solutions are stored on ice while dosing. Mice are dosed orally twice a day (8 hours apart) for 4 consecutive days. Final dosing scheme and total Ara-C and Compound 1 dose is outlined in Table 4.

TABLE 4

Dosing Scheme

| Group # | Drug | Ara-C Dose (route adm.) | Cumulative Ara-C Dose | Compound 1 Dose | Cumulative Compound 1 Dose |
|---|---|---|---|---|---|
| 1 | Veh | Veh | 0 mg/kg | Veh | 0 mg/kg |
| 2 | Compound 1 | Veh | 0 mg/kg | 10 mg/kg | 40 mg/kg |
| 3 | Ara-C | 200 mg/kg p.o. | 800 mg/kg | Veh | 0 mg/kg |
| 4 | Ara-C | 100 mg/kg p.o. | 400 mg/kg | Veh | 0 mg/kg |
| 5 | Ara-C | 50 mg/kg p.o. | 200 mg/kg | Veh | 0 mg/kg |
| 6 | Ara-C | 25 mg/kg p.o. | 100 mg/kg | Veh | 0 mg/kg |
| 7 | Ara-C | 200 mg/kg p.o. | 800 mg/kg | 10 mg/kg | 40 mg/kg |
| 8 | Ara-C | 100 mg/kg p.o. | 400 mg/kg | 10 mg/kg | 40 mg/kg |
| 9 | Ara-C | 50 mg/kg p.o. | 200 mg/kg | 10 mg/kg | 40 mg/kg |
| 10 | Ara-C | 25 mg/kg p.o. | 100 mg/kg | 10 mg/kg | 40 mg/kg |

Survival and Autopsy:

Mice are observed for survival and weighed daily (Mon-Fri) for the duration of the study (45 days). Dead mice are autopsied and observed for the presence of tumors in organs. Tumor deaths are determined by liver weights greater than 1.6 g and spleen weights greater than 150 mg as per Covey et al., supra.

Figure 4:
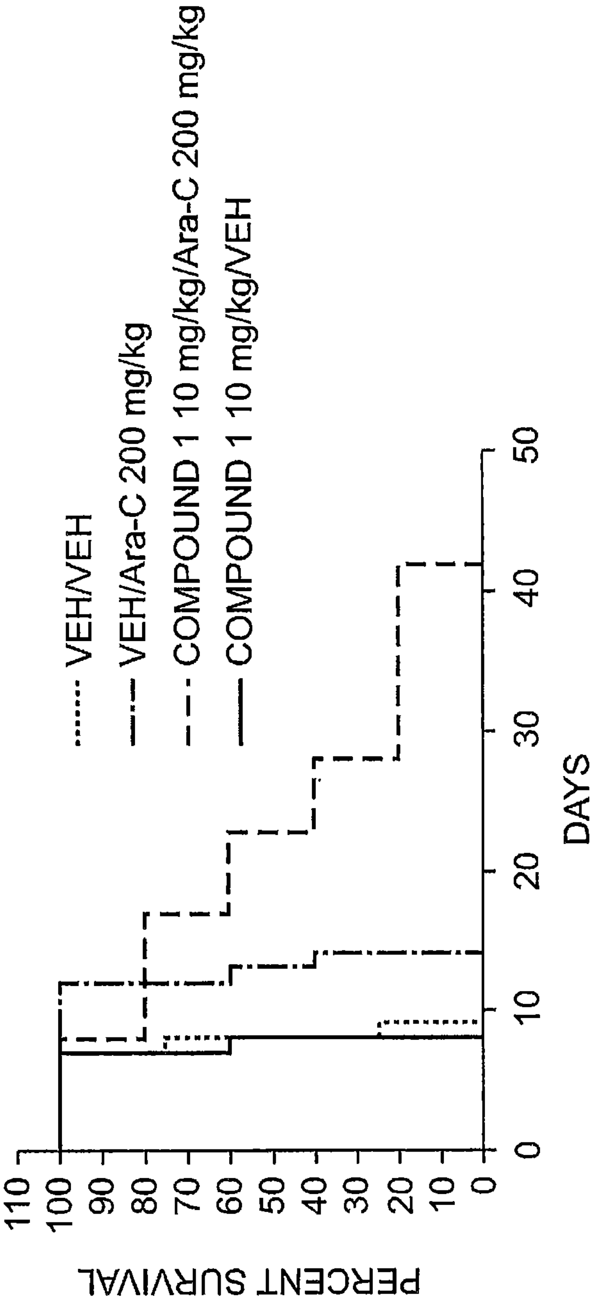
FIG. 4 is a graph that shows the effect of Compound 1 on Ara-C (200 mg/kg) induced survival in the L1210 model.
Figure 5:
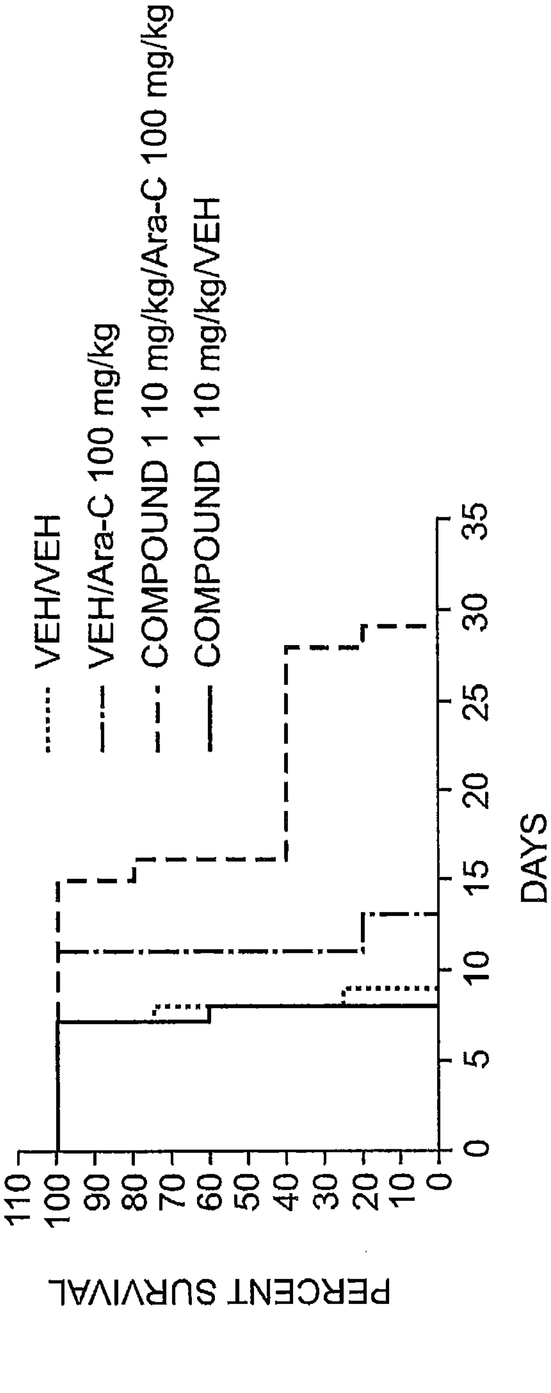
FIG. 5 is a graph that shows the effect of Compound 1 on Ara-C (100 mg/kg) induced survival in the L1210 model.
Figure 6:
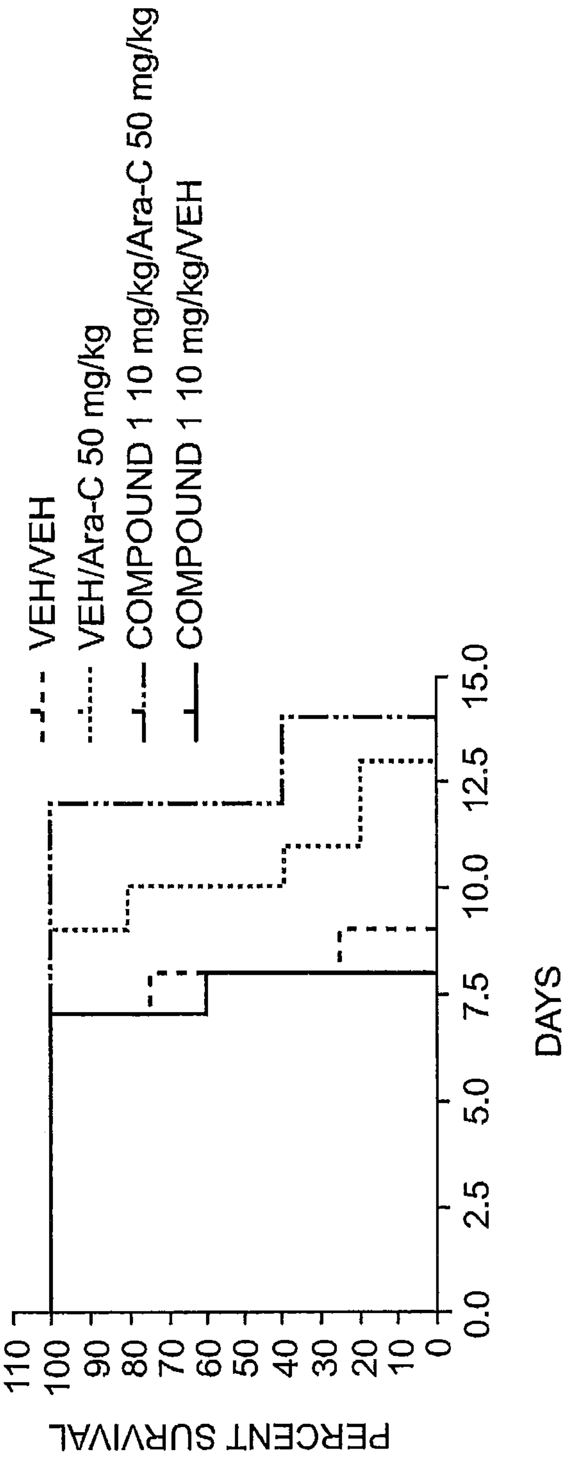
FIG. 6 is a graph that shows the effect of Compound 1 on Ara-C (50 mg/kg) induced survival in the L1210 model.
Figure 7:
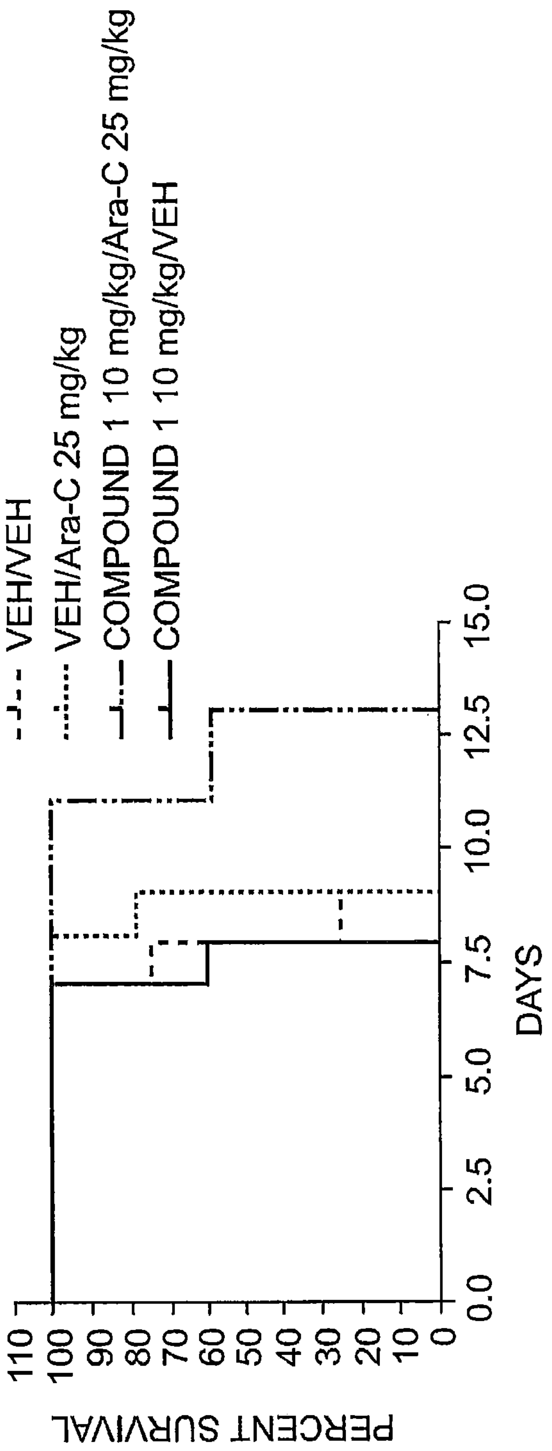
FIG. 7 is a graph that shows the effect of Compound 1 on Ara-C (25 mg/kg) induced survival in the L1210 model.

Mice dosed with Ara-C alone (50 mg/kg, 100 mg/kg and 200 mg/kg) and Ara-C plus Compound 1 live longer than mice treated with vehicle control and CDA inhibitor alone (FIGS. 4-7; $p<0.05$). Compound 1 alone has no effect on survival compared to vehicle controls (FIG. 4).

25 mg/kg Ara-C alone has no effect at extending survival compared to mice treated with vehicle and 10 mg/kg Compound 1. 50, 100 and 200 mg/kg Ara-C significantly enhance survival (days) in a dose dependent manner compared to mice in the control group. Co-administration of 10 mg/kg Compound 1 with Ara-C p.o. significantly enhances survival compared to the survival time of mice treated with the same dose of Ara-C alone (FIGS. 4-7).

Example 9

Effect of Compound 1 on Gemcitabine-Induced Reduction of Tumor Volume in the Mouse A2780 Human Ovarian Cancer Xenograft Model The oral efficacy of gemcitabine is tested in combination with Compound 1 in the human ovarian cancer xenograft A2780. Female NCr nu/nu 5-6 week old mice are implanted subcutaneously with 30 to 60 mg tumor fragments. On day 11 when the tumors are approximately 200 $mm^3$, treatment starts as described in Table 5.

TABLE 5

Dosing Scheme

| Groups | Treatment | Gemcitabine Schedule | Compound 1 Schedule |
|---|---|---|---|
| 1 | Vehicle (saline) | PO; q3dx4 | |
| 2 | Compound 1 | | PO 10 mg/kg q3dx4 |
| 3 | Gemcitabine | PO 10 mg/kg; q3dx4 | |
| 4 | Gemcitabine/ Compound 1* | PO 10 mg/kg; q3dx4 | PO 10 mg/kg q3dx4 |
| 5 | Gemcitabine | PO 30 mg/kg; q3dx4 | |
| 6 | Gemcitabine/ Compound 1* | PO 30 mg/kg; q3dx4 | PO 10 mg/kg q3dx4 |

*Compound 1 is dosed approximately 30 min prior to Gemcitabine

Tumor volume is followed throughout the experiment. Tumor volume is measured three times weekly. Tumor burden (mg=$mm^3$) is calculated from caliper measurements by the formula for the volume of a prolate ellipsoid $(L\times W^2)/2$ where L and W are the respective orthogonal length and width measurements (mm).

The primary endpoints used to evaluate efficacy in the A2780 model are complete and partial tumor regressions, tumor growth delay and the number of tumor free survivors at the end of the study. A complete response (CR) is defined as a decrease in tumor size to an undetectable size (<50 $mm^3$). A partial response (PR) is defined as >50% decrease in tumor mass form starting tumor size. A tumor that achieves a CR or PR during the study but starts to grow again is still considered a CR or PR Tumor free survival (TFS) at the end of the study would be no detectable tumor (<50 $mm^3$) at study termination (day 74). Tumor growth delay (TGD) is defined in this experiment as the median number of days for the treatment group compared to the control group to reach 750 $mm^3$.

Figure 8:
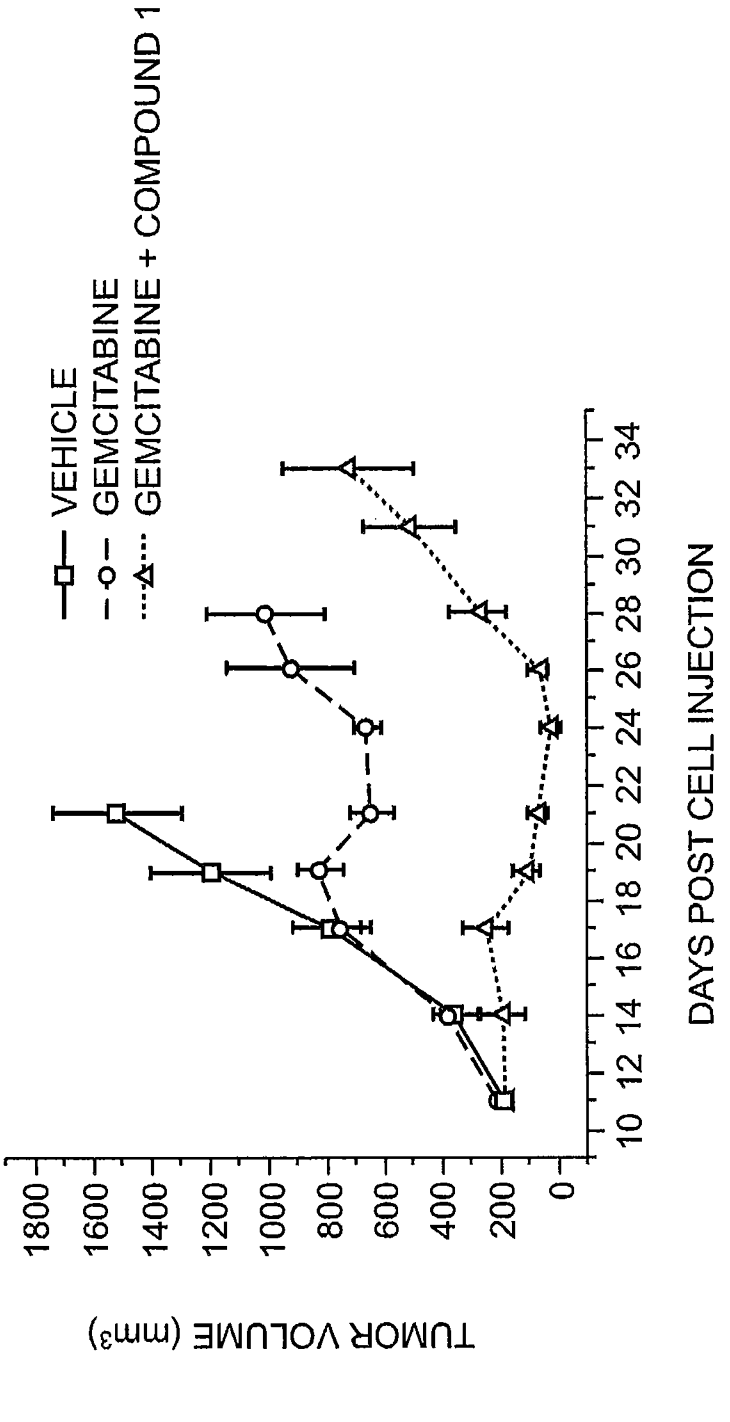
FIG. 8 is a graph that shows the effect of Compound 1 on gemcitabine-induced reduction of tumor volume in the mouse A2780 human ovarian cancer xenograft model.

Oral administration of 10 mg/kg PO q3d×4 gemcitabine is not very effective in this model with a tumor growth delay of 6.1 days (not statistically significant), with no CRs, PRs or tumor free survivors at termination of the experiment at day 74. When 10 mg/kg Gemcitabine is dosed in combination with Compound 1, significant delay of tumor growth is observed compared to this dose of gemcitabine alone (19.2 days; $p<0.05$ compared to Gem alone) with 75% of tumors displaying CR, but there are no TFS at the end of the experiment. In FIG. 8 (Tumor Volume vs Time (days) post treatment start, it is apparent that Compound 1 alone has no effect on tumor growth, while combination treatment with Compound 1 and gemcitabine is more effective than gemcitabine alone.

Oral administration of 30 mg/kg PO q3d×4 (MTD) gemcitabine is effective in producing a statistically significant tumor growth delay of 22 days with 63% CRs but no TFS. Combination chemotherapy with gemcitabine (30 mg/kg PO) plus Compound 1 produced a statistically significant tumor growth delay of >57 days and 100% CR and a 50% incidence of TFS at day 74, termination of the experiment.

TABLE 6

Effect of Combination treatment Gemcitabine and Compound 1 on Tumor Growth delay in the A2780 Ovarian cancer model

| Treatment | TGD | P value |
|---|---|---|
| Untreated Control | NA | |
| 10 mg/kg Compound 1 | 0.4 days | |
| 10 mg/kg Gemcitabine | 6.1 days | |
| 10 mg/kg Gemcitabine + Compound 1 | 19.2 days | <0.05 compared to 10 mg/kg Gem alone |
| 30 mg/kg Gemcitabine | 22 days | <0.05 compared to Untreated control |
| 30 mg/kg Gemcitabine + Compound 1 | >57 days | <0.05 compared to 30 mg/kg Gem alone |

Example 10

Solid State Characterization of Compound 1a

Data Collection

A colorless prism crystal of Compound 1a ($F_2O_5N_2C_9H_{14}$) having approximate dimensions of 0.48×0.43×0.32 mm is mounted in a loop. All measurements are made on a Rigaku RAXIS SPIDER imaging plate area detector with graphite monochromated Cu—Kα radiation.

Indexing is performed from 5 oscillations that are exposed for 60 seconds. The crystal-to-detector distance is 127.40 mm.

Cell constants and an orientation matrix for data collection correspond to a primitive trigonal cell (laue class: −3m1) with dimensions:

a=9.78961(18) Å c=20.4588(7) Å

V=1698.02(7) $Å^3$

For Z=6 and F.W.=268.22, the calculated density is 1.574 $g/cm^3$. Based on the systematic absences of:

0001: 1±3n and the successful solution and refinement of the structure, the space group is determined to be:

$P3_121$ (#152)

The data is collected at a temperature of −123±1° C. to a maximum 2θ value of 136.4°. A total of 111 oscillation images are collected. A sweep of data is done using co scans from 20.0 to 200.0° in 5.0° steps, at χ=0.0° and ϕ=180.0°. A second sweep is performed from 20.0 to 200.0° in 5.00 steps, at χ=54.0° and ϕ=180.0°. A third sweep is performed from 20.0 to 185.0° in 5.0° steps, at χ=54.0° and ϕ=90.0°, and a final sweep is performed using ω scans from 20.0 to 50.0° in 5.0° steps, at χ=0.0° and ϕ=0.0°. The exposure rate is 12.0 [sec./° ]. The crystal-to-detector distance is 127.40 mm. Readout is performed in the 0.100 mm pixel mode.

Data Reduction

Of the 11772 reflections that are collected, 2052 are unique ($R_{int}$=0.038); equivalent reflections are merged.

The linear absorption coefficient, μ, for Cu—Kα radiation is 13.035 $cm^{-1}$. An empirical absorption correction is applied which results in transmission factors ranging from 0.540 to 0.659. The data is corrected for Lorentz and polarization effects. A correction for secondary extinction (Larson, A. C., *Crystallographic Computing* 1970, 291-294; equation 22, with V replaced by the cell volume) is applied (coefficient=0.005900).

Structure Solution and Refinement

The structure is solved by direct methods (SIR92: Larson, A. C., *J. Appl. Cryst.,* 1994, 27, 435) and expanded using Fourier techniques (DIRDIF99: Beurskens, P. T. et al., *The DIRD-99 Program System. Technical Report of the Crystallography Laboratory,* 1999, University of Nijmegen, The Netherlands). The non-hydrogen atoms are refined anisotropically. Some hydrogen atoms are refined isotropically and the rest are refined using the riding model. The final cycle of full-matrix least-squares refinement (least squares weights=$\Sigma w(F_o^2-F_c^2)^2$) on $F^2$ is based on 2052 observed reflections and 181 variable parameters and converges (largest parameter shift is <0.01 times its esd) with unweighted and weighted agreement factors of:

$$R1=\Sigma||Fo|-|Fc||/\Sigma|Fo|=0.0303$$

$$wR2=[\Sigma(w(Fo^2-F_c^2)^2)/\Sigma w(F_o^2)^2]^{1/2}=0.0733$$

The standard deviation of an observation of unit weight (standard deviation=$[\Sigma w(F_o^2-F_c^2)^2/(N_o-N_v)]^{1/2}$, $N_o$=number of observations, $N_v$=number of variables) is 1.10. Unit weights are used. The maximum and minimum peaks on the final difference Fourier map correspond to 0.22 and −0.22 $e^-/Å^3$, respectively. The absolute structure is deduced based on Flack parameter, 0.0(1), refined using 839 Friedel pairs (Flack, H. D., *Acta Cryst.* 1983, A39, 876-881.

Neutral atom scattering factors are taken from Cromer, D. T. et al., *International Tables for X-ray Crystallography* 1974, IV, Table 2.2 A. Anomalous dispersion effects are included in Fcalc (Ibers, J. A. et al., *Acta Crystallogr.* 1964, 17, 781); the values for Δf' and Δf" are those of Creagh, D. C. et al., *International Tables for Crystallography* 1992, C, Table 4.2.6.8, 219-222. The values for the mass attenuation coefficients are those of Creagh, D. C. et al., *International Tables for Crystallography* 1992, C, Table 4.2.4.3, 200-206. All calculations are performed using the CrystalStructure 3.8 crystallographic software package except for refinement, which is performed using SHELXL-97.

Experimental Details

A. Crystal Data

| | |
|---|---|
| Empirical Formula | $F_2O_5N_2C_9H_{14}$ |
| Formula Weight | 268.22 |
| Crystal Color, Habit | colorless, prism |
| Crystal Dimensions | 0.48 × 0.43 × 0.32 mm |
| Crystal System | trigonal |
| Lattice Type | Primitive |
| Indexing Images | 5 oscillations @ 60.0 seconds |
| Detector Position | 127.40 mm |
| Pixel Size | 0.100 mm |
| Lattice Parameters | a = 9.78961(18) Å<br>c = 20.4588(7) Å<br>V = 1698.02(7) $Å^3$ |
| Space Group | $P3_121$ (#152) |
| Z value | 6 |
| $D_{calc}$ | 1.574 $g/cm^3$ |
| $F_{000}$ | 840.00 |
| μ(CuKα) | 13.035 $cm^{-1}$ |

B. Intensity Measurements

| | |
|---|---|
| Diffractometer | Rigaku RAXIS-SPIDER |
| Radiation | CuKα (λ = 1.54187 Å) graphite monochromated |
| Detector Aperture | 460 mm x 256 mm |
| Data Images | 111 exposures |
| ω Oscillation Range (χ = 0.0, φ = 180.0) | 20.0-200.0° |
| ω Oscillation Range (χ = 54.0, φ = 180.0) | 20.0-200.0° |
| ω Oscillation Range (χ = 54.0, φ = 90.0) | 20.0-185.0° |
| ω Oscillation Range (χ = 0.0, φ = 0.0) | 20.0-50.0° |
| Exposure Rate | 12.0 sec./° |
| Detector Position | 127.40 mm |
| Pixel Size | 0.100 mm |
| $2\theta_{Max}$ | 136.4° |
| No. of Reflections Measured | Total: 11772 |
| | Unique: 2052 ($R_{int}$ = 0.038) |
| | Friedel pairs: 839 |
| Corrections | Lorentz-polarization |
| | Absorption |
| | (trans. factors: 0.540-0.659) |
| | Secondary Extinction |
| | (coefficient: 5.90000e-003) |

C. Structure Solution and Refinement

| | |
|---|---|
| Structure Solution | Direct Methods (SIR92) |
| Refinement | Full-matrix least-squares on $F^2$ |
| Function Minimized | $\Sigma$ w $(Fo^2 - Fc^2)^2$ |
| Least Squares Weights | w = $1/[\sigma^2(Fo^2) + (0.0317 \cdot P)^2 + 0.6904 \cdot P]$ where P = $(Max(Fo^2, 0) + 2Fc^2)/3$ |
| $2\theta_{Max}$ cutoff | 136.4° |
| Anomalous Dispersion | All non-hydrogen atoms |
| No. Observations (All Reflections) | 2052 |
| No. Variables | 181 |
| Reflection/Parameter Ratio | 11.34 |
| Residuals: R1 (I > 2.00σ(I)) | 0.0303 |
| Residuals: R (All Reflections) | 0.0329 |
| Residuals: wR2 (All Reflections) | 0.0733 |
| Goodness of Fit Indicator | 1.099 |
| Flack Parameter (Friedel pairs = 839) | 0.0(1) |
| Max Shift/Error in Final Cycle | <0.001 |
| Maximum peak in Final Diff. Map | $0.22e^-/Å^3$ |
| Minimum peak in Final Diff. Map | $-0.22e^-/Å^3$ |

Figure 9:
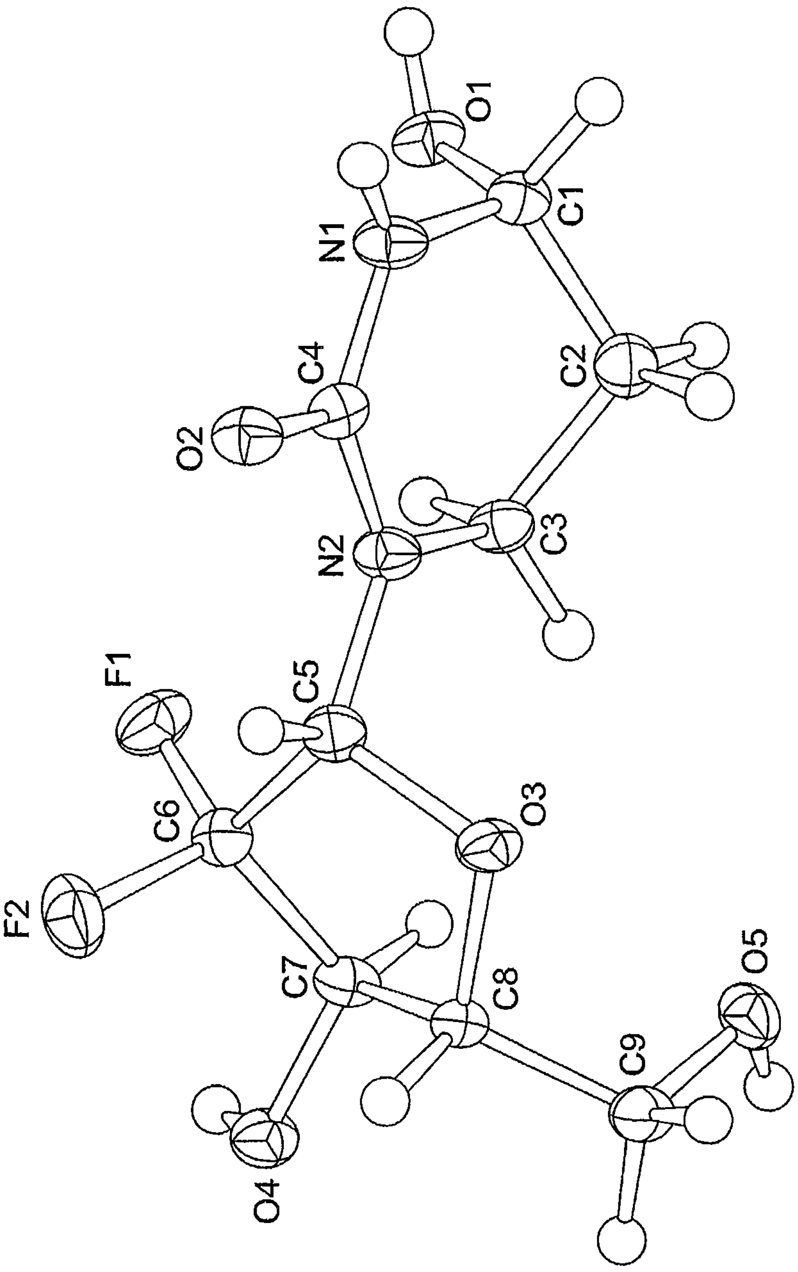

An ORTEP plot (Michael N. Burnett and Carroll K. Johnson, ORTEP-III: Oak Ridge Thermal Ellipsoid Plot Program for Crystal Structure Illustrations, Oak Ridge National Laboratory Report ORNL-6895, 1996) of the determined structure of Compound 1a is shown in FIG. 9.

Example 11

Enhancement of Acid Stability of Compound 1a Compared to THU

The stability of Compound 1a and tetrahydrouridine (THU) in acid solution are evaluated by $^1H$ NMR spectroscopy.

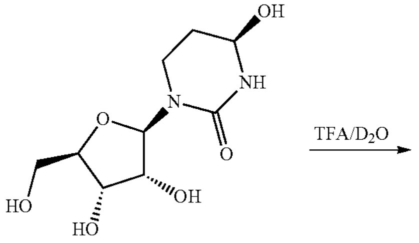

THU

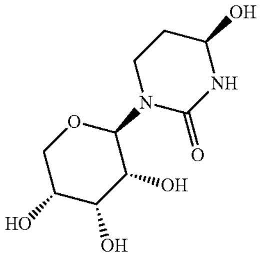

TH-pyranose

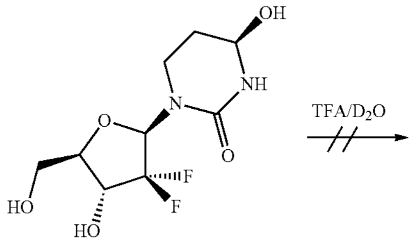

Compound 1a

Figure 10:
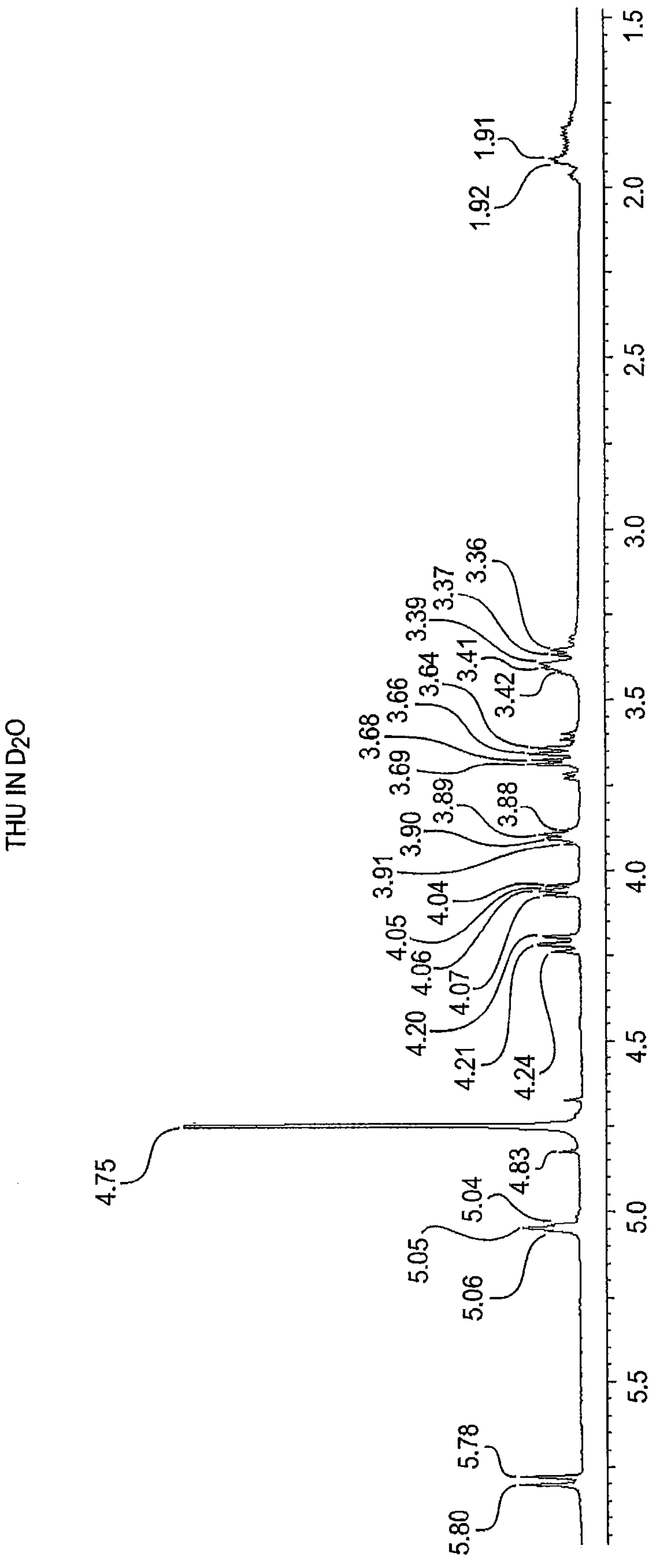
FIG. 10 is the $^{1}H$ NMR structure of THU in $D_20$.
Figure 11A:
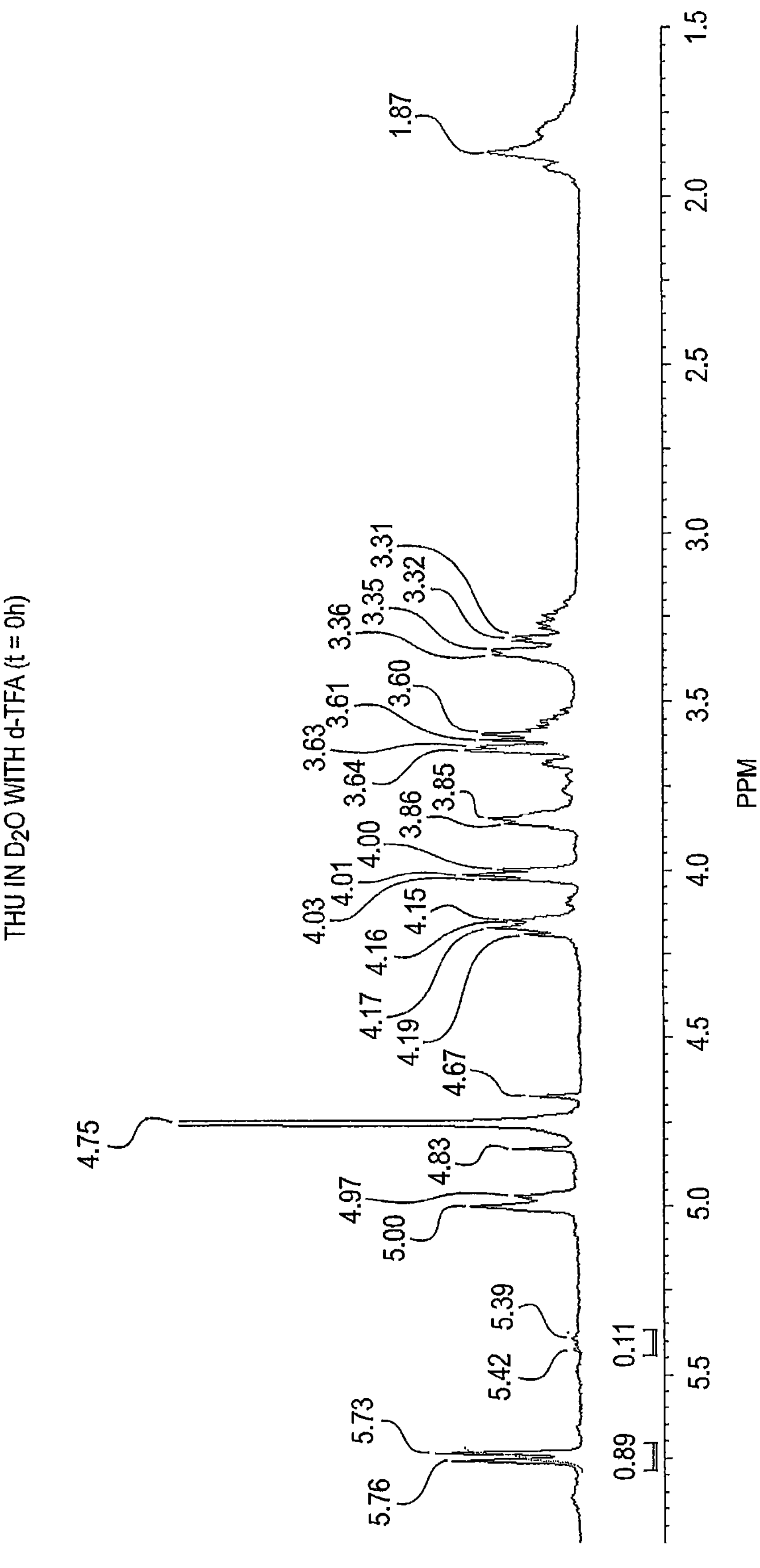
FIGS. 11A-11C show the $^{1}H$ NMR structure of THU in $D_20$, in the presence of trifluoroacetic acid, at different times.
Figure 11B:
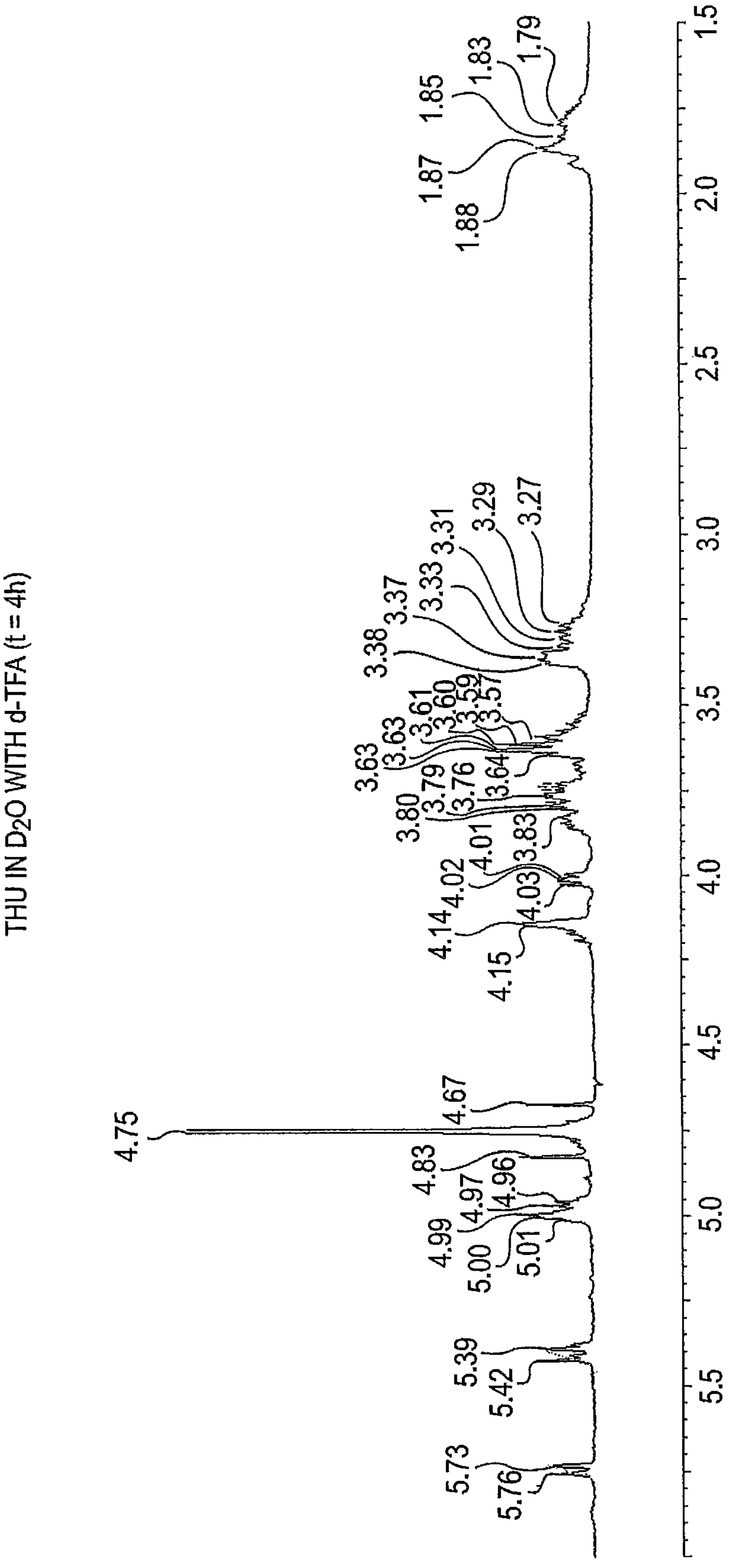
Figure 11C:
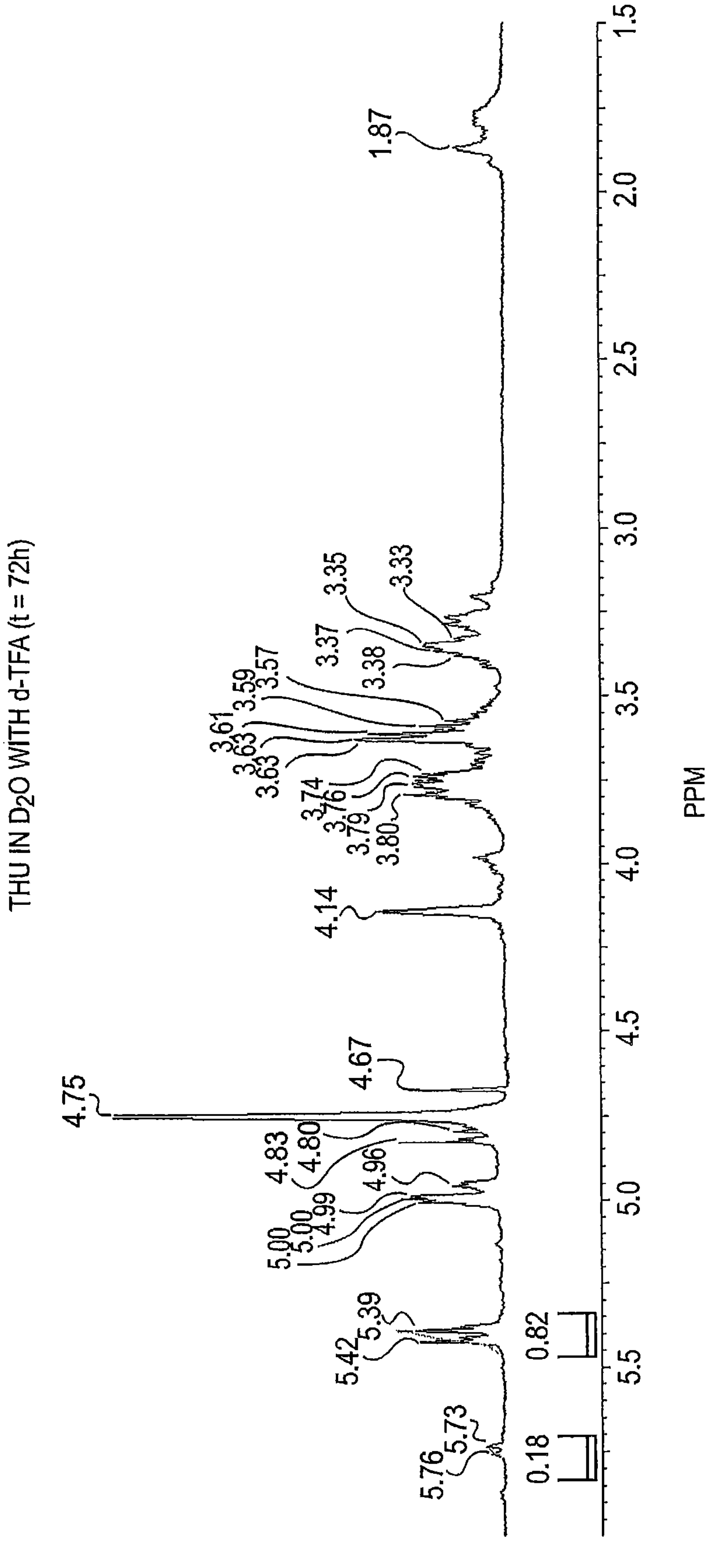

Tetrahydrouridine (THU, 5 mg) is dissolved in $D_2O$ (0.75 mL). The $^1$HNMR ($D_2O$, 300 MHz, 27° C.) spectrum is shown in FIG. 10. To this same sample is added one drop of deuterated TFA followed by an immediate $^1$HNMR spectrum (FIG. 10). Even at this earliest time point, the peak at 5.4 ppm (~10% conversion by integration) is indicative of the ring expansion to the TH-pyranose. Over the next several hours, spectra ($D_2O$, 300 MHz, 27° C.) are taken as shown in FIG. 11. After 4 hours, the TH-pyranose is more prevalent indicating about 60% conversion. At 72 hours, the conversion is almost entirely complete (>80%). Notable changes in the region from 4.0-4.5 are also indicative of THU decomposition and the TH-pyranose formation.

Figure 12:
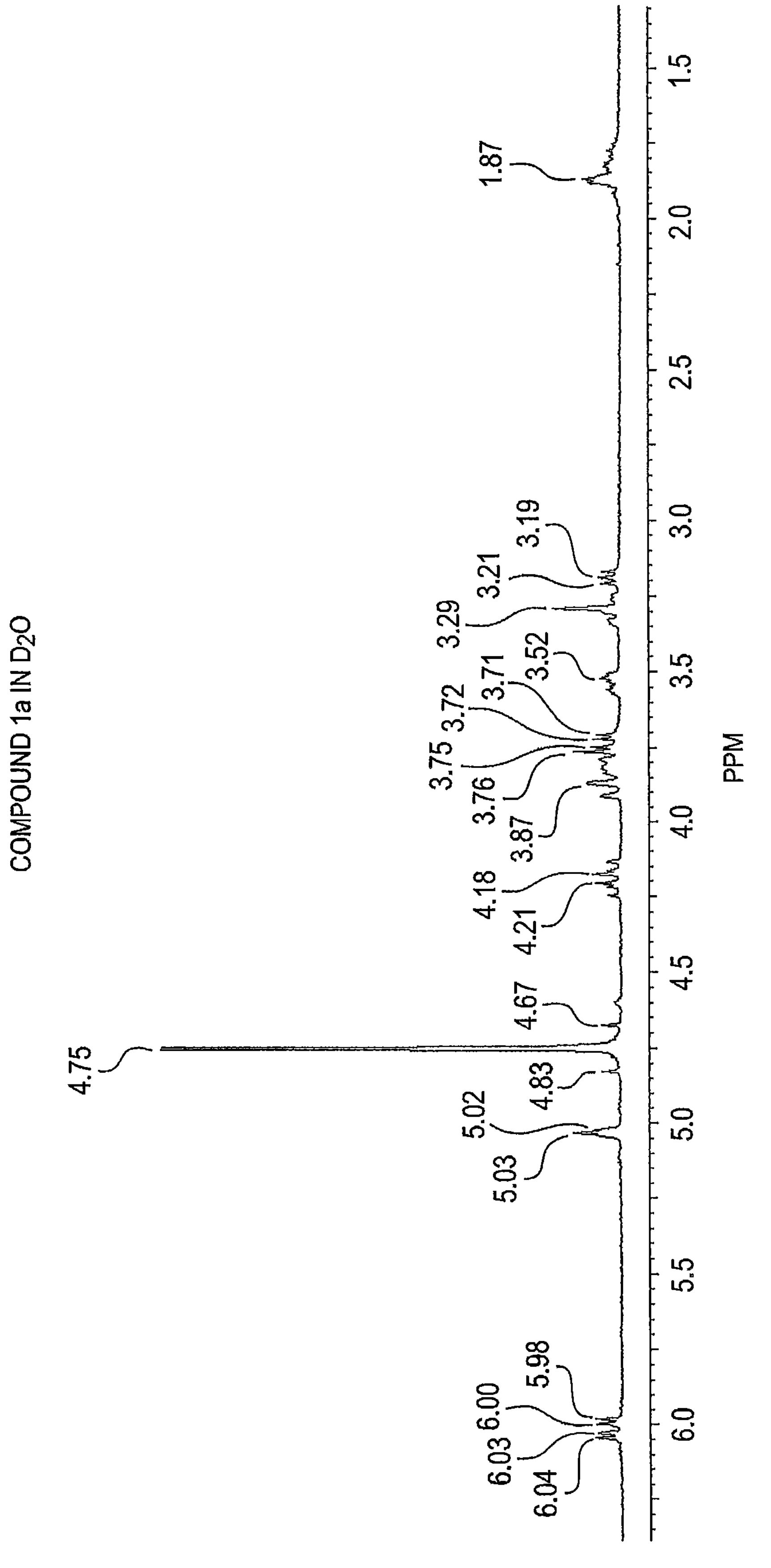
FIG. 12 is the $^{1}H$ NMR structure of Compound 1a in $D_20$.
Figure 13A:
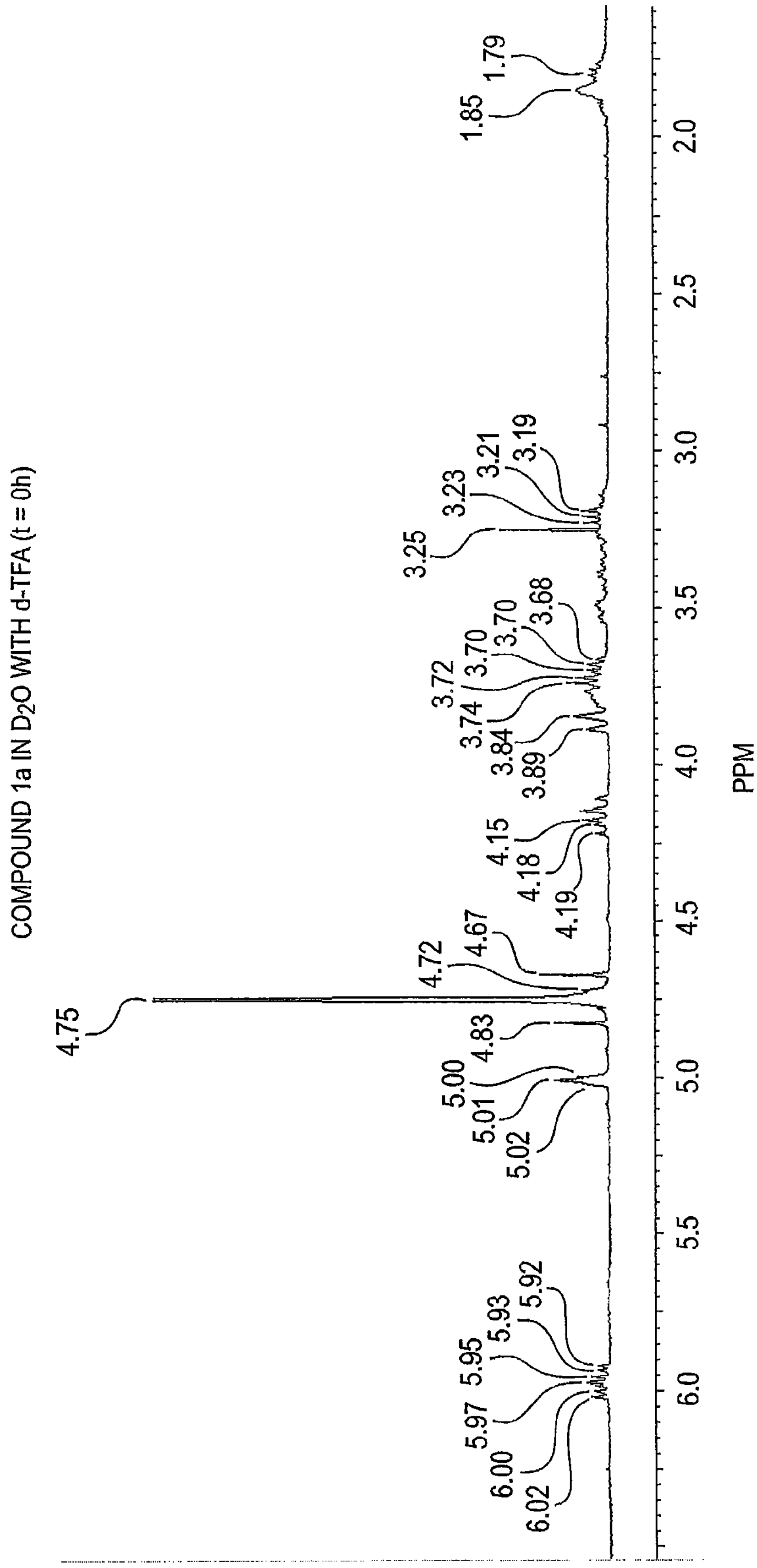
FIGS. 13A-13C show the $^{1}H$ NMR structure of Compound 1a in $D_20$, in the presence of trifluoroacetic acid, at different times.
Figure 13B:
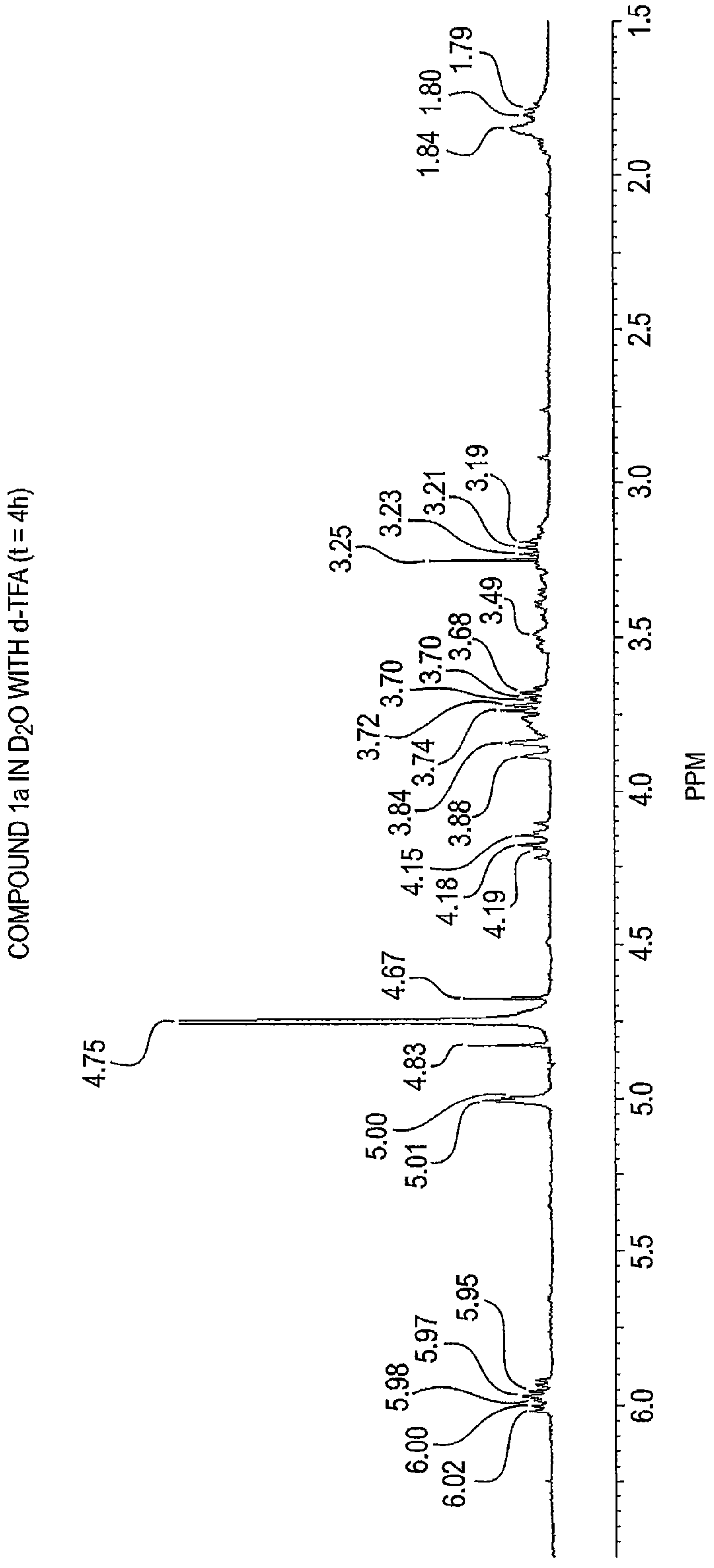
Figure 13C:
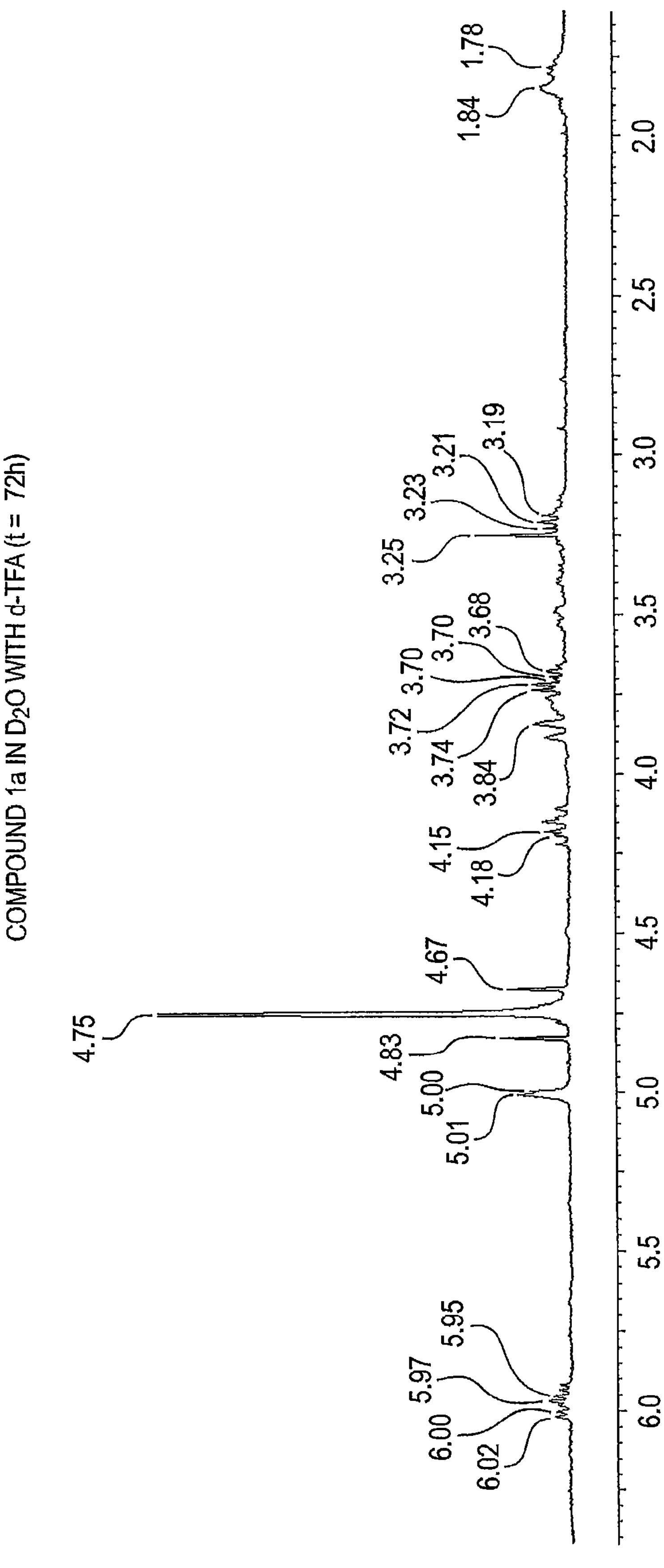

Compound 1a (5 mg) is dissolved in $D_2O$ (0.75 mL). The $^1$HNMR spectrum ($D_2O$, 300 MHz, 27° C.) is shown in FIG. 12. To this same sample is added one drop of deuterated TFA followed by an immediate $^1$HNMR spectrum (FIG. 12). After the first time point, the only notable change is the epimerization of the aminal which is noted by the extra peaks at 5.92 and 5.93. After 4 hours and 72 hours (FIG. 13), there are no other notable changes in the spectra ($D_2O$, 300 MHz, 27° C.). These results indicate that no pyranose formation occurs with Compound 1a under these conditions.

Certain Embodiments of the Invention

1. A compound of formula I

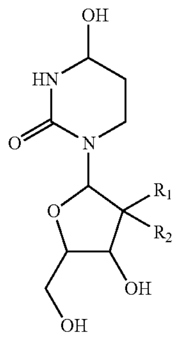

I or a pharmaceutically acceptable salt of the compound, wherein:

$R_1$ and $R_2$ are independently selected from the group consisting of hydrogen, halo, cyano, nitro, sulfhydryl, hydroxyl, formyl, carboxyl, COO($C_1$ to $C_6$ straight or branched chain alkyl), COO($C_1$ to $C_6$ straight or branched chain alkenyl), COO($C_1$ to $C_6$ straight or branched chain alkynyl), CO($C_1$ to $C_6$ straight or branched chain alkyl), CO($C_1$ to $C_6$ straight or branched chain alkenyl), CO($C_1$ to $C_6$ straight or branched chain alkynyl), $C_1$ to $C_6$ straight or branched chain alkyl, $C_1$ to $C_6$ straight or branched chain alkenyl, $C_1$ to $C_6$ straight or branched chain alkynyl, $C_1$ to $C_6$ straight or branched chain alkoxy, and $C_1$ to $C_6$ straight or branched chain alkenoxy; wherein each occurrence of $C_1$ to $C_6$ straight or branched chain alkyl, $C_1$ to $C_6$ straight or branched chain alkenyl, $C_1$ to $C_6$ straight or branched chain alkynyl, $C_1$ to $C_6$ straight or branched chain alkoxy, or $C_1$ to $C_6$ straight or branched chain alkenoxy may be independently unsubstituted or substituted with one to four substituents independently selected from the group consisting of halo, hydroxyl, cyano, nitro, formyl, carboxyl, and sulfhydryl;

and provided that when one of $R_1$ and $R_2$ is —H, then the other is not —H, —OH or —$CH_2OH$.

2. A compound of embodiment 1, wherein $R_1$ and $R_2$ are independently selected from the group consisting of hydrogen, halo, hydroxyl, cyano, nitro, sulfhydryl, $C_1$ to $C_6$ straight or branched chain alkyl, $C_1$ to $C_6$ straight or branched chain alkenyl, $C_1$ to $C_6$ straight or branched chain alkynyl, $C_1$ to $C_6$ straight or branched chain alkoxy, and $C_1$ to $C_6$ straight or branched chain alkenoxy; wherein each occurrence of $C_1$ to $C_6$ straight or branched chain alkyl, $C_1$ to $C_6$ straight or branched chain alkenyl, $C_1$ to $C_6$ straight or branched chain alkynyl, $C_1$ to $C_6$ straight or branched chain alkoxy, or $C_1$ to $C_6$ straight or branched chain alkenoxy may be independently unsubstituted or substituted with one ore more halos;

and provided that when one of $R_1$ and $R_2$ is —H, then the other is not —H, or —OH.

3. A compound of embodiment 1, wherein $R_1$ and $R_2$ are independently selected from the group consisting of hydrogen, halo, $C_1$ to $C_6$ alkyl, $C_1$ to $C_6$ alkenyl, $C_1$ to $C_6$ alkoxy, and $C_1$ to $C_6$ alkenoxy; wherein each occurrence of $C_1$ to $C_6$ straight or branched chain alkyl, $C_1$ to $C_6$ straight or branched chain alkenyl, $C_1$ to $C_6$ straight or branched chain alkoxy and $C_1$ to $C_6$ straight or branched chain alkenoxy may be independently unsubstituted or substituted with one to three halos;

and provided that when one of $R_1$ and $R_2$ is —H, then the other is not —H, or —OH.

4. The compound of embodiment 1, wherein at least one of $R_1$ and $R_2$ is halo.

5. The compound of embodiment 1, wherein at least one of $R_1$ and $R_2$ is fluoro.

6. The compound of embodiment 1, wherein one of $R_1$ and $R_2$ is halo, and the other is —H.

7. The compound of embodiment 1, wherein one of $R_1$ and $R_2$ is fluoro, and the other is —H.

8. The compound of embodiment 1, wherein $R_1$ and $R_2$ are each fluoro.

9. The compound of embodiment 1, wherein one of $R_1$ and $R_2$ is halo, and the other is —CN.

10. The compound of embodiment 1, wherein one of $R_1$ and $R_2$ is fluoro, and the other is —CN.

11. The compound of embodiment 1, wherein one of $R_1$ and $R_2$ is halo, and the other is —$NO_2$.

12. The compound of embodiment 1, wherein one of $R_1$ and $R_2$ is fluoro, and the other is —$NO_2$.

13. The compound of embodiment 1, wherein one of $R_1$ and $R_2$ is halo, and the other is —SH.

14. The compound of embodiment 1, wherein one of $R_1$ and $R_2$ is fluoro, and the other is —SH.

15. The compound of embodiment 1, wherein one of $R_1$ and $R_2$ is halo, and the other is —OH.

16. The compound of embodiment 1, wherein one of $R_1$ and $R_2$ is fluoro, and the other is —OH.

17. The compound of embodiment 1, wherein one of $R_1$ and $R_2$ is halo, and the other is —CHO.

18. The compound of embodiment 1, wherein one of $R_1$ and $R_2$ is fluoro, and the other is —CHO.

19. The compound of embodiment 1, wherein one of $R_1$ and $R_2$ is halo, and the other is —COOH.

20. The compound of embodiment 1, wherein one of $R_1$ and $R_2$ is fluoro, and the other is —COOH.

21. The compound of embodiment 1, wherein one of $R_1$ and $R_2$ is halo, and the other is —$COOR_x$, and wherein $R_x$ selected from the group consisting of $C_1$ to $C_6$ straight or branched chain alkyl, $C_1$ to $C_6$ straight or branched chain alkenyl, and $C_1$ to $C_6$ straight or branched chain alkynyl.

22. The compound of embodiment 1, wherein one of $R_1$ and $R_2$ is fluoro, and the other is —$COOR_x$ and wherein $R_x$ selected from the group consisting of $C_1$ to $C_6$ straight or branched chain alkyl, $C_1$ to $C_6$ straight or branched chain alkenyl, and $C_1$ to $C_6$ straight or branched chain alkynyl.

23. The compound of embodiment 1, wherein one of $R_1$ and $R_2$ is halo, and the other is —$COR_K$, and wherein $R_x$ selected from the group consisting of $C_1$ to $C_6$ straight or branched chain alkyl, $C_1$ to $C_6$ straight or branched chain alkenyl, and $C_1$ to $C_6$ straight or branched chain alkynyl.

24. The compound of embodiment 1, wherein one of $R_1$ and $R_2$ is fluoro, and the other is —$COR_x$, and wherein $R_x$ selected from the group consisting of $C_1$ to $C_6$ straight or branched chain alkyl, $C_1$ to $C_6$ straight or branched chain alkenyl, and $C_1$ to $C_6$ straight or branched chain alkynyl.

25. The compound of embodiment 1, wherein one of $R_1$ and $R_2$ is halo, and the other is —$C_1$ to $C_6$ straight or branched chain alkyl.

26. The compound of embodiment 1, wherein one of $R_1$ and $R_2$ is fluoro, and the other is —$C_1$ to $C_6$ straight or branched chain alkyl.

27. The compound of embodiment 1, wherein one of $R_1$ and $R_2$ is halo, and the other is —$C_1$ to $C_6$ straight or branched chain alkenyl.

28. The compound of embodiment 1, wherein one of $R_1$ and $R_2$ is fluoro, and the other is —$C_1$ to $C_6$ straight or branched chain alkenyl.

29. The compound of embodiment 1, wherein one of $R_1$ and $R_2$ is halo, and the other is —$C_1$ to $C_6$ straight or branched chain alkoxy.

30. The compound of embodiment 1, wherein one of $R_1$ and $R_2$ is fluoro, and the other is —$C_1$ to $C_6$ straight or branched chain alkoxy.

31. The compound of embodiment 1, wherein one of $R_1$ and $R_2$ is halo, and the other is —$C_1$ to $C_6$ straight or branched chain alkenoxy.

32. The compound of embodiment 1, wherein one of $R_1$ and $R_2$ is fluoro, and the other is —$C_1$ to $C_6$ straight or branched chain alkenoxy.

33. The compound of embodiment 1, wherein at least one of $R_1$ and $R_2$ is —$C_1$ to $C_6$ straight or branched chain alkyl substituted with halo.

34. The compound of embodiment 1, wherein one of $R_1$ and $R_2$ is —$C_1$ to $C_6$ straight or branched chain alkyl substituted with halo, and the other is —H.

35. The compound of embodiment 1, wherein one of $R_1$ and $R_2$ is —$C_1$ to $C_6$ straight or branched chain alkyl substituted with fluoro, and the other is —H.

36. The compound of embodiment 1, wherein at least one of $R_1$ and $R_2$ is —$C_1$ to $C_6$ straight or branched chain alkenyl substituted with halo.

37. The compound of embodiment 1, wherein one of $R_1$ and $R_2$ is —$C_1$ to $C_6$ straight or branched chain alkenyl substituted with halo, and the other is —H.

38. The compound of embodiment 1, wherein one of $R_1$ and $R_2$ is —$C_1$ to $C_6$ straight or branched chain alkenyl substituted with fluoro, and the other is —H.

39. The compound of embodiment 1, wherein at least one of $R_1$ and $R_2$ is/are —$C_1$ to $C_6$ straight or branched chain alkoxy substituted with halo 40. The compound of embodiment 1, wherein one of $R_1$ and $R_2$ is —$C_1$ to $C_6$ straight or branched chain alkoxy substituted with halo, and the other is —H.

41. The compound of embodiment 1, wherein one of $R_1$ and $R_2$ is —$C_1$ to $C_6$ straight or branched chain alkoxy substituted with fluoro, and the other is —H.

42. The compound of embodiment 1, wherein at least one of $R_1$ and $R_2$ is —$C_1$ to $C_6$ straight or branched chain alkenoxy substituted with halo.

43. The compound of embodiment 1, wherein one of $R_1$ and $R_2$ is —$C_1$ to $C_6$ straight or branched chain alkenoxy substituted with halo, and the other is —H.

44. The compound of embodiment 1, wherein one of $R_1$ and $R_2$ is —$C_1$ to $C_6$ straight or branched chain alkenoxy substituted with fluoro, and the other is —H.

45. The compound of any one of embodiments 1 to 44, wherein the compound of Formula I has the stereochemistry of either Ia or Ib:

Ia

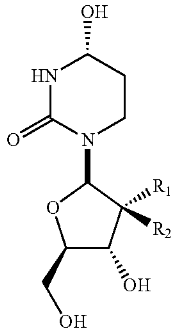

Ib

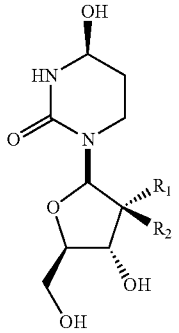

46. The compound of embodiment 1, wherein the compound is selected from Compounds 1 to 23:

Compound 1

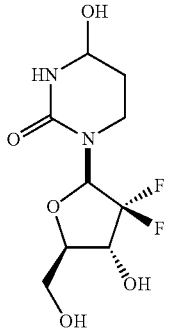

Compound 2

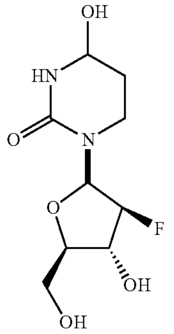

-continued
Compound 3
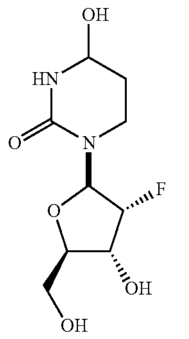
Compound 4
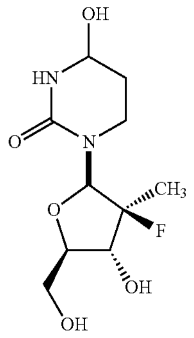
Compound 5
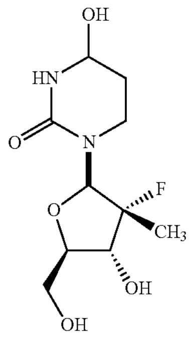
Compound 6
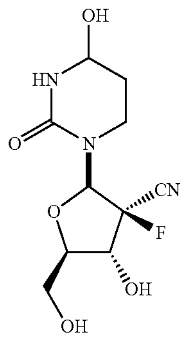
-continued
Compound 7
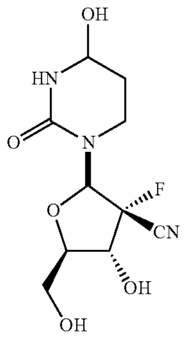
Compound 8
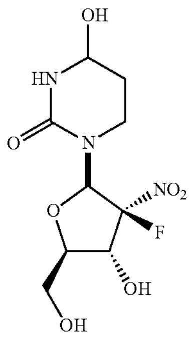
Compound 9
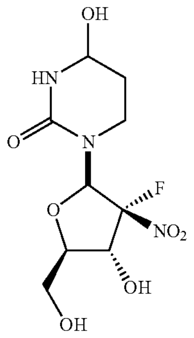
Compound 10
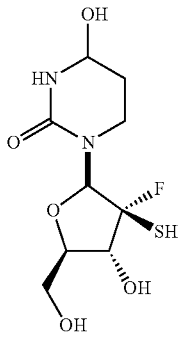

-continued
Compound 11
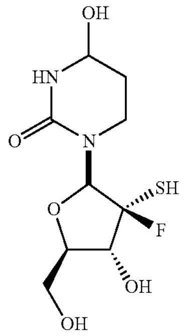
Compound 12
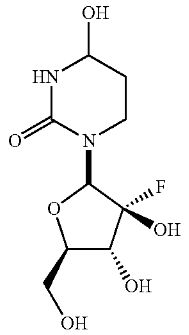
Compound 13
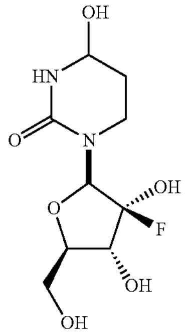
Compound 14
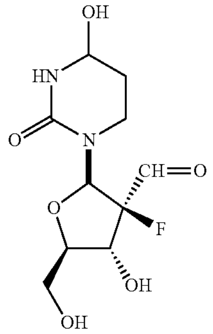
-continued
Compound 15
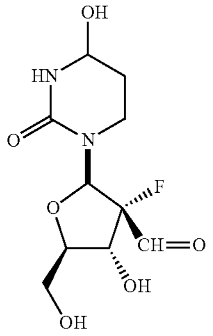
Compound 16
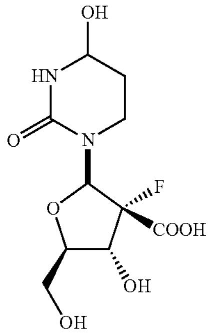
Compound 17
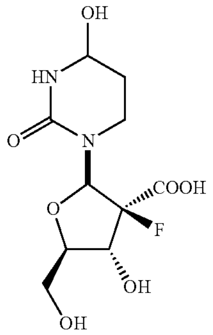
Compound 18
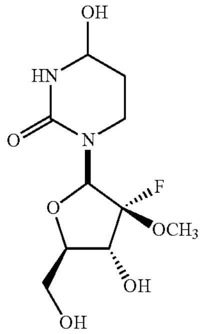

-continued
Compound 19
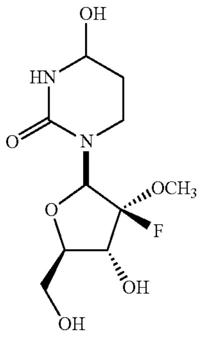
Compound 20
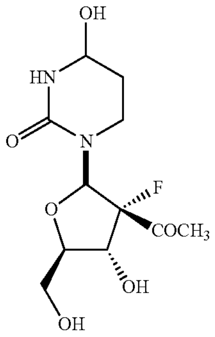
Compound 21
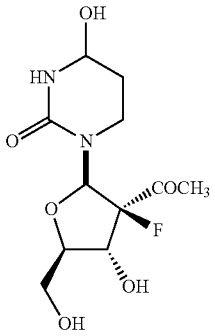
Compound 22
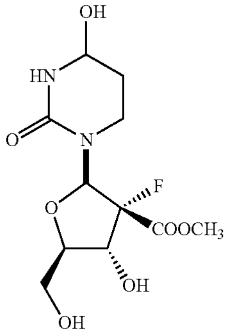
-continued
Compound 23
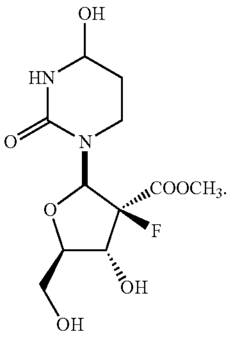
47. The compound of embodiment 1, wherein the compound is selected from the group consisting of 1a, 1b, 2a, 2b, 3a, and 3c:
Compound 1a
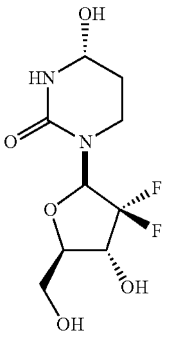
Compound 1b
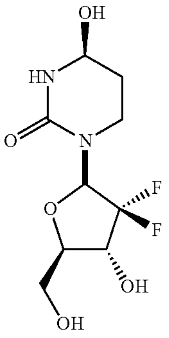
Compound 2a
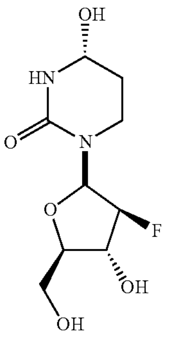

-continued

Compound 2b

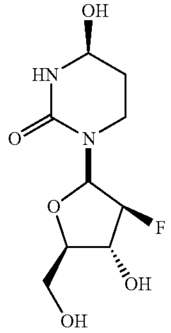

Compound 3a

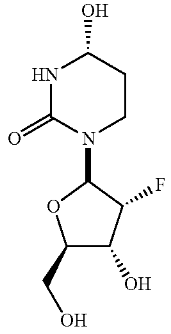

Compound 3b

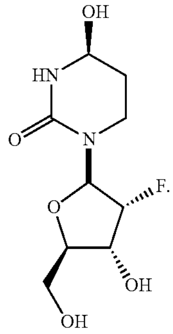

48. A pharmaceutical composition comprising:

(i) an effective amount of a compound of any one of embodiments 1 to 47 or a pharmaceutically acceptable salt thereof; and (ii) a pharmaceutically acceptable excipient.

49. A method for inhibiting cytidine deaminase, comprising administering to a subject in need thereof an effective amount of a compound or pharmaceutical composition of any one of embodiments 1 to 47.

50. A method for treating cancer comprising administering to a subject in need thereof:

(i) an effective amount of a compound or pharmaceutical composition of any one of embodiments 1 to 48; and (ii) a CDA substrate drug.

51. A method for inhibiting degradation of a CDA substrate drug by cytidine deaminase, comprising administering an effective amount of a compound or pharmaceutical composition of any one of embodiments 1 to 48 to a subject that is undergoing treatment with the CDA substrate drug.

52. The method of any one of embodiments 49 to 51, wherein the CDA substrate drug is selected from decitabine, 5-azacytidine, gemcitabine, ara-C, troxacitabine, tezacitabine, 5'-fluoro-2'-deoxycytidine, and cytochlor.

53. The method of any one of embodiments 49 to 52, wherein the compound of claim 1 is administered prior to the CDA substrate drug.

54. The method of any one of embodiments 49 to 52, wherein the compound of claim 1 is administered at substantially the same time with the CDA substrate drug.

55. The method of any one of embodiments 49 to 52, wherein the compound of claim 1 is administered after the CDA substrate drug.

56. The method of any one of embodiments 49 to 55, wherein the subject is a mammal.

57. The method of any one of embodiments 49 to 55, wherein the subject is a human.

58. The method of any one of embodiments 50 and 52 to 57, wherein the cancer is selected from hematological cancers and solid cancers.

59. The method of any one of embodiments 50 and 52 to 57, wherein the cancer is a hematological cancer selected from MDS and leukemia.

60. The method of embodiment 59, wherein the leukemia is AML or CML.

61. The method of embodiment 58, where the cancer is a solid cancer selected from pancreatic cancer, ovarian cancer, peritoneal cancer, non small cell lung cancer, and breast cancer.

62. A kit comprising at least one unit dosage form, wherein the unit dosage form comprises a compound or pharmaceutical composition of any one of embodiments 1 to 48.

63. A compound of Formula I, or a pharmaceutically acceptable salt thereof:

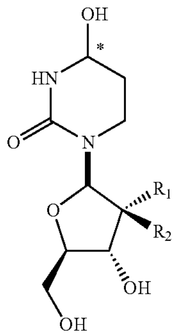

I wherein the carbon marked by an asterisk may have an (R) or an (S) configuration; and wherein $R_1$ and $R_2$ are independently selected from fluoro and hydrogen, with the proviso that $R_1$ and $R_2$ may not both be hydrogen.

64. A compound of Formula I selected from the group consisting of

Compound 1

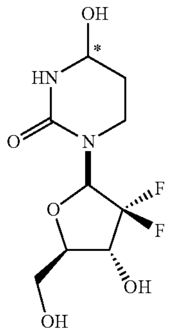

-continued

Compound 2

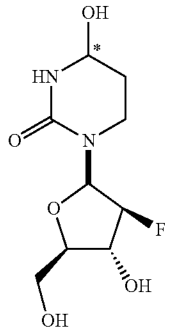

Compound 3

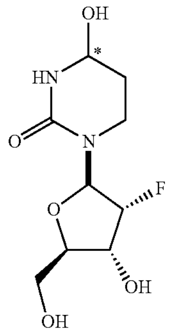

wherein each carbon atom marked with a * has a stereochemical configuration selected from the group consisting of an (R) configuration, an (S) configuration or a mixture of (R) and (S) configurations; and pharmaceutically acceptable salts thereof.

65. The compound of embodiment 64, wherein the compound is Compound 1.

66. The compound of embodiment 65, wherein Compound 1 has a stereochemistry represented by Compound 1a:

Compound 1a

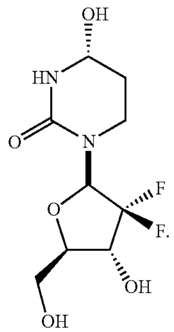

67. The compound of embodiment 65, wherein Compound 1 has a stereochemistry represented by Compound 1b:

Compound 1b

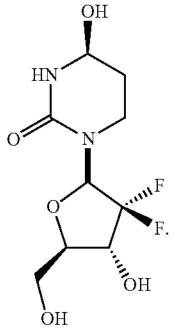

68. The compound of embodiment 64, wherein the compound is Compound 2.

69. The compound of embodiment 68, wherein Compound 2 has a stereochemistry represented by Compound 2a:

Compound 2a

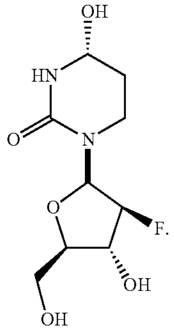

70. The compound of embodiment 68, wherein Compound 2 has a stereochemistry represented by Compound 2b:

Compound 2b

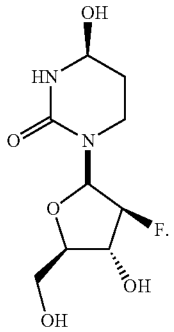

71. The compound of embodiment 64, wherein the compound is Compound 3.

72. The compound of embodiment 71, wherein Compound 3 has a stereochemistry represented by Compound 3a:

Compound 3a

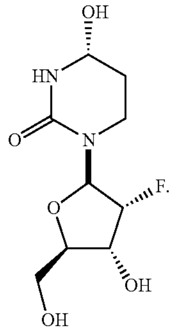

73. The compound of embodiment 71, wherein Compound 3 has a stereochemistry represented by Compound 3b:

Compound 3b

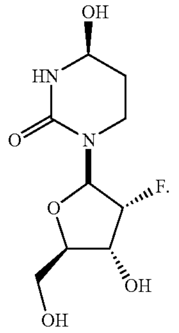

74. A pharmaceutical composition comprising a compound of embodiment 64 or a pharmaceutically acceptable salt thereof, and a pharmaceutically acceptable excipient.

75. The pharmaceutical composition of embodiment 74, further comprising a CDA substrate drug.

76. The pharmaceutical composition of embodiment 75, wherein the CDA substrate drug is selected from the group consisting of decitabine, 5-azacytidine, gemcitabine, ara-C, troxacitabine, tezacitabine, 5'-fluoro-2'-deoxycytidine, and cytochlor.

77. A method for treating cancer, comprising the steps of (i) administering to a mammal in need thereof a first pharmaceutical composition comprising an effective amount of a compound of embodiment 64; and (ii) administering to a mammal in need thereof a second pharmaceutical composition comprising a CDA substrate drug.

78. The method of embodiment 77, wherein the CDA substrate drug is selected from the group consisting of decitabine, 5-azacytidine, gemcitabine, ara-C, troxacitabine, tezacitabine, 5'-fluoro-2'-deoxycytidine, and cytochlor.

79. The method of embodiment 77, wherein said cancer is a cancer being treated with a CDA substrate drug.

80. The method of embodiment 77, wherein the cancer is selected from the group consisting of hematological cancers and solid cancers.

81. The method of embodiment 80, wherein the cancer is a hematological cancer selected from the group consisting of myelodysplastic syndrome and leukemia.

82. The method of embodiment 81, wherein the leukemia is acute myeloid leukemia or chronic myeloid leukemia.

83. The method of embodiment 80, where the cancer is a solid cancer selected from the group consisting of pancreatic cancer, ovarian cancer, peritoneal cancer, non small cell lung cancer, and metastatic breast cancer.

84. A method for inhibiting degradation of a CDA substrate drug by cytidine deaminase, comprising administering an effective amount of a pharmaceutical composition comprising a compound of embodiment 64 to a mammal that is undergoing treatment with said CDA substrate drug.

85. The method of embodiment 84 wherein the CDA substrate drug is selected from the group consisting of decitabine, 5-azacytidine, gemcitabine, ara-C, troxacitabine, tezacitabine, 5'-fluoro-2'-deoxycytidine, and cytochlor.

86. A compound of embodiment 64 for use in inhibiting cytidine deaminase in a subject in need thereof.

87. Use of a compound of embodiment 64 for the manufacture of a medicament for inhibiting cytidine deaminase in a subject in need thereof.

88. A compound of embodiment 64 for use in treating cancer in a subject being treated with a CDA substrate drug.

89. Use of a compound of embodiment 64 for the manufacture of a medicament for treating cancer in a subject being treated with a CDA substrate drug.

90. A compound of embodiment 64 for use in inhibiting degradation of a CDA substrate drug by cytidine deaminase in a mammal that is undergoing treatment with the CDA substrate drug.

91. Use of a compound of embodiment 64 for the manufacture of a medicament for inhibiting degradation of a CDA substrate drug by cytidine deaminase.

92. The method of embodiment 77, wherein the compound of embodiment 64 is administered prior to the CDA substrate drug.

93. The method of embodiment 77, wherein the compound of embodiment 64 is administered at substantially the same time with the CDA substrate drug.

94. The method of embodiment 77, wherein the compound of embodiment 64 is administered after the CDA substrate drug.

95. A pharmaceutical composition comprising a compound of claim 2 or a pharmaceutically acceptable salt thereof, and decitabine; and a pharmaceutically acceptable excipient.

96. A method for treating cancer, comprising the steps of:

(i) administering to a mammal in need thereof a first pharmaceutical composition comprising an effective amount of a compound of claim 2; and (ii) administering to a mammal in need thereof a second pharmaceutical composition comprising decitabine.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the spirit and scope of the present invention. All such modifications are intended to be within the scope of the claims appended hereto.

All patents and publications cited above are hereby incorporated by reference.

What is claimed is:

1. A method of producing compound 1a:

1a

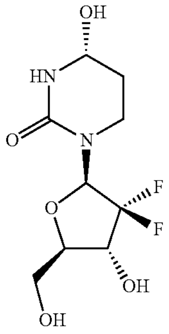

or a pharmaceutically salt thereof;

comprising reducing compound 25:

25

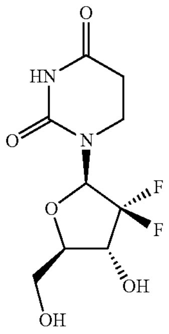

to produce compound 1a:

1a

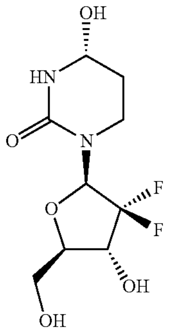

or a pharmaceutically salt thereof.

2. The method of claim 1, further comprising a step of purifying the final product by preparative HPLC.

3. The method of claim 1, wherein the reduction is carried out in the presence of sodium borohydride.

4. A method of producing compound 1a:

1a

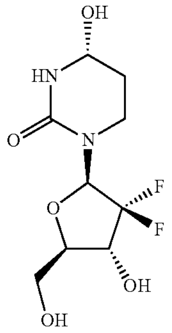

or a pharmaceutically salt thereof;
comprising the steps of:
(a) hydrogenating compound 24:

24

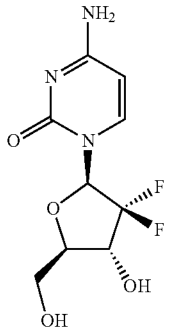

to produce compound 25:

25

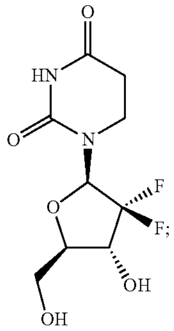

and (b) reducing compound 25 to produce compound 1a:

1a

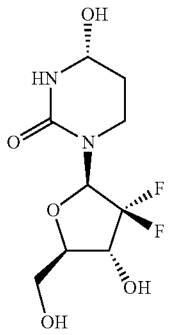

or a pharmaceutically salt thereof.

5. The method of claim 4, further comprising a step of purifying the final product by preparative HPLC.

6. The method of claim 4, wherein step (a) is carried out in the presence of rhodium on alumina.

7. The method of claim 4, wherein step (b) is carried out in the presence of sodium borohydride.

8. A crystalline form of compound 1a:

1a

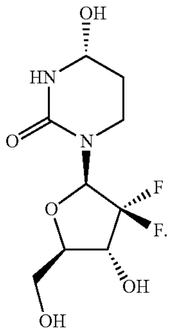

9. The crystalline form of compound 1a of claim 8, having a primitive trigonal cell with dimensions:

a=9.78961(18) Å c=20.4588(7) Å

V=1698.02(7) Å.

* * * * *

UNITED STATES PATENT AND TRADEMARK OFFICE

CERTIFICATE OF CORRECTION

PATENT NO. : 9,567,363 B2
APPLICATION NO. : 14/584437
DATED : February 14, 2017
INVENTOR(S) : Hamilton et al.

It is certified that error appears in the above-identified patent and that said Letters Patent is hereby corrected as shown below:

On the Title Page

References, Page 4, Right Column, Last entry:
Please correct "Henze "Nucleic Acids.IV." to read -- Hanze "Nucleic Acids.IV. --

In the Specification

Column 45, Line 50: Please correct "maximum 20 value" to read -- maximum 2θ value --
Line 51: Please correct "using co scans" to read -- using ω scans --
Line 53: Please correct "to 200.0° in 5.00" to read -- to 200.0° in 5.0° --

Column 50, Line 59: Please correct "the other is –$COR_k$, and" to read -- the other is – $COR_x$, and --

Signed and Sealed this
Fifth Day of September, 2017

Joseph Matal
*Performing the Functions and Duties of the*
*Under Secretary of Commerce for Intellectual Property and*
*Director of the United States Patent and Trademark Office*